United States Patent
Choo et al.

(10) Patent No.: US 11,512,292 B2
(45) Date of Patent: Nov. 29, 2022

(54) CYTOTOXIC ANTIBODY

(71) Applicant: Agency for Science, Technology and Research, Singapore (SG)

(72) Inventors: Boon Hwa Andre Choo, Singapore (SG); Jiyun Zheng, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 601 days.

(21) Appl. No.: 16/545,736

(22) Filed: Aug. 20, 2019

(65) Prior Publication Data

US 2020/0140828 A1     May 7, 2020

Related U.S. Application Data

(62) Division of application No. 15/101,586, filed as application No. PCT/SG2014/000570 on Dec. 2, 2014, now Pat. No. 10,428,312.

(30) Foreign Application Priority Data

Dec. 3, 2013    (SG) ................ 201308964-4

(51) Int. Cl.
| | | |
|---|---|---|
| *C07K 16/18* | (2006.01) | |
| *C12N 5/16* | (2006.01) | |
| *C07K 16/44* | (2006.01) | |
| *C12N 5/00* | (2006.01) | |

(52) U.S. Cl.
CPC .............. *C12N 5/163* (2013.01); *C07K 16/18* (2013.01); *C07K 16/44* (2013.01); *C12N 5/0081* (2013.01); *C07K 2317/35* (2013.01); *C07K 2317/565* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 4,607,009 A | 8/1986 | Steplewski et al. | |
| 7,491,391 B2 | 2/2009 | Benson et al. | |
| 8,481,688 B2 | 7/2013 | Weng et al. | |
| 8,906,678 B2 * | 12/2014 | Choo ................ | C12N 5/0606 435/325 |
| 9,334,324 B2 * | 5/2016 | Choo .................... | C07K 16/28 |
| 9,354,228 B2 | 5/2016 | Vasquez et al. | |
| 9,388,246 B2 | 7/2016 | Gauthier et al. | |
| 10,287,547 B2 * | 5/2019 | Ding ................ | C07K 16/2803 |

FOREIGN PATENT DOCUMENTS

| | | |
|---|---|---|
| WO | WO-2007/102787 A1 | 9/2007 |
| WO | WO-2008/087259 A1 | 7/2008 |
| WO | WO-2012/011876 A1 | 1/2012 |

OTHER PUBLICATIONS

Abaza, M.S. and Atassi, M.Z., Effects of amino acid substitutions outside an antigenic site on protein binding to monoclonal antibodies of predetermined specificity obtained by peptide immunization: demonstration with region 94-100 (antigenic site 3) of myoglobin, J. Protein Chem., 11(5): 433-444 (1992).
Colman et al., Research in Immunology, 145(1): 33-36 (1994).
International Search Report for PCT/SG2014/000570, 6 pages (dated Jun. 23, 2015).
Lederman et al., Molecular Immunology, 28: 1171-1181 (1991).
Paul, Fundamental Immunology, (textbook), under the heading Immunoglobulins: Structure and Function, pp. 37, 43, 58, 59 (1999).
Rudikoff et al., Proc Natl Acad Sci USA, 79: 1979-1983 (1982).
Written Opinion for PCT/SG2014/000570, 6 pages (dated Jun. 23, 2015).

\* cited by examiner

*Primary Examiner* — Michail A Belyavskyi
(74) *Attorney, Agent, or Firm* — Choate, Hall & Stewart LLP; Charles E. Lyon; Brian E. Reese

(57) ABSTRACT

An antibody that binds a glycosylated protein is disclosed, wherein the glycosylation comprises the glycan motif Fucα1-2Galβ1-3GlcNAcβ1-3Galβ1 or Fucα1-2Galβ1-3GlcNAc. Antibodies that are cytotoxic against undifferentiated pluripotent cells are also disclosed.

13 Claims, 44 Drawing Sheets

Specification includes a Sequence Listing.

| Stage | Principle | Advantages | Disadvantages | Examples | Ref |
|---|---|---|---|---|---|
| 1. Pre-transplantation stage: terminally differentiate hESC or selectively remove undifferentiated hESC | | | | | |
| Induced differentiation of remaining undifferentiated cells | Extended differentiation or additional differentiated steps by chemical induction | Easy to perform, Inexpensive; | Differentiation efficiency is crucial, Unclear about the effect of chemicals on desired cell; | Direct hESC differentiation to motor neuron progenitors in the presence of retinoic acid (RA) and sonic hedgehog (SHH) | 21,32 |
| Removal by specific antibodies or inhibitors | Purification of desired cell or removal of undesired cells with specific antibodies or inhibitors | High specificity; | Antibody and inhibitor specificity is crucial, Costs, | MACS or FACS sorting of well-characterized surface antigens, such as SSEA-4 and TRA-1-60, or inducing hESC death by cytotoxic mAb84, scFv84-HTH, or inhibitor | 37,38,47-51 |
| Selection by transgenic fluorescent marker | Purification of desired cell or removal of undesired cells with transgenic fluorescent marker | High specificity, High yield; | Genetic manipulation introduce another safety hurdle; | Genetic selection of sox1GFP-expressing neural precursors against undifferentiated hESC or removal of Oct-4 GFP-expressing undifferentiated hESC | 52,53 |
| Purification on physical properties | Division by differences in cell adherence or density gradient centrifugation | Easy to perform, Fast, Inexpensive; | Low specificity, Low yields; | Percoll density centrifugation enrich hESC-derived Cardiomyocytes | 54,55 |
| 2. Early post-transplantation stage: interrupt tumor progression | | | | | |
| Prevention of tumor formation by cytotoxic drugs | Selectively targeting teratoma-forming cells with high proliferation rate | Easy to perform, Inexpensive, Fast; | Only active teratoma-forming cells can be targeted, Dormant cells cannot be eliminated; | Induction of apoptosis in undifferentiated cells expressing Oct-4/PAR-4 by ceramide analogues | 56 |
| Interruption of tumor formation by genetic engineering | Transfection with a fusion gene consisting a "suicide gene" and a fluorescent marker | Able to trace the kinetics of teratoma formation, Timely, High yields; | All cells carrying the "suicide gene" are eliminated, Genetically modified cells are prone to transformation; | Termination of undergoing teratomas formation by applying ganciclovir to hESC carrying thymidine kinase (TK) and fluorescent marker to induce cell death | 57-59 |
| 3. Late post-transplantation stage: remove detected tumor | | | | | |
| Removal of detected tumor by genetic engineering | Transfection of hESC with transgenic viral gene and induce cell death with specific drugs | High yields; | All cells carrying the "suicide gene" are eliminated, Genetically modified cells are prone to transformation | Removal of detected tumors by applying ganciclovir to hESC carrying thymidine kinase (TK) to induce cell death | 60 |

Figure 1

| Antibody | Target cell | Target antigen | Mode of cell death |
|---|---|---|---|
| MEM-59 | Hematopoietic progenitor cells | CD43 | Apoptosis |
| Rituximab | Non-hodgkin's lymphoma | CD20 | Apoptosis |
| GA101 | Non-hodgkin's lymphoma | CD20 | Oncosis |
| Tositumomab | Human lymphoma cells | CD20 | Oncosis |
| anti-HLA-DR mAbs | Primary chronic lymphocytic leukemia cells | HLA-DR | Oncosis |
| RAV12 | Adenocarcinoma | RAAG12 | Oncosis |
| Anti-porimin | Jurkat cell | Porimin | Oncosis |
| RE2 | Interleukin 2-dependent T cell | n.a. | Oncosis |
| Anti-NeuGcGM3 14F7 | Breast carcinoma and melanoma cells | NeuGcGM3 | Oncosis |
| Anti-NeuGcGM3 Abs | Lung tumor cells | NeuGcGM3 | Oncosis |

Figure 2

| Hallmarks | Assays |
|---|---|
| Cell shrinkage and apoptotic body formation | Electron microscope (TEM or SEM) |
| Caspase activation | Measure caspase activity |
| Phosphatidylserine externalization | Annexin V detection |
| DNA fragmentation | TUNEL assay |

Figure 3

| Hallmarks | Assays |
|---|---|
| Rapid cell death (within seconds to minutes) | Flow cytometry |
| Membrane damage | Uptake of trypan blue/propidium iodide/Dextran beads; Scanning electron microscope |
| Apparent swelling of cell and organelles | Transmission electron microscope |
| Cytoskeleton proteins degradation | Western Blot |
| Leakage of intracellular components | Change in lactate dehydrogenase concentration |

Figure 4A

| | Oncosis | Apoptosis |
|---|---|---|
| Cell death time | Fast (seconds to minutes) | Slow (12-24hrs) |
| Volume changes | Swelling of cytoplasm and mitochondria | Shrinking of cytoplasm and condensation of nucleus |
| Membrane damage | Yes | No |
| Cytoplasm | Released | Retained in apoptotic bodies |
| Degradation of Cytoskeleton-associated proteins | Involved | Not involved |
| Caspases activity | No | Yes |
| DNA fragmentation | Random | Ordered |
| Inflammation | Yes | No |

Figure 4B

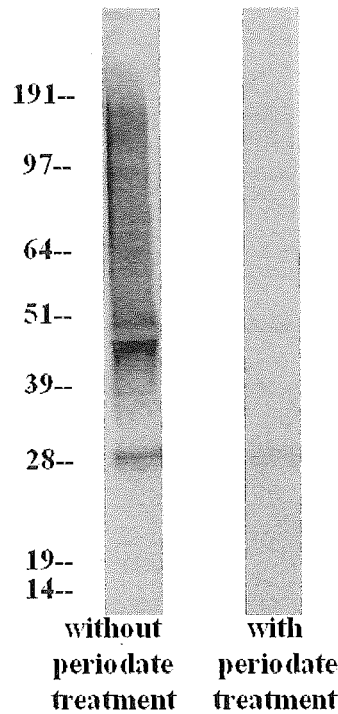

without periodate treatment    with periodate treatment

Figure 12A

| Cell Adhesion proteins |
PODXL, integrin α-6/α-5/α-1, integrinβ-1/β-5, SorLA-1, CD44, Protocadherin-1, Na/H exchanger, CD166, Neuroligin-4, Laminin γ-1, Neuroplastin, CD239, CD326, CD56, CD36, Cell adhesion molecule 1, CD111, CD113, Calsyntenin-1, Tubulin-specific chaperone D, Catenin α-1/β-1/Δ-1,

| Cytoskeleton-associated proteins |
Trans-Golgi network integral membrane protein 2, Prominin-1, Syndecan-1, Plexin-B2, CD100, Leucine-rich repeat neuronal protein 1, KIF 11/12, Dynamin-2, Alpha-actinin-1, NHERF-1, TCP-1-epsilon, TCP-1-delta, Filamin B

| ATPase proteins |
Na/K-transporting ATPase α-1/α-2/α-3/β-3, ATP5F1, CD340, E-NPP 1, Tyrosine-protein kinase Kit, CD331, SR Ca(2+)-ATPase 2, LACS 3, Hexokinase-1, V-ATPase subunit A, CTP synthase 1, PFK-A

| Transporter proteins |
CD98, GLUT-3, GLUT-2, GLUT-1, Sodium bicarbonate cotransporter 3, MRP46, K-Cl cotransporter 4, LTC4 transporter, Zinc transporter ZIP14, MOAT-C, MOAT-B, NPC1, SLC12A4, SLC5A6, Potassium-chloride transporter 9, MCT-1, Alpha-adaptin C, Beta-1-adaptin, Beta-COP, Alpha-COP, Gamma-2-COP, Exportin-2

Figure 12B

Heavy chain:

CDR H1                                                                                    CDR H2

84VH  QVQLQQSGGGLVQPGGSMKLSCVASGFTFSNYWMNWVRQSPEKGLEWVAEIRLKSNNYATHYAESVKGRFTISRDDSKSSVYL

A1H   QVKLQQSGGGLVQPGGSMKLSCVASGFTFSNYYMNWVRQSPEKGLEWVAEIRLKSNNYATHYAESVKGRFTISRDDSKSSVYL

Heavy chain:       CDR H3

84VH  QMNNLRAEDTGIYYCTGERAWGQGTTVTVSS    (SEQ ID NO: 7)

A1H   QMNNLRAEDTGIYYCEGFGYWGQGTTVTVSS    (SEQ ID NO: 8)

Figure 15A

Light chain:              CDR L1                                                          CDR L2

84L   DIELTQSPAIMSASPGEKVTMTCSASSSVNYMYWYQQKPGSSPRLLIYDTSNLASGVPVRFSGSGSGTSYSLTISR

A1L   DIELTQSPALMSASPGEKVTMTCSASSSVSYMFWYQQKPRSSPKPWIHLTSNLASGVPARFSGSGSGTSYSLTISS

Light chain:       CDR L3

84L   MEAEDAATYYCQQWSSYPYTFGGGTKLEIKR    (SEQ ID NO: 9)

A1L   MEAEDAATYYCQQWSSNPYTFGGGTKLEIKR    (SEQ ID NO: 10)

Figure 15B

Reduction in intensity $$=(I_x/I_{x\text{-GAPDH}} - I_{\text{-ve}}/I_{\text{-ve-GAPDH}})/(I_{\text{-ve}}/I_{\text{-ve-GAPDH}})$$

| Sugars | Structure | Sequence | Block A1 binding on hESC | Block A1 killing on hESC |
|---|---|---|---|---|
| Lewis<sup>a</sup> trisaccharide | | Galβ1-3(Fucα1-4)GlcNAc | − | − |
| Lewis<sup>b</sup> tetrasaccharide | | Fucα1-2Galβ1-3(Fucα1-4)GlcNAc | + | + |
| Lewis<sup>x</sup> trisaccharide | | Galβ1-4(Fucα1-3)GlcNAc | − | − |
| Lewis<sup>y</sup> tetrasaccharide | | (Fucα1-2)Galβ1-4(Fucα1-3)GlcNAc | − | − |
| Lacto-N-fucopentaose I (LNFP I) | 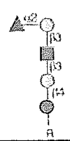 | (Fucα1-2)Galβ1-3GlcNAcβ1-3Galβ1-4Glc | + | + |
| Blood Group H type I trisaccharide | 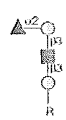 | Fucα1-2Galβ1-3GlcNAc | + | + |
| Blood Group H type II trisaccharide | 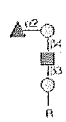 | Fucα1-2Galβ1-4GlcNAc | − | − |
| Blood Group A trisaccharide | 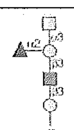 | GalNAcα1-3(Fucα1-2)Gal | − | − |
| Blood Group B trisaccharide | 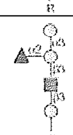 | Galα1-3(Fucα1-2)Gal | − | − |

Figure 23

Targets of NADPH oxidase inhibitors

| | Inhibitors | | |
|---|---|---|---|
| Isoforms | DPI | MPA | APO |
| Nox1 | √ | √ | |
| Nox2 | √ | √ | √ |
| Nox3 | √ | ? | |
| Nox4 | √ | | |
| Nox5 | √ | | |
| Duox1 | √ | | |
| Duox2 | √ | | |

SEQUENCE LISTING

<160> NUMBER OF SEQ ID NOS: 10

<210> SEQ ID NO 1
<211> LENGTH: 10
<212> TYPE: PRT
<213> ORGANISM: Artificial sequence

```
<220> FEATURE:
<223> OTHER INFORMATION: Synthetic sequence

<400> SEQUENCE: 1

Ser Ala Ser Ser Ser Val Ser Tyr Met Phe
1               5                   10

<210> SEQ ID NO 2
<211> LENGTH: 7
<212> TYPE: PRT
<213> ORGANISM: Artificial sequence
<220> FEATURE:
<223> OTHER INFORMATION: Synthetic sequence

<400> SEQUENCE: 2

Leu Thr Ser Asn Leu Ala Ser
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic sequence

<400> SEQUENCE: 3

Gln Gln Trp Ser Ser Asn Pro Tyr Thr
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic sequence

<400> SEQUENCE: 4

Gly Phe Thr Phe Ser Asn Tyr Tyr Met Asn
1               5                   10

<210> SEQ ID NO 5
<211> LENGTH: 19
<212> TYPE: PRT
<213> ORGANISM: Artificial sequence
<220> FEATURE:
<223> OTHER INFORMATION: Synthetic sequence

<400> SEQUENCE: 5

Glu Ile Arg Leu Lys Ser Asn Asn Tyr Ala Thr His Tyr Ala Glu Ser
1               5                   10                  15

Val Lys Gly

<210> SEQ ID NO 6
<211> LENGTH: 3
<212> TYPE: PRT
<213> ORGANISM: Artificial sequence
<220> FEATURE:
<223> OTHER INFORMATION: Synthetic sequence

<400> SEQUENCE: 6

Phe Gly Tyr
1

<210> SEQ ID NO 7
<211> LENGTH: 114
<212> TYPE: PRT
```

<213> ORGANISM: Artificial sequence
<220> FEATURE:
<223> OTHER INFORMATION: Synthetic sequence: Complete heavy chain of
      mAb84

<400> SEQUENCE: 7

Gln Val Gln Leu Gln Gln Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Thr Gly Glu Arg Ala Trp Gly Gln Gly Thr Thr Val Thr Val
            100                 105                 110

Ser Ser

<210> SEQ ID NO 8
<211> LENGTH: 114
<212> TYPE: PRT
<213> ORGANISM: Artificial sequence
<220> FEATURE:
<223> OTHER INFORMATION: Synthetic sequence: Complete heavy chain of mAb
      A1

<400> SEQUENCE: 8

Gln Val Lys Leu Gln Gln Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Tyr Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Asn Leu Arg Ala Glu Asp Thr Gly Ile Tyr
                85                  90                  95

Tyr Cys Glu Gly Phe Gly Tyr Trp Gly Gln Gly Thr Thr Val Thr Val
            100                 105                 110

Ser Ser

<210> SEQ ID NO 9
<211> LENGTH: 106
<212> TYPE: PRT

<213> ORGANISM: Artificial sequence
<220> FEATURE:
<223> OTHER INFORMATION: Synthetic sequence: Complete light chain of
    mAb84

<400> SEQUENCE: 9

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Asn Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Gln Gln Trp Ser Ser Tyr Pro Tyr Thr Phe
                85                  90                  95

Gly Gly Gly Thr Lys Leu Glu Ile Lys Arg
            100                 105

<210> SEQ ID NO 10
<211> LENGTH: 106
<212> TYPE: PRT
<213> ORGANISM: Artificial sequence
<220> FEATURE:
<223> OTHER INFORMATION: Synthetic sequence: Complete light chain of mAb
    A1

<400> SEQUENCE: 10

Asp Ile Glu Leu Thr Gln Ser Pro Ala Leu Met Ser Ala Ser Pro Gly
1               5                   10                  15

Glu Lys Val Thr Met Thr Cys Ser Ala Ser Ser Val Ser Tyr Met
            20                  25                  30

Phe Trp Tyr Gln Gln Lys Pro Arg Ser Ser Pro Lys Pro Trp Ile His
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Gln Gln Trp Ser Ser Asn Pro Tyr Thr Phe
                85                  90                  95

Gly Gly Gly Thr Lys Leu Glu Ile Lys Arg
            100                 105

CYTOTOXIC ANTIBODY

FIELD OF THE INVENTION

The present invention relates to antibodies that are cytotoxic to undifferentiated pluripotent cells.

SEQUENCE LISTING

The instant application contains a Sequence Listing which has been submitted electronically in ASCII format and is hereby incorporated by reference in its entirety. Said ASCII copy, created on Dec. 30, 2019, is named 2008187-0151_ST25 and is 8,435 bytes in size.

BACKGROUND TO THE INVENTION

Human embryonic stem cells (hESC) are isolated from the inner cell mass of an early stage human embryo[1-4]. They are distinguished by their ability to replicate indefinitely (self-renewal)[5-8] and under the appropriate conditions differentiate into cells of all three germ layers (ectoderm, endoderm and mesoderm)[4,9,10]. Mounting studies have reported the successful differentiation of hESC into embryoid bodies (EBs)[11] and several lineage-specific cell types, such as cardiomyocytes[12-16], hepatocytes[17], neurons[18-22], endothelial cells[23-28], osteoblasts[29,30], keratinocytes[31] and retinal pigment epithelium (RPE)[32,33]. Their successes demonstrate the great potential of hESC in tissue engineering and regenerative medicine to treat various diseases such as diabetes, heart failures, Parkinson's disease, degenerative eye diseases, and skeletal tissue injuries. However, tumorigenicity, as a major safety concern, is still impeding the progress of hESC-based therapies[34-36]. Briefly, tumorigenicity of hESC refers to the formation of teratomas (benign tumors) or even teratocarcinomas (malignant tumors) in the differentiated cell products due to the presence of residual undifferentiated hESC.

Previously, a panel of monoclonal antibodies (mAbs) has been generated against hESC to characterize hESC populations and discover novel hESC surface markers[37]. See WO2007/102787 and WO2010/033084. Among these antibodies, mAb84 was firstly found to be able to kill undifferentiated hESC. However, since mAb84 is an IgM pentamer, its relatively large molecule size and tendency to form aggregates might impede its penetration efficiency into tumor mass. Subsequently, a smaller antibody fragment format of mAb84, scFv84-HTH, was engineered and demonstrated to have improved penetration by Lim et al.[38]. However, to achieve the same level of cytotoxicity on hESC, the amount of scFv84-HTH required is 20 times more than mAb84. Moreover, since mAb84 and scFv84-HTH are either multivalent or bivalent, the author speculated that antibody cytotoxicity is associated with its valency.

There are several strategies[36,37] to prevent tumorigenicity of hESC, which can be categorized into 3 stages. First, in the pre-transplantation stage, hESC can either be terminally differentiated into the desired cell types or undifferentiated cells can be removed from differentiated cells products by various sorting techniques. Second, in the early post-transplantation stage, tumor progression can be interrupted with methods such as genetic manipulation or cytotoxic drugs. Third, in the late post-transplantation stage, detected tumors carrying an engineered "suicide gene" can be eliminated by drugs. Various techniques to eliminate undifferentiated hESC or tumor formation at different stages, as well as their advantages and disadvantages are summarized in FIG. 1. However, none of these methods is capable of completely precluding teratomas or teratocarcinomas formation in vivo.

Applications of cytotoxic antibodies are diverse. Firstly, cytotoxic antibody-induced cell death can be used as a cell model to study molecule and cellular functions. In 1995, Bazil et al. generated a monoclonal antibody, MEM-59, which recognizes the surface adhesion molecule CD43 of human hematopoietic progenitor cells (HPCs) and directly kill HPCs via cross-linking of CD43[61]. With MEM-59 induced-HPCs death, CD43 was identified as a negative regulator of early hematopoietic events. Secondly, cytotoxic antibodies can be used to identify novel pathways of cell death and to characterize cell death. Matsuoka et al. has generated a monoclonal antibody, RE2, which could induce a novel type of cell death of activated interleukin 2-dependent T cells[62]. Zhang et al. also found a cytotoxic antibody, anti-Porimin, towards Jurkat cells[63]. In this study, they introduced the very first cell surface receptor-mediated pathway of cell death as well as some unique features of cellular response upon cell death, such as cell aggregation, plasma membrane permeabilization and membrane blebs. Thirdly, as mentioned in the previous section, cytotoxic antibodies have been used intensively to eliminate undesired cells, such as the treatment of cancers. Rituximab, a monoclonal antibody targeting the CD20 antigen on B-lymphocytes, was the first cytotoxic antibody approved to treat B-cell malignancies, such as non-Hodgkin's lymphoma, in combination with chemotherapy[64]. Rituximab induces cell death upon hyper-cross linking with goat anti-human secondary antibody after 20 h of incubation. To overcome the rituximab-resistance in some patients, many next-generation anti-CD20 cytotoxic antibodies have been generated[65,66]. GA101 is a novel anti-CD20 cytotoxic antibody, which induces B-lymphocyte death by dispersing lysosomes contents into the cytoplasm and surrounding environment[67]. There are also other cytotoxic antibodies such as RAV12 that induces recurrent adenocarcinoma cell death[68] and anti-NeuGcGM3 antibodies that directly kill lung cancer cells[69,70]. Although all these cytotoxic antibodies can induce cell death, the modes of cell death are varied (FIG. 2).

For a long-time, programmed cell death has been used synonymously with apoptosis and oncosis has been considered as accidental cell death. However, this concept was proved to be not always true[71], where oncosis can also be a pattern of programmed cell death. In fact, every cell may experience "programmed" cell death upon an appropriate stimulus, whereas the pattern (apoptosis or oncosis) differs among cell types and the stimulus[72,73]. In general, cell undergoes three phases upon lethal injuries[72]:
  a) Reversible "pre-mortal phase";
  b) Irreversible cell death, "point-of-no-return";
  c) Post-mortal autolytic and degradative changes.

One way to distinguish different types of cell death and its terminology is to define them by cellular response in each phase of cell death. In the pre-mortal phase, there are two major modes of cell death: apoptosis and oncosis. They are mainly distinguished by cell volume alteration and cellular morphological changes. The hallmarks of apoptosis and oncosis will be discussed in detail later. On the contrary, most of post-mortal cellular changes were termed "necrosis"[72], which is an ancient word describing cellular changes after cell death.

Apoptosis was first proposed by Kerr et al. in 1972 to describe a pattern of controlled cell deletion. In the regulation of normal development and cell population, apoptosis was thought to play a complementary but opposite role to mitosis[74]. Dysregulation of apoptosis would result in many diseases such as cancer, Alzheimer's and autoimmune diseases[75,76].

The process of apoptosis is tightly controlled and organized. It is characterized by a set of morphological changes such as cellular shrinkage, nuclear chromatin condensation and budding of plasma membrane, and biochemical changes such as protein cleavage, cross-linking, patterned DNA fragmentation and phagocytic recognition[77]. Apoptosis usually begins with caspases activation 12 to 24 hours after a trigger event. Changes in plasma membrane protein and cytoskeleton would result in the formation of apoptotic bodies, which enclose fragments of nucleus and cell organelles by intact plasma membrane[74,78]. Subsequently, apoptotic bodies with phosphatidylserine expressed on the outer membrane are recognized and engulfed by the neighboring cells, in particular macrophages and endothelial cells. Eventually, cell debris is cleared out from the tissue to avoid inflammatory response[78]. Generally, there are three major pathways to caspase activation: extrinsic caspase-8 activation via receptor-ligand binding, intrinsic caspase-9 activation via mitochondria and caspase-12 activation via endoplasmic reticulum[79]. To distinguish apoptosis from other modes of cell death, the hallmarks of apoptosis and respective assays are summarized in FIG. 3.

Oncosis was first proposed by Von Rechkling-hausen in 1910 to describe cell death with swelling and later used to describe ischemic cell death distinct from apoptosis[80]. After injury, oncosis can be triggered within seconds to minutes followed by marked cell shape and volume alteration in early stage[72]. It was characterized by several morphological and biochemical changes such as apparent swelling of cell and organelles, gross vacuolization, membrane permeabilization and cytoskeleton proteins degradation[72,80]. Comparing to the understanding of apoptosis, the mechanism of oncosis is still under investigation. Some studies have shown that failure in the ionic pumps of the plasma membrane and decreased levels of cellular ATP might be the cause of oncosis[73,80]. With current understanding, oncosis can be detected by identifying their hallmarks with respective assay, as summarized in FIG. 4A.

In general, apoptosis and oncosis are pre-mortal process, which can lead to post-mortal necrosis. After the phase of apoptosis and oncosis, changes are similar in the phase of necrosis, termed apoptotic necrosis or oncotic necrosis.

As described above, cytotoxic antibodies can induce cell death. Studies on some of these cytotoxic antibodies have shown that cells undergo different modes of cell death (apoptosis or oncosis) upon incubation with cytotoxic antibodies (FIG. 2).

MEM-59 was shown to induce apoptosis in hematopoietic progenitor cells as cell shrinkage and DNA fragmentation were detected[61]. Another antibody, Rituximab, also induces non-Hodgkin's lymphomas apoptosis after 18 to 20 hours incubation. Other detected apoptosis hallmarks including DNA fragmentation, phosphatidylserine exposure detected by Annexin V, and increase in caspase-3 activity[64].

There are also antibodies that induce oncosis in cells. Rapid swelling of RAV12-treated adenocarcinoma cells was observed within 1 hour[81]. Under time-lapse microscopy, membrane damage was detected followed by cell swelling. In addition, disruption of actin cytoskeleton and elevated LDH were also observed upon RAV12 treatment. Another example of antibody-induced oncosis is anti-Porimin[63]. Increase in membrane permeability of anti-Porimin treated Jurkat cells was detected by PI uptake. Moreover, formation of pores on the cells membrane was also visualized under Scanning Electron Microscope (SEM). Another hallmark of anti-Porimin induced oncosis is the re-arrangement of cytoskeletal proteins. A more relevant example is mAb84-induced hESC death via oncosis. Studies have also shown some oncotic features of mAb84-induced hESC death, such as rapid cell death, formation of cell aggregation, loss of membrane integrity and degradation of actin cytoskeleton-associated proteins[82]. However, for all mentioned studies, though the mode of cell death was identified, the detailed mechanism of antibody-induced cell death is still unknown.

WO2012/011876 describes a method of selecting an antibody as a candidate for having cytotoxic activity against a cell which expresses podocalyxin-like protein (PODXL) where the antibody binds PODXL, the method comprising a step of comparing the binding of a PODXL-binding antibody molecule to a glycan comprising Fucα1-2Galβ1-3GlcNAc with the binding of a non-cytotoxic PODXL-binding antibody molecule to a glycan comprising Fucα1-2Galβ1-3GlcNAc.

SUMMARY OF THE INVENTION

In one aspect of the present invention an antibody is provided, the amino acid sequence of the antibody may comprise the amino acid sequences i) to iii), or the amino acid sequences iv) to vi), or preferably the amino acid sequences i) to vi):

```
                                          (SEQ ID NO: 1)
    i) SASSSVSYMF (SEQ ID NO: 2)
   ii) LTSNLAS (SEQ ID NO: 3)
  iii) QQWSSNPYT (SEQ ID NO: 4)
   iv) GFTFSNYYMN (SEQ ID NO: 5)
    v) EIRLKSNNYATHYAESVKG (SEQ ID NO: 6)
   vi) FGY
``` or a variant thereof in which one or two or three amino acids in one or more of the sequences (i) to (vi) are replaced with another amino acid.

The antibody may comprise at least one light chain variable region incorporating the following CDRs:

```
                                          (SEQ ID NO: 1)
         CDR1: SASSSVSYMF (SEQ ID NO: 2)
         CDR2: LTSNLAS (SEQ ID NO: 3)
         CDR3: QQWSSNPYT
```

The antibody may comprise at least one heavy chain variable region incorporating the following CDRs:

```
                                     (SEQ ID NO: 4)
CDR1: GFTFSNYYMN (SEQ ID NO: 5)
CDR2: EIRLKSNNYATHYAESVKG (SEQ ID NO: 6)
CDR3: FGY
```

The antibody may comprise at least one light chain variable region incorporating the CDRs shown in FIG. 15. The antibody may comprise at least one heavy chain variable region incorporating the CDRs shown in FIG. 15.

The antibody may comprise at least one light chain variable region comprising the amino acid sequence shown in FIG. 15 or an amino acid sequence having at least 70%, more preferably one of at least 75%, 80%, 85%, 90%, 95%, 96%, 97%, 98%, 99% or 100%, sequence identity to the $V_L$ chain amino acid sequence of mAb A1 shown in FIG. 15.

The antibody may comprise at least one heavy chain variable region comprising the amino acid sequence shown in FIG. 15 or an amino acid sequence having at least 70%, more preferably one of at least 75%, 80%, 85%, 90%, 95%, 96%, 97%, 98%, 99% or 100%, sequence identity to the $V_H$ chain amino acid sequence of mAb A1 shown in FIG. 15.

The antibody may comprise at least one light chain variable region comprising the amino acid sequence as shown in FIG. 15 (or an amino acid sequence having at least 70%, more preferably one of at least 75%, 80%, 85%, 90%, 95%, 96%, 97%, 98%, 99% or 100%, sequence identity to the $V_L$ chain amino acid sequence of mAb A1 shown in FIG. 15) and at least one heavy chain variable region comprising the amino acid sequence as shown in FIG. 15 (or an amino acid sequence having at least 70%, more preferably one of at least 75%, 80%, 85%, 90%, 95%, 96%, 97%, 98%, 99% or 100%, sequence identity to the $V_H$ chain amino acid sequence of mAb A1 shown in FIG. 15).

The antibody may optionally bind one or more glycosylated proteins, wherein the glycosylation comprises the glycan motif Fucα1-2Galβ1-3GlcNAcβ1-3Galβ1 or Fucα1-2Galβ1-3GlcNAc.

In another aspect of the present invention there is provided an antibody that binds a glycosylated protein, wherein the glycosylation comprises the glycan motif Fucα1-2Galβ1-3GlcNAcβ1-3Galβ1 or Fucα1-2Galβ1-3GlcNAc. The antibody may optionally have amino acid sequence components as described above.

In any aspect of the present invention the antibody is preferably cytotoxic against undifferentiated pluripotent cells. Upon contact with an undifferentiated pluripotent cell it may kill the cell in one of less than 30 minutes, less than 20 minutes, less than 10 minutes, less than 5 minutes, less than 2 minutes or less than 1 minute.

In any aspect of the present invention the antibody preferably specifically binds an undifferentiated pluripotent cell over a cell differentiated from an undifferentiated pluripotent cell. For example, the antibody exhibits specific binding against undifferentiated pluripotent cell(s) over embryoid bodies formed from such cells.

In one aspect of the present invention an isolated heavy chain variable region polypeptide is provided, the heavy chain variable region polypeptide comprising the following CDRs:

```
                                     (SEQ ID NO: 4)
CDR1: GFTFSNYYMN (SEQ ID NO: 5)
CDR2: EIRLKSNNYATHYAESVKG (SEQ ID NO: 6)
CDR3: FGY
```

In one aspect of the present invention an antibody is provided, the antibody comprising a heavy chain and a light chain variable region sequence, wherein:
  the heavy chain comprises a CDR1, CDR2, CDR3, having at least 85% overall sequence identity to CDR1: GFTFSNYYMN (SEQ ID NO: 4), CDR2: EIRLKSNNYATHYAESVKG (SEQ ID NO: 5), CDR3: FGY (SEQ ID NO: 6), and the light chain comprises a CDR1, CDR2, CDR3, having at least 85% overall sequence identity to CDR1: SASSSVSYMF (SEQ ID NO: 1), CDR2: LTSNLAS (SEQ ID NO: 2), CDR3: QQWSSNPYT (SEQ ID NO: 3), respectively.

In some embodiments the degree of sequence identity may be one of 86%, 87%, 88%, 89%, 90%, 91%, 92%, 93%, 94%, 95%, 96%, 97%, 98%, 99%, or 100%.

In another aspect of the present invention an antibody, optionally isolated, is provided comprising a heavy chain and a light chain variable region sequence, wherein:
  the heavy chain sequence has at least 85% sequence identity to the A1H heavy chain sequence shown in FIG. 15A, and
  the light chain sequence has at least 85% sequence identity to the A1L light chain sequence shown in FIG. 15B.

In some embodiments the degree of sequence identity may be one of 86%, 87%, 88%, 89%, 90%, 91%, 92%, 93%, 94%, 95%, 96%, 97%, 98%, 99%, or 100%.

In some embodiments the antibody or polypeptide further comprises variable region heavy chain framework sequences between the CDRs. The framework sequences may be derived from human consensus framework sequences.

In one aspect of the present invention an isolated light chain variable region polypeptide, optionally in combination with a heavy chain variable region polypeptide as described herein, is provided, the light chain variable region polypeptide comprising the following CDRs:

```
                                     (SEQ ID NO: 1)
CDR1: SASSSVSYMF (SEQ ID NO: 2)
CDR2: LTSNLAS (SEQ ID NO: 3)
CDR3: QQWSSNPYT
```

In some embodiments the antibody or polypeptide further comprises variable region light chain framework sequences between the CDRs. The framework sequences may be derived from human consensus framework sequences.

In another aspect of the present invention, a composition, e.g. a pharmaceutical composition or medicament, is provided. The composition may comprise an antibody or polypeptide as described herein and at least one pharmaceutically-acceptable carrier, excipient, adjuvant or diluent.

The antibody may be an IgG. It may have a molecular weight of about 140 to 160 kDa, preferably about 150 kDa.

In some embodiments, preferred antibodies are bivalent.

In some embodiments the antibody may be mAb A1.

Antibody mAb A1 was produced from a hybridoma cell, TAG-A1, which has been deposited with American Type Culture Collection (ATCC), Manassas, Va., USA by Agency for Science, Technology and Research, 1 Fusionoplois Way, #20-10 Connexis, Singapore 138632 on 20 Mar. 2014 under accession number PTA-121134 in accordance with the provisions of the Budapest Treaty.

Accordingly, a hybridoma cell line TAG-A1, deposited with American Type Culture Collection under Accession Number PTA-121134 is provided. A monoclonal antibody produced from hybridoma cell line TAG-A1, deposited with American Type Culture Collection under Accession Number PTA-121134 is provided.

The antibody preferably exhibits specific binding towards more than one glycosylated protein antigen, particularly glycosylated protein antigens present in, or on, undifferentiated pluripotent cells, wherein the glycosylation on the protein antigens comprises the glycan motif Fucα1-2Galβ1-3GlcNAcβ1-3Galβ1 or Fucα1-2Galβ1-3GlcNAc. This motif may optionally be present as part of a larger glycan or may represent the complete glycan. The glycan may preferably be O-linked to the protein.

The pluripotent cells may express one or more glycosylated proteins having the glycan motif Fucα1-2Galβ1-3GlcNAcβ1-3Galβ1 or Fucα1-2Galβ1-3GlcNAc either in the cell and/or on the cell surface. In this specification undifferentiated pluripotent cells may be undifferentiated pluripotent stem cells. Preferably, they are human or mammalian.

In another aspect of the present invention an isolated nucleic acid encoding an antibody or polypeptide as described herein is provided.

In one aspect of the present invention there is provided a vector comprising a nucleic acid described herein. In another aspect of the present invention, there is provided a host cell comprising the vector. For example, the host cell may be eukaryotic, or mammalian, e.g. Chinese Hamster Ovary (CHO), or human or may be a prokaryotic cell, e.g. *E. coli*.

In one aspect of the present invention a method for making an antibody or polypeptide as described herein is provided, the method comprising culturing a host cell as described herein under conditions suitable for the expression of a vector encoding the antibody or polypeptide, and recovering the antibody or polypeptide.

In another aspect of the present invention there is provided a method of destroying an undifferentiated pluripotent cell or cells in a sample containing such cells, the method comprising contacting a sample of cells containing an undifferentiated pluripotent cell or cells with an antibody according to the present invention.

In another aspect of the present invention there is provided a method of removing an undifferentiated pluripotent cell or cells from a sample containing such cells, the method comprising contacting a sample of cells containing an undifferentiated pluripotent cell or cells with an antibody according to the present invention.

In another aspect of the present invention there is provided a method of enriching pluripotent cells that have undergone or are undergoing differentiation from a mixture comprising undifferentiated pluripotent cells and such cells that have undergone or are undergoing differentiation, the method comprising contacting the mixture with an antibody according to the present invention for a period of time sufficient for the antibody to kill undifferentiated pluripotent cells. The method may further comprise the step of separating live cells from dead cells.

In another aspect of the present invention there is provided a method of preparing a composition containing cells differentiated from undifferentiated pluripotent cells which composition contains substantially no undifferentiated pluripotent cells, the method comprising:
  (i) providing a population of cells comprising undifferentiated pluripotent cells and cells differentiated from undifferentiated pluripotent cells;
  (ii) contacting the population with an antibody according to the present invention under conditions permitting the antibody to kill undifferentiated pluripotent cells; and
  (iii) separating live cells remaining after step (ii) from dead cells.

The method may further comprise mixing the separated cells from (iii) with a pharmaceutically acceptable carrier, adjuvant or diluent.

In another aspect of the present invention there is provided an in vitro complex comprising an undifferentiated pluripotent cell bound to an antibody according to the present invention. The complex may be isolated.

Methods according to the present invention may preferably be performed in vitro. The methods may comprise incubating cells and antibody together for a predetermined period of time sufficient for the antibody to exert a cytotoxic effect. Such period of time may be one of at least 1 minute, at least 2 minutes, at least 5 minutes, at least 10 minutes, at least 20 minutes, at least 30 minutes, at least 40 minutes, at least 50 minutes, or at least 60 minutes.

In another aspect of the present invention a method of treating a patient in need of cell therapy is provided, the method comprising administering to the patient a composition containing cells differentiated from undifferentiated pluripotent cells which composition contains substantially no undifferentiated pluripotent cells, wherein the composition is obtained by a method described herein.

The use of cells differentiated from undifferentiated pluripotent cells obtained by a method described herein in the manufacture of a medicament for treating a patient in need of cell therapy is also provided.

A cell or cells differentiated from undifferentiated pluripotent cells and obtained by a method described herein is also provided for use in treating a patient in need of cell therapy.

DESCRIPTION

Antibodies

Antibodies according to the present invention preferably to a glycan comprising the glycan motif Fucα1-2Galβ1-3GlcNAcβ1-3Galβ1 or Fucα1-2Galβ1-3GlcNAc, or to a glycosylated protein, wherein the glycosylation comprises the glycan motif Fucα1-2Galβ1-3GlcNAcβ1-3Galβ1 or Fucα1-2Galβ1-3GlcNAc.

In some embodiments, antibodies according to the present invention bind to a glycan or glycosylated protein comprising the glycan motif Fucα1-2Galβ1-3(Fucα1-4)GlcNAc.

In some embodiments, antibodies according to the present invention bind to a glycan or glycosylated protein comprising the glycan motif (Fucα1-2)Galβ1-3GlcNAcβ1-3Galβ1-4Glc.

In some embodiments, antibodies according to the present invention bind to a glycan or glycosylated protein comprising the glycan motif Fucα1-2Galβ1-3GlcNAc.

The antibodies are preferably cytotoxic against undifferentiated pluripotent cells. Upon contact with an undifferentiated pluripotent cell an antibody according to the present invention may kill the cell in one of less than 30 minutes, less than 20 minutes, less than 10 minutes, less than 5 minutes, less than 2 minutes or less than 1 minute.

Cytotoxicity of the antibody against undifferentiated pluripotent cells is preferably time- and dosage-dependent. The antibody preferably induces cell death via oncosis, and preferably not via apoptosis.

Antibody treated undifferentiated pluripotent cells preferably exhibit morphological changes, such as loss of membrane microvilli, formation of membrane pores, cell swelling, mitochondria enrichment and peripheral relocalization, destruction of actin-cytoskeleton and exposure of nucleus.

Preferably, the antibody specifically binds an undifferentiated pluripotent cell (parent pluripotent cell) over a cell differentiated from an undifferentiated pluripotent cell (differentiated progeny cell). For example, the antibody exhibits specific binding against undifferentiated pluripotent cell(s) over embryoid bodies formed from such cells.

Antibodies according to the present invention may be provided in isolated form.

By "antibody" we include a fragment or derivative thereof, or a synthetic antibody or synthetic antibody fragment.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen. Thus, mAbs binding glycosylated proteins having the glycan motif Fucα1-2Galβ1-3GlcNAcβ1-3Galβ1 or Fucα1-2Galβ1-3GlcNAc can potentially be used to purify or eliminate subsets of viable cells exhibiting a repertoire of antigens that characterizes undifferentiated cells or cells differentiating into a specific lineage.

Polyclonal antibodies are useful in the methods of the invention. Monospecific polyclonal antibodies are preferred. Suitable polyclonal antibodies can be prepared using methods well known in the art.

Fragments of antibodies, such as Fab and $Fab_2$ fragments may also be used as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from E. coli, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site. Synthetic antibodies which bind to glycosylated proteins having the glycan motif Fucα1-2Galβ1-3GlcNAcβ1-3Galβ1 or Fucα1-2Galβ1-3GlcNAc may also be made using phage display technology as is well known in the art.

In certain methods, the antibody is mAb A1, or a variant of mAb A1. mAb A1 comprises the following CDR sequences:

```
Light chain:
                                             (SEQ ID NO: 1)
     i) SASSSVSYMF (SEQ ID NO: 2)
    ii) LTSNLAS (SEQ ID NO: 3)
   iii) QQWSSNPYT Heavy chain:
                                             (SEQ ID NO: 4)
    iv) GFTFSNYYMN (SEQ ID NO: 5)
     v) EIRLKSNNYATHYAESVKG (SEQ ID NO: 6)
    vi) FGY
```

CDR sequences determined by Chothia/AbM definition.

Antibodies according to the present invention may comprise the CDRs of mAb A1. In an antibody according to the present invention one or two or three or four of the sequences (i) to (vi) may vary. A variant may have one or two amino acid substitutions in one or two of the sequences (i) to (vi).

The amino acid sequence (and encoding polynucleotide sequence) of the $V_H$ and $V_L$ chains of mAb A1 have been determined as shown in FIG. 15.

The light and heavy chain CDRs 1-3 of mAb A1 may also be particularly useful in conjunction with a number of different framework regions. Accordingly, light and/or heavy chains having CDRs 1-3 of mAb A1 may possess an alternative framework region. Suitable framework regions are well known in the art and are described for example in M. Lefranc & G. Le:franc (2001) "The Immunoglobulin FactsBook", Academic Press, incorporated herein by reference.

In this specification, antibodies may have $V_H$ and/or VL chains comprising an amino acid sequence that has a high percentage sequence identity to the mAb A1 $V_H$ and/or $V_L$ amino acid sequences of FIG. 15.

For example, antibodies according to the present invention include antibodies that bind the glycan motif Fucα1-2Galβ1-3GlcNAcβ1-3Galβ1 or Fucα1-2Galβ1-3GlcNAc (preferably a glycoslated protein having the glycan motif Fucα1-2Galβ1-3GlcNAcβ1-3Galβ1 or Fucα1-2Galβ1-3GlcNAc) and have a $V_H$ chain that comprises an amino acid sequence having at least 70%, more preferably one of at least 75%, 80%, 85%, 90%, 95%, 96%, 97%, 98%, 99% or 100%, sequence identity to the $V_H$ chain amino acid sequence of mAb A1 shown in FIG. 15.

Antibodies according to the present invention include antibodies that bind the glycan motif Fucα1-2Galβ1-3GlcNAcβ1-3Galβ1 or Fucα1-2Galβ1-3GlcNAc (preferably a glycoslated protein having the glycan motif Fucα1-2Galβ1-3GlcNAcβ1-3Galβ1 or Fucα1-2Galβ1-3GlcNAc) and have a $V_L$ chain that comprises an amino acid sequence having at least 70%, more preferably one of at least 75%, 80%, 85%, 90%, 95%, 96%, 97%, 98%, 99% or 100%, sequence identity to the $V_L$ chain amino acid sequence of mAb A1 shown in FIG. 15.

Antibodies according to the present invention may be used to eliminate residual undifferentiated pluripotent cells after differentiation and optionally prior to animal transplantation trials to test the function of the differentiated cells.

Antibodies according to the present invention (optionally in combination with other mAbs as described in WO 2007/102787) may be used prior to transplantation to eliminate residual undifferentiated hESC or undifferentiated induced pluripotent stem cells, thus increasing the success and safety of the graft in regenerative clinical applications.

Antibodies according to the present invention can potentially be used to eliminate subsets of viable cells exhibiting a repertoire of antigens that characterizes undifferentiated pluripotent cells.

Antibodies according to the present invention may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabelled antibody which can be detected by another antibody which is itself labelled. Alternatively, the second antibody may have bound to it biotin and binding of labelled streptavidin to the biotin is used to indirectly label the first antibody.

Methods

Methods according to the present invention may comprise:
(a) isolating cells differentiated from pluripotent cells from the parent undifferentiated pluripotent cells;
(b) separating cells differentiated from pluripotent cells from the parent undifferentiated pluripotent cells;
(c) enriching cells differentiated from pluripotent cells from the parent undifferentiated pluripotent cells;
(d) preparing a composition of cells differentiated from pluripotent cells, which composition has substantially no undifferentiated pluripotent cells.

Each method may comprise contacting a sample containing undifferentiated pluripotent cells (parent pluripotent cells) and cells differentiated from the parent pluripotent cells (differentiated progeny cells) with an antibody according to the present invention for a period of time sufficient for the antibody to exert its cytotoxic effect and kill undifferentiated pluripotent cells contained in the sample. Preferably, the amount of antibody used and period of time is sufficient for all, or substantially all, undifferentiated cells in the sample to be killed leaving a sample that is a purified population of differentiated progeny cells. Sufficient time may, for example, be one of at least 1 minute, at least 2 minutes, at least 5 minutes, at least 10 minutes, at least 20 minutes, at least 30 minutes, at least 40 minutes, at least 60 minutes, 90 minutes or longer than 2 hours.

Contacting of the antibody and cells may be under conditions suitable to permit binding of the antibody to glycosylated protein antigens present in the sample. Such conditions are well known to those of ordinary skill in the art, for example comprising physiological pH and physiological buffer.

Methods according to the present invention may comprise the step of partitioning, removing, isolating, separating, purifying or enriching cells not killed by the antibody.

Methods according to the present invention may comprise the step of destroying cells bound by the antibody. Methods according to the present invention may further comprise the step of quantifying cells that have been partitioned, removed, isolated, separated, purified, or enriched.

In methods of the present invention the antibody may be immobilised on, e.g. conjugated to, a solid support so that the undifferentiated pluripotent cell(s) can be bound by affinity binding. Conveniently, the solid support comprises any suitable matrix such as agarose, acrylamide, Sepharose™ and Sephadex™. The solid support may be a solid substrate such as a microtitre plate or chip, or a column.

In some embodiments the antibody is magnetically labelled (either directly or indirectly) such that, when bound, the undifferentiated pluripotent cell(s) can be separated from the rest of the sample upon provision of a suitable magnetic field. Microbeads used for magnetic cell sorting are often termed MACS colloidal super paramagnetic microbeads. Undifferentiated pluripotent cells labelled in this way may be sorted by magnetic activated cell sorting (MACS).

Other methods of separating cells which comprise a specific cellular marker are known in the art and include FACS (Fluorescence Activated Cell Sorting) for which the antibody is labelled with a fluorescent molecule.

Methods according to the present invention may comprise the step of culturing the differentiated progeny cells which have been partitioned, removed, isolated, separated, purified, or enriched.

Methods according to the present invention may be used to provide an enriched or substantially isolated composition of differentiated progeny cells. Such a composition may be used in various ways, for example it may be used in cell therapy or it may be used as a source of cells which are then encouraged to differentiate (by continued or further differentiation) into a particular cell lineage which is useful for a particular therapy, or it may be used to investigate (in vitro or in vivo) the factors which allow for the cell to differentiate into other cells.

Typically, the enriched composition of differentiated progeny cells contains at least 50% of the cells as differentiated progeny cells, preferably at least 70% or at least 90% or at least 95%. Preferably, all of the cells in the composition are the said differentiated progeny cells.

Methods for enriching a population of cells preferably involve increasing the concentration of the cells in the sample or increasing the population of cells (i.e. number of cells of a given type), either absolutely or relative to the number of other cells in the sample.

The invention also provides methods of destroying an undifferentiated pluripotent cell or cells, the method comprising contacting undifferentiated pluripotent cell(s) with an antibody of the present invention.

In some methods, the antibody mediates cell death by an oncosis mechanism, which is a form of cell death resulting from membrane damage leading to an increase in cell permeability (as evidenced by permeability to dyes such as propidium iodide/trypan blue) and cell shrinkage. Cell death induced by the methods of the invention may be preceded by poration of the cell membrane, blebbing and/or cell clumping.

Methods for destroying undifferentiated pluripotent cells may be used to remove undifferentiated pluripotent cells from a cell population that has been induced to differentiate. Methods for destroying undifferentiated pluripotent cells may be used prior to transplantation of tissues or organs to eliminate residual IPSCs, thus increasing the success and safety of the graft, particularly by reducing the risk of teratoma formation.

Methods according to the present invention are preferably performed in vitro. The term "in vitro" is intended to encompass experiments with cells in culture whereas the term "in vivo" is intended to encompass experiments with intact multi-cellular organisms.

Kits

According to some aspects of the present invention a kit of parts is provided comprising an antibody according to the present invention.

The kit may further comprise an agent capable of detecting a marker of pluripotency. The marker may be one or more of Oct4, SSEA-4, Tra-1-60, Tra-1-81 and GCTM-2. The agent may be antibody that binds to such a marker, e.g. one of mAb 5, mAb 8, mAb 14, mAb 63, mAb 84, mAb 85, mAb 95, mAb 375, mAb 432, mAb 529.

In some embodiments, the kit comprises an antibody according to the present invention and an antibody to one or more of Oct4, SSEA-4, Tra-1-60, Tra-1-81 and GCTM-2. Typically, the kit may also contain one or more of: reagents for use in immunochemistry; the antibodies immobilised to a solid support; means for labelling the antibodies; means for linking the antibodies to a cytotoxic moiety.

Sample

Some methods of the present invention involve a sample containing cells. The sample may be any quantity of cells which contains, or is suspected of containing, one or more undifferentiated pluripotent cells. The sample may be a culture of cells grown in vitro. For example, the culture may comprise a suspension of cells or cells cultured in a culture plate or dish.

In preferred embodiments the sample contains undifferentiated pluripotent cells. In some embodiments the sample contains undifferentiated pluripotent cells and pluripotent cells that have undergone differentiation or are undergoing differentiation. Pluripotent cells that have undergone differentiation or are undergoing differentiation may no longer be pluripotent and are preferably not bound by an antibody according to the present invention.

The sample may be one in which undifferentiated pluripotent cells have been encouraged (or promoted) to differentiate into an embryoid body or into particular cell lineages and therefore the sample may contain a mixture of undifferentiated and differentiated cells (because differentiation is often not an efficient process). Typically in such a sample the undifferentiated pluripotent cells constitute a few percent of the total number of cells. Typically, the differentiated cells in the sample may one or more of ectoderm, endoderm, mesoderm (representing the three primary lineages of differentiated cell), cardiomyocytes, pancreatic islets, neuronal progenitor cells or mesenchymal stem cells which are derived (by differentiation) from the pluripotent cells. Removal (or destruction) of the undifferentiated pluripotent cells from (or in) such a sample will be useful prior to the clinical application of the sample which contains differentiated cells because, potentially, the undifferentiated pluripotent cells can form undesirable teratomas. Typically, in methods of the present invention at least 95% of the undifferentiated pluripotent cells are removed, partitioned or destroyed. Preferably, all of the said cells are removed, partitioned or destroyed.

Stem Cells

The term "stem cell" generally refers to a cell that on division faces two developmental options: the daughter cells can be identical to the original cell (self-renewal) or they may be the progenitors of more specialised cell types (differentiation). The stem cell is therefore capable of adopting one or other pathway (a further pathway exists in which one of each cell type can be formed). Stem cells are therefore cells which are not terminally differentiated and are able to produce cells of other types.

Pluripotent Stem Cells

Pluripotent stem cells are true stem cells, with the potential to make any differentiated cell in the body, but not an entire organism. They cannot contribute to making the extraembryonic membranes which are derived from the trophoblast. Several types of pluripotent stem cells are known, including embryonic stem cells and induced pluripotent stem cells.

In the present specification an undifferentiated pluripotent cell may be an undifferentiated pluripotent stem cell.

Pluripotent stem cells may be derived from rabbit, guinea pig, rat, mouse or other rodent, cat, dog, pig, sheep, goat, cattle, horse, non-human primate or other non-human vertebrate organism. In preferred embodiments the pluripotent stem cells are human.

Embryonic Stem Cells

Embryonic Stem (ESCs) cells may be isolated from the inner cell mass (ICM) of the blastocyst, which is the stage of embryonic development when implantation occurs.

In the present application embryonic stem cells may be derived from rabbit, guinea pig, rat, mouse or other rodent, cat, dog, pig, sheep, goat, cattle, horse, non-human primate or other non-human vertebrate organism. In preferred embodiments the embryonic stem cells are human.

Embryonic stem cells may be obtained from the blastocyst, although in some embodiments the present invention does not encompass embryonic stem cells (particularly human) obtained by a method causing destruction of an embryo.

Induced Pluripotent Stem Cells

Induced pluripotent stem cells, commonly abbreviated as iPS cells or iPSCs, are a type of pluripotent stem cell artificially derived from a non-pluripotent cell, typically an adult somatic cell, by inserting certain genes. iPS cells are reviewed and discussed in Takahashi, K. & Yamanaka (2006), Yamanaka S, et. al. (2007), Wernig M, et. al. (2007), Maherali N, et. al. (2007), Yu J, et al. (2007) and Takahashi et al., (2007), all of which are incorporated herein by reference.

iPS cells are typically derived by transfection of certain stem cell-associated genes into non-pluripotent cells, such as adult fibroblasts. Transfection is typically achieved through viral vectors, for example through retroviral reprogramming. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic infection.

IPSCs may be induced from somatic cells such as fibroblasts by transfection with one or more transcription factors. In some cases, cells are transformed with Oct3/4, Sox2, c-Myc and Klf4. The cells may be additionally transfected with other genes, including transcription factors and/or marker genes. The genes may be introduced using a transposon system such as the Cre/loxP recombination system, or using non-integrating vectors in order to produce iPSCs free of exogenous reprogramming genes. Transfection may be achieved using viral vectors, such as a retrovirus. The virus may be an amphotropic virus. Once the cells have been transfected, they may be grown on feeder cells before transfer to an ESC culture medium.

The IPSCs may be derived from rabbit, guinea pig, rat, mouse or other rodent, cat, dog, pig, sheep, goat, cattle, horse, non-human primate or other non-human vertebrate organism. In preferred embodiments the IPSCs are derived from human cells.

iPS cells useful in the invention may be derived from any suitable cell type, including lung, foreskin fibroblasts, skin fibroblasts, keratinocytes, blood progenitor cells, bone marrow cells, hepatocytes, gastric epithelial cells, pancreatic cells, neural stem cells, B lymphocytes, ES derived somatic cells and embryonic fibroblasts. The iPS cells may be derived from human, mouse or other mammals. Preferably, the iPS cells are human. In some cases, the cells are not human dermal fibroblasts. The IPSCs may exhibit similar patterns of gene expression and phenotype to ESCs.

Like ESCs, future therapeutic applications of differentiated induced pluripotent stem cells carry a risk of teratoma formation by contaminating residual undifferentiated IPSC. Despite this problem, currently there are not many strategies developed to separate these cell populations.

Multipotent Stem Cells

Multipotent stem cells are true stem cells but can only differentiate into a limited number of types. For example, the bone marrow contains multipotent stem cells that give rise to all the cells of the blood but not to other types of cells. Multipotent stem cells are found in adult animals. It is thought that every organ in the body contains them where they can replace dead or damaged cells.

Methods of characterising stem cells are known in the art, and include the use of standard assay methods such as clonal assay, flow cytometry, long-term culture and molecular biological techniques e.g. PCR, RT-PCR and Southern blotting.

Adult Stem Cells

Adult stem cells comprise a wide variety of types including neuronal, skin and the blood forming stem cells which are the active component in bone marrow transplantation.

These latter stem cell types are also the principal feature of umbilical cord-derived stem cells. Adult stem cells can mature both in the laboratory and in the body into functional, more specialised cell types although the exact number of cell types is limited by the type of stem cell chosen.

Culture of Stem Cells

Any suitable method of culturing stem cells may be used in the methods and compositions described here.

Any suitable container may be used to propagate stem cells according to the methods and compositions described here. Suitable containers include those described in US Patent Publication US2007/0264713 (Terstegge).

Containers may include bioreactors and spinners, for example. A "bioreactor", as the term is used in this document, is a container suitable for the cultivation of eukaryotic cells, for example animal cells or mammalian cells, such as in a large scale. A typical cultivation volume of a regulated bioreactor is between 20 ml and 500 ml.

The bioreactor may comprise a regulated bioreactor, in which one or more conditions may be controlled or monitored, for example, oxygen partial pressure. Devices for measuring and regulating these conditions are known in the art. For example, oxygen electrodes may be used for oxygen partial pressure. The oxygen partial pressure can be regulated via the amount and the composition of the selected gas mixture (e.g., air or a mixture of air and/or oxygen and/or nitrogen and/or carbon dioxide). Suitable devices for measuring and regulating the oxygen partial pressure are described by Bailey, J E. (Bailey, J E., Biochemical Engineering Fundamentals, second edition, McGraw-Hill, Inc. ISBN 0-07-003212-2 Higher Education, (1986)) or Jackson A T. Jackson A T., Verfahrenstechnik in der Biotechnologie, Springer, ISBN 3540561900 (1993)).

Other suitable containers include spinners. Spinners are regulated or unregulated bioreactors, which can be agitated using various agitator mechanisms, such as glass ball agitators, impeller agitators, and other suitable agitators. The cultivation volume of a spinner is typically between 20 ml and 500 ml. Roller bottles are round cell culture flasks made of plastic or glass having a culture area of between 400 and 2000 $cm^2$. The cells are cultivated along the entire inner surface of these flasks; the cells are coated with culture medium accomplished by a "rolling" motion, i.e. rotating the bottles about their own individual axis.

Alternatively, culture may be static, i.e. where active agitation of the culture/culture media is not employed. By reducing agitation of the culture, aggregates of cells may be allowed to form. Whilst some agitation may be employed to encourage distribution and flow of the culture media over the cultured cells this may be applied so as not to substantially disrupt aggregate formation. For example, a low rpm agitation, e.g. less than 30 rpm or less than 20 rpm, may be employed.

Propagation with Passage

The methods and compositions described here may comprise passaging, or splitting during culture. The methods may involve continuous or continual passage.

By "continual" or "continuous", we mean that our methods enable growth of stem cells in a fashion that enables them to be passaged, e.g., taken off the plates or microcarriers on which they are growing and transferred to other plates, microcarriers or particles, and that this process may be repeated at least once, for example twice, three times, four times, five times, etc. In some cases, this may be repeated any number of times, for example indefinitely or infinitely.

Cells in culture may be dissociated from the substrate or flask, and "split", subcultured or passaged, by dilution into tissue culture medium and replating.

Cells growing on particles may be passaged back onto particle culture. Alternatively, they may be passaged back onto conventional (2D) cultures. Tissue culture cells growing on plates may be passaged onto particle culture.

The term "passage" may generally refer to the process of taking an aliquot of a cell culture, dissociating the cells completely or partially, diluting and inoculating into medium. The passaging may be repeated one or more times. The aliquot may comprise the whole or a portion of the cell culture. The cells of the aliquot may be completely, partially or not confluent. The passaging may comprise at least some of the following sequence of steps: aspiration, rinsing, trypsinization, incubation, dislodging, quenching, re-seeding and aliquoting. The protocol published by the Hedrick Lab, UC San Diego may be used (http://hedricklab.ucsd.edu/Protocol/COSCell.html).

The cells may be dissociated by any suitable means, such as mechanical or enzymatic means known in the art. The cells may be broken up by mechanical dissociation, for example using a cell scraper or pipette. The cells may be dissociated by sieving through a suitable sieve size, such as through 100 micron or 500 micron sieves. The cells may be split by enzymatic dissociation, for example by treatment with collagenase or trypLE harvested. The dissociation may be complete or partial.

The dilution may be of any suitable dilution. The cells in the cell culture may be split at any suitable ratio. For example, the cells may be split at a ratio of 1:2 or more, 1:3 or more, 1:4 or more or 1:5 or more. Thus, stem cells may be passaged for 1 passage or more. For example, stem cells may be passaged for 2, 3, 4, 5, 6, 7, 8, 9, 10, 11, 12, 13, 14, 15, 16, 17, 18, 19, 20, 21, 22, 23, 24, 25 passages or more. Passages may be expressed as generations of cell growth. Our methods and compositions allow stem cells to propagate for 1, 2, 3, 4, 5, 6, 7, 8, 9, 10, 11, 12, 13, 14, 15, 16, 17, 18, 19, 20, 21, 22, 23, 24, 25 generations or more.

Passages may also be expressed as the number of cell doublings. Our methods and compositions allow stem cells to propagate for 1, 2, 3, 4, 5, 6, 7, 8, 9, 10, 11, 12, 13, 14, 15, 16, 17, 18, 19, 20, 21, 22, 23, 24, 25 cell doublings or more.

Maintenance of Stem Cell Characteristics

The propagated stem cells may retain at least one characteristic of the parent stem cell. The stem cells may retain the characteristic after one or more passages. They may do so after a plurality of passages. They may do so after the stated number of passages as described above.

The characteristic may comprise a morphological characteristic, immunohistochemical characteristic, a molecular biological characteristic, etc. The characteristic may comprise a biological activity.

Stem Cell Characteristics

The stem cells propagated by our methods may display any of the following stem cell characteristics.

Stem cells may display increased expression of Oct4 and/or SSEA-1 and/or TRA-1-60. Stem cells which are self-renewing may display a shortened cell cycle compared to stem cells which are not self-renewing.

Stem cells may display defined morphology. For example, in the two dimensions of a standard microscopic image, human embryonic stem cells display high nuclear/cytoplasmic ratios in the plane of the image, prominent nucleoli, and compact colony formation with poorly discernable cell junctions.

Stem cells may also be characterized by expressed cell markers as described in further detail below.

Expression of Pluripotency Markers

The biological activity that is retained may comprise expression of one or more pluripotency markers.

Stage-specific embryonic antigens (SSEA) are characteristic of certain embryonic cell types. Antibodies for SSEA markers are available from the Developmental Studies Hybridoma Bank (Bethesda Md.). Other useful markers are detectable using antibodies designated Tra-1-60 and Tra-1-81 (Andrews et al., Cell Lines from Human Germ Cell Tumors, in E. J. Robertson, 1987, supra). Human embryonic stem cells are typically SSEA-1 negative and SSEA-4 positive. hEG cells are typically SSEA-1 positive. Differentiation of primate pluripotent stem cells (pPS) cells in vitro results in the loss of SSEA-4, Tra-1-60, and Tra-1-81 expression and increased expression of SSEA-1. pPS cells can also be characterized by the presence of alkaline phosphatase activity, which can be detected by fixing the cells with 4% paraformaldehyde, and then developing with Vector Red as a substrate, as described by the manufacturer (Vector Laboratories, Burlingame Calif.).

Embryonic stem cells are also typically telomerase positive and OCT-4 positive. Telomerase activity can be determined using TRAP activity assay (Kim et al., Science 266:2011, 1997), using a commercially available kit (TRAPeze.®. XK Telomerase Detection Kit, Cat. s7707; Intergen Co., Purchase N.Y.; or TeloTAGGG.™. Telomerase PCR ELISA plus, Cat. 2,013,89; Roche Diagnostics, Indianapolis). hTERT expression can also be evaluated at the mRNA level by RT-PCR. The LightCycler TeloTAGGG™ hTERT quantification kit (Cat. 3,012,344; Roche Diagnostics) is available commercially for research purposes.

Any one or more of these pluripotency markers, including FOXD3, PODXL, alkaline phosphatase, OCT-4, SSEA-4, TRA-1-60 and Mab84, etc, may be retained by the propagated stem cells.

Detection of markers may be achieved through any means known in the art, for example immunologically. Histochemical staining, flow cytometry (FACS), Western Blot, enzyme-linked immunoassay (ELISA), etc may be used.

Flow immunocytochemistry may be used to detect cell-surface markers. immunohistochemistry (for example, of fixed cells or tissue sections) may be used for intracellular or cell-surface markers. Western blot analysis may be conducted on cellular extracts. Enzyme-linked immunoassay may be used for cellular extracts or products secreted into the medium.

For this purpose, antibodies to the pluripotency markers as available from commercial sources may be used.

Antibodies for the identification of stem cell markers including the Stage-Specific Embryonic Antigens 1 and 4 (SSEA-1 and SSEA-4) and Tumor Rejection Antigen 1-60 and 1-81 (TRA-1-60, TRA-1-81) may be obtained commercially, for example from Chemicon International, Inc (Temecula, Calif., USA). The immunological detection of these antigens using monoclonal antibodies has been widely used to characterize pluripotent stem cells (Shamblott M. J. et. al. (1998) PNAS 95: 13726-13731; Schuldiner M. et. al. (2000). PNAS 97: 11307-11312; Thomson J. A. et. al. (1998). Science 282: 1145-1147; Reubinoff B. E. et. al. (2000). Nature Biotechnology 18: 399-404; Henderson J. K. et. al. (2002). Stem Cells 20: 329-337; Pera M. et. al. (2000). J. Cell Science 113: 5-10.).

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. Sequence data for the particular markers listed in this disclosure can be obtained from public databases such as GenBank (URL www.ncbi.nlm.nih.gov:80/entrez). See U.S. Pat. No. 5,843,780 for further details.

Substantially all of the propagated cells, or a substantial portion of them, may express the marker(s). For example, the percentage of cells that express the marker or markers may be 50% or more, 60% or more, 70% or more, 80% or more, 90% or more, 93% or more, 95% or more, 97% or more, 98% or more, 99% or more, or substantially 100%.

Cell Viability

The biological activity may comprise cell viability after the stated number of passages. Cell viability may be assayed in various ways, for example by Trypan Blue exclusion.

A protocol for vital staining follows. Place a suitable volume of a cell suspension (20-200 µL) in appropriate tube add an equal volume of 0.4% Trypan blue and gently mix, let stand for 5 minutes at room temperature. Place 10 µl of stained cells in a hemocytometer and count the number of viable (unstained) and dead (stained) cells. Calculate the average number of unstained cells in each quadrant, and multiply by $2 \times 10^4$ to find cells/ml. The percentage of viable cells is the number of viable cells divided by the number of dead and viable cells.

The viability of cells may be 50% or more, 60% or more, 70% or more, 80% or more, 90% or more, 93% or more, 95% or more, 97% or more, 98% or more, 99% or more, or substantially 100%.

Karyotype

The propagated stem cells may retain a normal karyotype during or after propagation. A "normal" karyotype is a karyotype that is identical, similar or substantially similar to a karyotype of a parent stem cell from which the stem cell is derived, or one which varies from it but not in any substantial manner. For example, there should not be any gross anomalies such as translocations, loss of chromosomes, deletions, etc.

Karyotype may be assessed by a number of methods, for example visually under optical microscopy. Karyotypes may be prepared and analyzed as described in McWhir et al. (2006), Hewitt et al. (2007), and Gallimore and Richardson (1973). Cells may also be karyotyped using a standard G-banding technique (available at many clinical diagnostics labs that provide routine karyotyping services, such as the Cytogenetics Lab at Oakland Calif.) and compared to published stem cell karyotypes.

All or a substantial portion of propagated cells may retain a normal karyotype. This proportion may be 50% or more, 60% or more, 70% or more, 80% or more, 90% or more, 93% or more, 95% or more, 97% or more, 98% or more, 99% or more, or substantially 100%.

Pluripotency

The propagated stem cells may retain the capacity to differentiate into all three cellular lineages, i.e., endoderm, ectoderm and mesoderm. Methods of induction of stem cells to differentiate each of these lineages are known in the art and may be used to assay the capability of the propagated stem cells. All or a substantial portion of propagated cells may retain this ability. This may be 50% or more, 60% or more, 70% or more, 80% or more, 90% or more, 93% or more, 95% or more, 97% or more, 98% or more, 99% or more, or substantially 100% of the propagated stem cells.

The pluripotency of the generated stem cells may be determined by use of suitable assays. Such assays may comprise detecting one or more markers of pluripotency, e.g. SSEA-1 antigen, alkaline phosphatase activity, detection of Oct-4 gene and/or protein expression, by observing the extent of teratoma formation in SCID mice or formation of embryoid bodies. Pluripotency of hESC may be defined by the expression of one or more markers such as Oct-4, SSEA-4, Tra-1-60, Tra-1-81, SOX-2 and GCTM-2.

Co-Culture and Feeders

Methods may comprise culturing stem cells in the presence or absence of co-culture. The term "co-culture" refers to a mixture of two or more different kinds of cells that are grown together, for example, stromal feeder cells. The two or more different kinds of cells may be grown on the same surfaces, such as particles or cell container surfaces, or on different surfaces. The different kinds of cells may be grown on different particles.

Feeder cells, as the term is used in this document, may mean cells which are used for or required for cultivation of cells of a different type. In the context of stem cell culture, feeder cells have the function of securing the survival, proliferation, and maintenance of cell pluripotency. Cell pluripotency may be achieved by directly co-cultivating the feeder cells. Alternatively, or in addition, the feeder cells may be cultured in a medium to condition it. The conditioned medium may be used to culture the stem cells.

The inner surface of the container such as a culture dish may be coated with a feeder layer of mouse embryonic skin cells that have been treated so they will not divide. The feeder cells release nutrients into the culture medium which are required for ES cell growth. The stem cells growing on particles may therefore be grown in such coated containers.

Arrangements in which feeder cells are absent or not required are also possible. For example, the cells may be grown in medium conditioned by feeder cells or stem cells.

Media and Feeder Cells

Media for isolating and propagating pluripotent stem cells can have any of several different formulas, as long as the cells obtained have the desired characteristics, and can be propagated further.

Suitable sources are as follows: Dulbecco's modified Eagles medium (DMEM), Gibco #11965-092; Knockout Dulbecco's modified Eagles medium (KO DMEM), Gibco #10829-018; 200 mM L-glutamine, Gibco #15039-027; non-essential amino acid solution, Gibco 11140-050; beta-mercaptoethanol, Sigma #M7522; human recombinant basic fibroblast growth factor (bFGF), Gibco #13256-029. Exemplary serum-containing embryonic stem (ES) medium is made with 80% DMEM (typically KO DMEM), 20% defined fetal bovine serum (FBS) not heat inactivated, 0.1 mM non-essential amino acids, 1 mM L-glutamine, and 0.1 mM beta-mercaptoethanol. The medium is filtered and stored at 4 degrees C. for no longer than 2 weeks. Serum-free embryonic stem (ES) medium is made with 80% KO DMEM, 20% serum replacement, 0.1 mM non-essential amino acids, 1 mM L-glutamine, and 0.1 mM beta-mercaptoethanol. An effective serum replacement is Gibco #10828-028. The medium is filtered and stored at 4 degrees C. for no longer than 2 weeks. Just before use, human bFGF is added to a final concentration of 4 ng/mL (Bodnar et al., Geron Corp, International Patent Publication WO 99/20741).

The media may comprise Knockout DMEM media (Invitrogen-Gibco, Grand Island, N.Y.), supplemented with 10% serum replacement media (Invitrogen-Gibco, Grand Island, N.Y.), 5 ng/ml FGF2 (Invitrogen-Gibco, Grand Island, N.Y.) and 5 ng/ml PDGF AB (Peprotech, Rocky Hill, N.J.).

Feeder cells (where used) may be propagated in mEF medium, containing 90% DMEM (Gibco #11965-092), 10% FBS (Hyclone #30071-03), and 2 mM glutamine. mEFs are propagated in T150 flasks (Coming #430825), splitting the cells 1:2 every other day with trypsin, keeping the cells subconfluent. To prepare the feeder cell layer, cells are irradiated at a dose to inhibit proliferation but permit synthesis of important factors that support human embryonic stem cells (about 4000 rads gamma irradiation). Six-well culture plates (such as Falcon #304) are coated by incubation at 37 degrees C. with 1 mL 0.5% gelatin per well overnight, and plated with 375,000 irradiated mEFs per well. Feeder cell layers are typically used 5 h to 4 days after plating.

Conditions for culturing other stem cells are known, and can be optimized appropriately according to the cell type. Media and culture techniques for particular cell types referred to in the previous section are provided in the references cited.

Serum Free Media

The methods and compositions described here may include culture of stem cells in a serum-free medium.

The term "serum-free media" may comprise cell culture media which is free of serum proteins, e.g. fetal calf serum. Serum-free media are known in the art, and are described for example in U.S. Pat. Nos. 5,631,159 and 5,661,034. Serum-free media are commercially available from, for example, Gibco-BRL (Invitrogen).

The serum-free media may be protein free, in that it may lack proteins, hydrolysates, and components of unknown composition. The serum-free media may comprise chemically-defined media in which all components have a known chemical structure. Chemically-defined serum-free media is advantageous as it provides a completely defined system which eliminates variability and allows for improved reproducibility and more consistent performance, and decreases possibility of contamination by adventitious agents.

The serum-free media may comprise Knockout DMEM media (Invitrogen-Gibco, Grand Island, N.Y.).

The serum-free media may be supplemented with one or more components, such as serum replacement media, at a concentration of for example, 5%, 10%, 15%, etc. The serum-free media may be supplemented with 10% serum replacement media from Invitrogen-Gibco (Grand Island, N.Y.).

The serum-free medium in which the dissociated or disaggregated embryonic stem cells are cultured may comprise one or more growth factors. A number of growth factors are known in the art, including FGF2, IGF-2, Noggin, Activin A, TGF beta 1, HRG1 beta, LIF, S1P, PDGF, BAFF, April, SCF, Flt-3 ligand, Wnt3A and others. The growth factor(s) may be used at any suitable concentration such as between 1 pg/ml to 500 ng/ml.

Media Supplements

Culture media may be supplemented with one or more additives. For example, these may be selected from one or more of: a lipid mixture, Bovine Serum Albumin (e.g. 0.1% BSA), hydrolysate of soybean protein.

Sources of Pluripotent Cells

Several methods have now been provided for the isolation of pluripotent stem cells that do not lead to the destruction of an embryo, e.g. by transforming (inducing) adult somatic cells or germ cells. These methods include:

1. Reprogramming by nuclear transfer. This technique involves the transfer of a nucleus from a somatic cell into an oocyte or zygote. In some situations this may lead to the creation of an animal-human hybrid cell. For example, cells may be created by the fusion of a human somatic cell with an animal oocyte or zygote or fusion of a human oocyte or zygote with an animal somatic cell.

2. Reprogramming by fusion with embryonic stem cells. This technique involves the fusion of a somatic cell with an embryonic stem cell. This technique may also lead to the creation of animal-human hybrid cells, as in 1 above.

3. Spontaneous re-programming by culture. This technique involves the generation of pluripotent cells from non-pluripotent cells after long term culture. For example, pluripotent embryonic germ (EG) cells have been generated by long-term culture of primordial germ cells (PGC) (Matsui et al., Derivation of pluripotential embryonic stem cells from murine primordial germ cells in culture. Cell 70, 841-847, 1992, incorporated herein by reference). The development of pluripotent stem cells after prolonged culture of bone marrow-derived cells has also been reported (Jiang et al., Pluripotency of mesenchymal stem cells derived from adult marrow. Nature 418, 41-49, 2002, incorporated herein by reference). They designated these cells multipotent adult progenitor cells (MAPCs). Shinohara et al also demonstrated that pluripotent stem cells can be generated during the course of culture of germline stem (GS) cells from neonate mouse testes, which they designated multipotent germline stem (mGS) cells (Kanatsu-Shinohara et al., Generation of pluripotent stem cells from neonatal mouse testis. Cell 119, 1001-1012, 2004).

4. Reprogramming by defined factors. For example the generation of iPS cells by the retrovirus-mediated introduction of transcription factors (such as Oct-3/4, Sox2, c-Myc, and KLF4) into mouse embryonic or adult fibroblasts, e.g. as described above. Kaji et al (Virus-free induction of pluripotency and subsequent excision of reprogramming factors. Nature. Online publication 1 Mar. 2009) also describe the non-viral transfection of a single multiprotein expression vector, which comprises the coding sequences of c-Myc, Klf4, Oct4 and Sox2 linked with 2A peptides, that can reprogram both mouse and human fibroblasts. iPS cells produced with this non-viral vector show robust expression of pluripotency markers, indicating a reprogrammed state confirmed functionally by in vitro differentiation assays and formation of adult chimaeric mice. They succeeded in establishing reprogrammed human cell lines from embryonic fibroblasts with robust expression of pluripotency markers.

Methods 1-4 are described and discussed by Shinya Yamanaka in Strategies and New Developments in the Generation of Patient-Specific Pluripotent Stem Cells (Cell Stem Cell 1, July 2007 ª2007 Elsevier Inc), incorporated herein by reference.

5. Derivation of hESC lines from single blastomeres or biopsied blastomeres. See Klimanskaya I, Chung Y, Becker S, Lu S J, Lanza R. Human embryonic stem cell lines derived from single blastomeres. Nature 2006; 444:512, Lei et al Xeno-free derivation and culture of human embryonic stem cells: current status, problems and challenges. Cell Research (2007) 17:682-688, Chung Y, Klimanskaya I, Becker S, et al. Embryonic and extraembryonic stem cell lines derived from single mouse blastomeres. Nature. 2006; 439:216-219. Klimanskaya I, Chung Y, Becker S, et al. Human embryonic stem cell lines derived from single blastomeres. Nature. 2006; 444:481-485. Chung Y, Klimanskaya I, Becker S, et al. Human embryonic stem cell lines generated without embryo destruction. Cell Stem Cell. 2008; 2:113-117 and Dusko Ilic et al (Derivation of human embryonic stem cell lines from biopsied blastomeres on human feeders with a minimal exposure to xenomaterials. Stem Cells And Development—paper in pre-publication), all incorporated herein by reference.

6. hESC lines obtained from arrested embryos which stopped cleavage and failed to develop to morula and blastocysts in vitro. See Zhang X, Stojkovic P, Przyborski S, et al. Derivation of human embryonic stem cells from developing and arrested embryos. Stem Cells 2006; 24:2669-2676 and Lei et al Xeno-free derivation and culture of human embryonic stem cells: current status, problems and challenges. Cell Research (2007) 17:682-688, both incorporated herein by reference.

7. Parthogenesis (or Parthenogenesis). This technique involves chemical or electrical stimulation of an unfertilised egg so as to cause it to develop into a blastomere from which embryonic stem cells may be derived. For example, see Lin et al. Multilineage potential of homozygous stem cells derived from metaphase II oocytes. Stem Cells. 2003; 21(2): 152-61 who employed the chemical activation of nonfertilized metaphase II oocytes to produce stem cells.

8. Stem cells of fetal origin. These cells lie between embryonic and adult stem cells in terms of potentiality and may be used to derive pluripotent or multipotent cells. Human umbilical-cord-derived fetal mesenchymal stem cells (UC fMSCs) expressing markers of pluripotency (including Nanog, Oct-4, Sox-2, Rex-1, SSEA-3, SSEA-4, Tra-1-60, and Tra-1-81, minimal evidence of senescence as shown by β-galactosidase staining, and the consistent expression of telomerase activity) have been successfully derived by Chris H. Jo et al (Fetal mesenchymal stem cells derived from human umbilical cord sustain primitive characteristics during extensive expansion. Cell Tissue Res (2008) 334:423-433, incorporated herein by reference). Winston Costa Pereira et al (Reproducible methodology for the isolation of mesenchymal stem cells from human umbilical cord and its potential for cardiomyocyte generation J Tissue Eng Regen Med 2008; 2: 394-399, incorporated herein by reference) isolated a pure population of mesenchymal stem cells from Wharton's jelly of the human umbilical cord. Mesenchymal stem cells derived from Wharton's jelly are also reviewed in Troyer & Weiss (Concise Review: Wharton's Jelly-Derived Cells Are a primitive Stromal Cell Population. Stem Cells 2008:26:591-599). Kim et al (Ex vivo characteristics of human amniotic membrane-derived stem cells. Cloning Stem Cells 2007 Winter; 9(4): 581-94, incorporated herein by reference) succeeded in isolating human amniotic membrane-derived mesenchymal cells from human amniotic membranes. Umbilical cord is a tissue that is normally discarded and stem cells derived from this tissue have tended not to attract moral or ethical objection.

9. Chung et al. [(2008) Human Embryonic Stem Cell Lines Generated without Embryo Destruction. Cell Stem Cell. 2(2) 113-117. Epub 2008 Jan. 10] describes the generation of human embryonic stem cell lines with the destruction of an embryo.

Induced pluripotent stem cells have the advantage that they can be obtained by a method that does not cause the destruction of an embryo, more particularly by a method that does not cause the destruction of a human or mammalian embryo.

The method described by Chung et al (item 9 above) also permits obtaining of human embryonic stem cells by a method that does not cause the destruction of a human embryo.

As such, aspects of the invention may be performed or put into practice by using cells that have not been prepared exclusively by a method which necessarily involves the destruction of human or animal embryos from which those cells may be derived. This optional limitation is specifically intended to take account of Decision G0002/06 of 25 Nov. 2008 of the Enlarged Board of Appeal of the European Patent Office.

Differentiation of Undifferentiated Cells

Undifferentiated pluripotent cells may be induced to differentiate into a variety of different cell types. For example, the undifferentiated pluripotent cells may be induced to differentiate into cardiac cells (cardiomyocytes), hepatocytes, neural cells, cartilage (chondrocytes), muscle, fat (adipocytes), bone (osteocytes) or other cells. The undifferentiated pluripotent cells may be induced to form tissues such as epithelial tissues, mesoderm, endoderm, ectoderm or epidermis.

Methods of differentiating stem cells are known in the art and are described in for example Itskovitz-Eldor (2000) and Graichen et al (2007) and may be used with undifferentiated pluripotent cells. The cultured stem cells may also be used for the formation of embryoid bodies. Embryoid bodies, and methods for making them, are known in the art. The term "embryoid body" refers to spheroid colonies seen in culture which may be produced by the growth of embryonic stem cells in suspension. Embryoid bodies are of mixed cell types, and the distribution and timing of the appearance of specific cell types corresponds to that observed within the embryo. Embryoid bodies may be generated by plating out embryonic stem cells onto media such as semi-solid media. Methylcellulose media may be used as described in Lim et al, Blood. 1997; 90:1291-1299.

Embryonic stem cells may be induced to form embryoid bodies, for example using the methods described in Itskovitz-Eldor (2000). The embryoid bodies contain cells of all three embryonic germ layers (endoderm, ectoderm, mesoderm).

The embryoid bodies may be further induced to differentiate into different lineages for example by exposure to the appropriate induction factor or an environmental change. Graichen et al (2007) describes the formation of cardiomyocytes from human embryonic stem cells by manipulation of the p38MAP kinase pathway. Graichen demonstrates induction of cardiomyocyte formation from stem cells by exposure to a specific inhibitor of p38 MAP kinase such as SB203580 at less than 10 µm.

Differentiated cells may be employed for any suitable purpose, such as regenerative therapy and cell transplantation as known in the art.

Therapeutic Uses

Differentiated progeny cells obtained by the methods of the present invention have various uses in medicine, for example in cell therapy. Cell therapy may comprise the implantation or transplantation of cells, whether as a population of individual cells, or in the form of a cell aggregate or tissue, and/or regenerative therapy e.g. tissue regeneration, replacement and/or repair. Differentiated progeny cells may be expanded in in vitro culture and directly administered into a patient. They may be used for the repopulation and/or repair of damaged tissue following trauma.

Differentiated progeny cells may be made by ex vivo expansion or directly administered into a patient. They may also be used for the re-population and/or repair of damaged tissue following trauma.

Thus, hematopoietic progenitor cells may be used for bone marrow replacement, while cardiac progenitor cells may be used for cardiac failure patients. Skin progenitor cells may be employed for growing skin grafts for patients and endothelial progenitor cells for endothelization of artificial prosthetics such as stents or artificial hearts.

Differentiated progeny cells produced by the methods and compositions described here may be used for, or for the preparation of a pharmaceutical composition for, the treatment of a disease. Such disease may comprise a disease treatable by regenerative therapy, including cardiac failure, bone marrow disease, skin disease, burns, degenerative disease such as diabetes, Alzheimer's disease, Parkinson's disease and cancer.

Differentiated progeny cells may also be used for tissue reconstitution or regeneration in a human patient in need thereof. The cells are administered in a manner that permits them to graft to the intended tissue site and reconstitute or regenerate the functionally deficient area.

For example, the methods and compositions described here may be used to modulate the differentiation of stem cells. Differentiated cells may be used for tissue engineering, such as for the growing of skin grafts. Modulation of stem cell differentiation may be used for the bioengineering of artificial organs or tissues, or for prosthetics, such as stents.

In another example, neural stem cells are transplanted directly into parenchymal or intrathecal sites of the central nervous system, according to the disease being treated. Grafts are done using single cell suspension or small aggregates at a density of 25,000-500,000 cells per µL (U.S. Pat. No. 5,968,829). The efficacy of neural cell transplants can be assessed in a rat model for acutely injured spinal cord as described by McDonald et al. (Nat. Med. 5:1410, 1999). A successful transplant will show transplant-derived cells present in the lesion 2-5 weeks later, differentiated into astrocytes, oligodendrocytes, and/or neurons, and migrating along the cord from the lesioned end, and an improvement in gate, coordination, and weight-bearing.

Certain neural progenitor cells are designed for treatment of acute or chronic damage to the nervous system. For example, excitotoxicity has been implicated in a variety of conditions including epilepsy, stroke, ischemia, Hunting-ton's disease, Parkinson's disease and Alzheimer's disease. Certain differentiated cells as made according to the methods described here may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

Hepatocytes and hepatocyte precursors prepared using our methods can be assessed in animal models for ability to repair liver damage. One such example is damage caused by intraperitoneal injection of D-galactosamine (Dabeva et al., Am. J. Pathol. 143:1606, 1993). Efficacy of treatment can be determined by immunohistochemical staining for liver cell markers, microscopic determination of whether canalicular structures form in growing tissue, and the ability of the treatment to restore synthesis of liver-specific proteins. Liver cells can be used in therapy by direct administration, or as part of a bioassist device that provides temporary liver function while the subject's liver tissue regenerates itself following fulminant hepatic failure.

Cardiomyocytes may be prepared by inducing differentiation of stem cells by modulation of the MAP kinase pathway for example with SB203580, a specific p38 MAP kinase inhibitor, as described in Graichen et al (2007). The efficacy of such cardiomyocytes may be assessed in animal models for cardiac cryoinjury, which causes 55% of the left ventricular wall tissue to become scar tissue without treatment (Li et al., Ann. Thorac. Surg. 62:654, 1996; Sakai et al., Ann. Thorac. Surg. 8:2074, 1999, Sakai et al., J. Thorac. Cardiovasc. Surg. 118:715, 1999). Successful treatment will reduce the area of the scar, limit scar expansion, and improve heart function as determined by systolic, diastolic, and developed pressure. Cardiac injury can also be modelled using an embolization coil in the distal portion of the left anterior descending artery (Watanabe et al., Cell Transplant. 7:239, 1998), and efficacy of treatment can be evaluated by histology and cardiac function. Cardiomyocyte preparations can be used in therapy to regenerate cardiac muscle and treat insufficient cardiac function (U.S. Pat. No. 5,919,449 and WO 99/03973).

Undifferentiated pluripotent cells can be directed to differentiate into a variety of cell types, and offer the possibility of renewable sources of replacement cells and tissues to treat a range of diseases and disorders. These diseases and disorders include Huntington's disease, Parkinson's disease, Alzheimer's disease, spinal cord injury, bone injury (e.g. fracture), stroke, burns, heart disease, diabetes, osteoarthritis, and rheumatoid arthritis. Diseases and disorders requiring transplantable tissues and organs may be treated, and particularly in cases where it is useful to destroy undifferentiated cells before transplantation, for example to prevent the formation of teratoma.

The invention provides medicaments and pharmaceutical compositions which may comprise differentiated progeny cells isolated by any of the methods of the present invention. The medicaments and pharmaceutical compositions may be provided for use in a method of medical treatment, as described above. Suitable pharmaceutical compositions may further comprise a pharmaceutically acceptable carrier, adjuvant or diluent.

Thus, the invention also provides a pharmaceutical composition and a medicament comprising cells which have been treated to destroy undifferentiated pluripotent cells, using the methods of the invention.

Differentiated progeny cells isolated by a method according to the present invention may be used in a method of medical treatment. A method of medical treatment may comprise administering to an individual in need of treatment a therapeutically effective amount of a said medicament or pharmaceutical composition.

A subject to be treated may be any animal or human. The subject is preferably mammalian, more preferably human. The subject may be male or female. The subject may be a patient. Therapeutic uses may be in human or animals (veterinary use).

Medicaments and pharmaceutical compositions according to aspects of the present invention may be formulated for administration by a number of routes, including but not limited to, parenteral, intravenous, intra-arterial, intramuscular, intratumoural, oral and nasal. The medicaments and compositions may be formulated for injection.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Formulating Pharmaceutically Useful Compositions and Medicaments

In accordance with the present invention methods are also provided for the production of pharmaceutically useful compositions, which may be based on a cell or cells so obtained. In addition to the steps of the methods described herein, such methods of production may further comprise one or more steps selected from:
  (a) isolating and/or obtaining differentiated progeny cells;
  (b) mixing the differentiated progeny cells with a pharmaceutically acceptable carrier, adjuvant or diluent.

Step (b) preferably results in formulation/preparation of a pharmaceutical composition or medicament suitable for therapeutic use.

Protein Expression

Molecular biology techniques suitable for the producing polypeptides according to the invention in cells are well known in the art, such as those set out in Sambrook et al., Molecular Cloning: A Laboratory Manual, New York: Cold Spring Harbor Press, 1989

The polypeptide may be expressed from a nucleotide sequence. The nucleotide sequence may be contained in a vector present in a cell, or may be incorporated into the genome of the cell.

A "vector" as used herein is an oligonucleotide molecule (DNA or RNA) used as a vehicle to transfer exogenous genetic material into a cell. The vector may be an expression vector for expression of the genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing peptides according to the invention. The cell may be a prokaryote or eukaryote. Suitable prokaryotic cells include *E. coli*. Examples of eukaryotic cells include a yeast cell, a plant cell, insect cell or a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Methods of producing a polypeptide of interest may involve culture or fermentation of a cell modified to express the polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the polypeptide of interest, that polypeptide is preferably isolated. Any suitable method for separating polypeptides/proteins from cell culture known in the art may be used. In order to isolate a polypeptide/protein of interest from a culture, it may be necessary to first separate the cultured cells from media containing the polypeptide/protein of interest. If the polypeptide/protein of interest is secreted from the cells, the cells may be separated from the culture media that contains the secreted polypeptide/protein by centrifugation. If the polypeptide/protein of interest collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide/protein of interest.

It may then be desirable to isolate the polypeptide/protein of interest from the supernatant or culture medium, which may contain other protein and non-protein components. A common approach to separating polypeptide/protein components from a supernatant or culture medium is by precipitation. Polypeptides/proteins of different solubility are precipitated at different concentrations of precipitating agent such as ammonium sulfate. For example, at low concentrations of precipitating agent, water soluble proteins are extracted. Thus, by adding increasing concentrations of precipitating agent, proteins of different solubility may be distinguished. Dialysis may be subsequently used to remove ammonium sulfate from the separated proteins.

Other methods for distinguishing different polypeptides/proteins are known in the art, for example ion exchange chromatography and size chromatography. These may be used as an alternative to precipitation, or may be performed subsequently to precipitation.

Once the polypeptide/protein of interest has been isolated from culture it may be necessary to concentrate the protein. A number of methods for concentrating a protein of interest are known in the art, such as ultrafiltration or lyophilisation.

Sequence Identity

Percentage (%) sequence identity is defined as the percentage of amino acid residues in a candidate sequence that are identical with residues in the given listed sequence (referred to by the SEQ ID NO) after aligning the sequences and introducing gaps if necessary, to achieve the maximum sequence identity, and not considering any conservative substitutions as part of the sequence identity. Sequence identity is preferably calculated over the entire length of the respective sequences.

Where the aligned sequences are of different length, sequence identity of the shorter comparison sequence may be determined over the entire length of the longer given sequence or, where the comparison sequence is longer than the given sequence, sequence identity of the comparison sequence may be determined over the entire length of the shorter given sequence.

Alignment for purposes of determining percent amino acid sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 1. Table showing overview of methods to prevent hESC tumorigenicity.

FIG. 2. Table showing cytotoxic antibodies capable of inducing cell death in certain target cells.

FIG. 3. Table showing hallmarks of apoptosis and their respective assays.

FIG. 4. Tables, comprising panels 4A and 4B, showing (4A) hallmarks of oncosis and their respective assays, and (4B) differences between oncosis and apoptosis.

FIG. 15. Comprising panels 15A and 15B shows alignment and differences in the amino acids sequences of variable regions between mAb84 (upper row) and A1 (lower row). (15A) complete heavy chain, (15B) complete light chain. CDR sequences shown in bold. Differences in sequence of A1 CDRs underlined.

FIG. 23. Table showing effect of sugars on binding of mAb A1 or mAb 84 to hESC.

Figure 5:
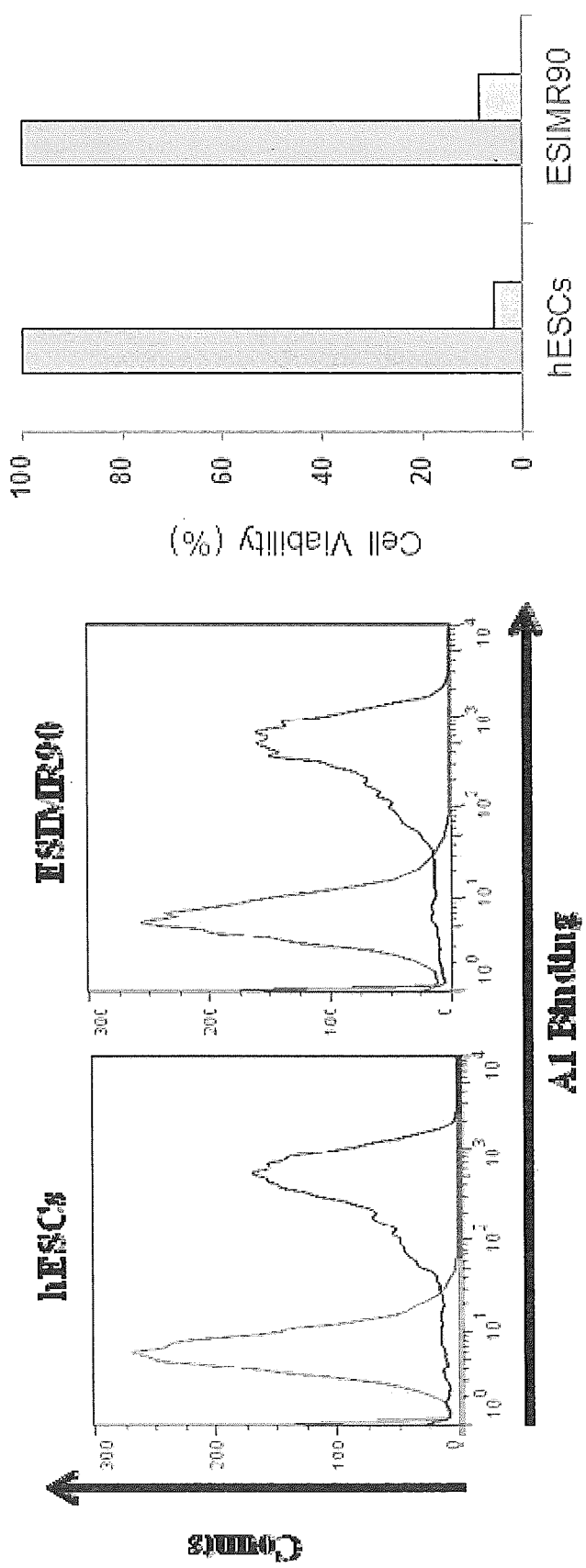
FIG. 5. Charts showing results of flow cytometry analysis of A1 on hESC and iPS (ESIMR90) cells. (Left) Binding of A1 to hESC and iPS cells (ESIMR90). (Right) Cytotoxicity of A1 to both hESC and iPS cells. Left bar represents no treatment control and right bar represents A1-treated cells.

Human embryonic stem cells (hESC), which are derived from the inner cell mass of early-stage human embryo, have the ability to replicate indefinitely (self-renew) and under appropriate conditions differentiate into derivatives of all three germ layers (pluripotency). Various studies have demonstrated the great potential of hESC in tissue engineering and regenerative medicine. However, the major concern of hESC application is the risk of teratoma formation by residual undifferentiated hESC. Currently, there are no available solutions to completely preclude teratoma formation in hESC products. We previously identified mAb84 which was found to be able to kill undifferentiated hESC. However, its tendency to form aggregates as an IgM pentamer might impedes its penetration efficiency into tumor mass.

We have now identified mAb A1 which is able to kill undifferentiated hESC. A1 as an IgG monomer complements the drawback of mAb84. To facilitate the effective use of A1 in hESC therapy, we studied A1 from different aspects: in vitro characterization of A1, elucidation of A1-induced hESC death mechanism. We found that A1 specifically binds to and kills undifferentiated hESC. Its cytotoxicity is time and dosage dependent. Most of the killing occurs within the first 5 minutes. The binding and cytotoxicity of A1 on hESC depend on a common glycan motif: Fucα1-2Galβ1-3GlcNAcβ1-3Galβ1 on A1 antigens. These antigens can be divided into four protein groups: cell adhesion proteins, cytoskeleton-associated proteins, ATPase proteins and transporter proteins. Upon A1 treatment, hESC have significant changes in intracellular and extracellular morphology, such as formation of membrane pores in different sizes, homotypic adhesions, loss of membrane integrity and microvilli, cell swelling, mitochondria enrichment and peripheral relocalization, and vacuolization of cytoplasm. We also found that A1 cytotoxicity is closely associated with actin reorganization.

The experimental results described below suggest that A1 specifically binds to undifferentiated hESC and induces cell death via an oncotic-like pathway. The cytotoxicity is time and dosage dependent. Most of the killing happens within the first 5 minutes. A1 recognizes O-linked glycans target antigens. The binding and cytotoxicity of A1 on hESC depends on a common glycan motif: Fucα1-2Galβ1-3GlcNAcβ1-3Galβ1 on target antigens. Moreover, A1 target antigens can be divided into four protein groups: cell adhesion proteins, cytoskeleton-associated proteins, ATPase proteins and transporter proteins. Upon A1 treatment, hESC have significant changes in intracellular and extracellular morphology, such as formation of homotypic adhesions, loss of membrane integrity and microvilli, cell swelling, mitochondria enrichment and peripheral relocalization, and vacuolization of cytoplasm. We also found the cytotoxicity of A1 is closely associated with actin polymerization.

Example 1—In Vitro Characterization of A1

Generation of Monoclonal Antibody A1 mAb A1 was obtained after immunization of Balb/C mice with undifferentiated human embryonic stem cells. B cells were isolated from the mice and fused with mouse myelomas generating the hybridoma producing A1. A1 has also been chimerized with human IgG1 constant region and the mAb retains specificity and activity vs mouse mAb A1.

Binding and Cytotoxicity of A1 is Specific to Undifferentiated Cells

To investigate the specificity of A1 binding and cytotoxicity, flow cytometry analysis was done on undifferentiated hESC and human fetal lung fibroblasts-derived iPS cells (ESIMR90). From FIG. 5, A1 binds to both hESC and iPS cells (ESIMR90). In addition, A1 is also cytotoxic to both hESC and iPS cells. Therefore, A1 is reactive to both types of pluripotent human stem cells.

To determine if A1 binding and cytotoxicity is only specific to the undifferentiated phenotype, hESC were induced to differentiate by embryoid bodies (EB) formation or FGF-2-starvation.

EB are three-dimensional aggregates derived from undifferentiated hESC. Hemophilic binding of highly expressed $Ca^{2+}$-dependent adhesion molecule E-cadherin facilitates EB formation. Cells within EB undergo spontaneous differentiation and cell specification along the three germ lineages: endoderm, ectoderm, and mesoderm[11,83]. Spontaneously differentiated hESC from EB formation were harvested on day 2, day 5, day 8, day 15 and day 22 for flow cytometry analysis. We co-stained live hESC and differentiating cells with A1 and pluripotent marker, anti-TRA-1-60.

Figure 6A:
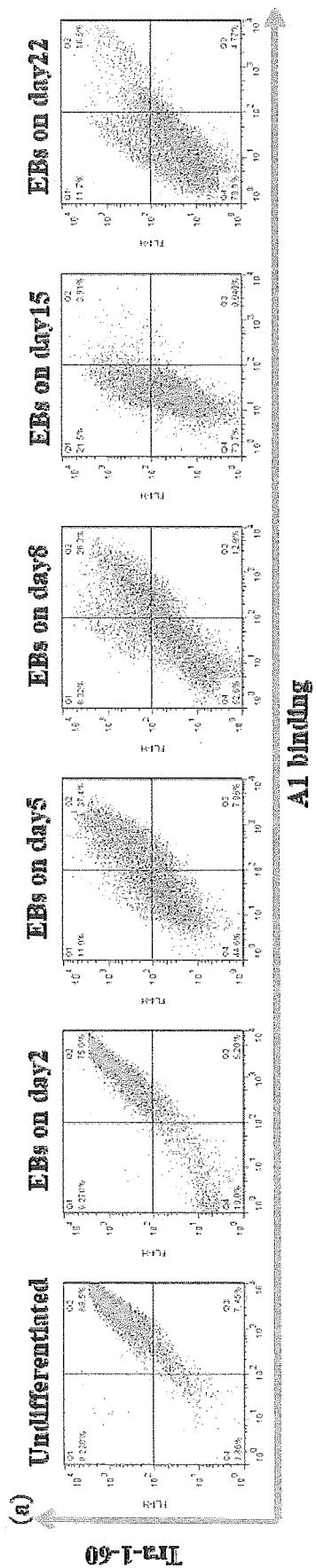
FIG. 6. comprising panels 6A through 6D shows flow cytometry analysis of A1 on differentiated hESC. FACs charts showing the binding of A1 to cells differentiated from hESC via EB formation (6a) and FGF-2-starvation (6b). Charts showing the cytotoxicity of A1 to cells differentiated from hESC via EB formation (6c) and FGF-2-starvation (6d).
Figure 6B:
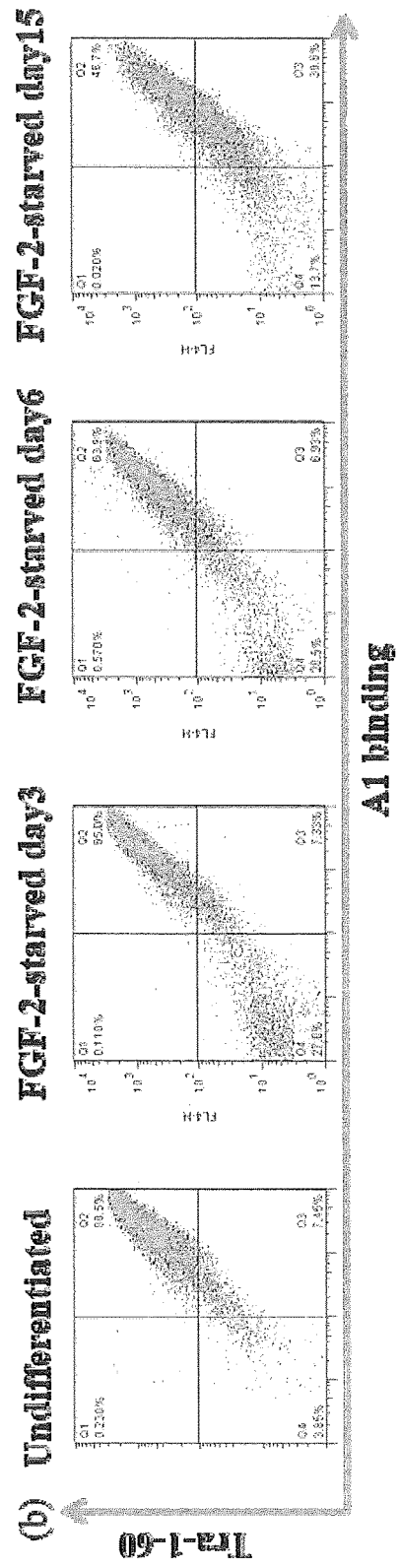
Figure 6C:
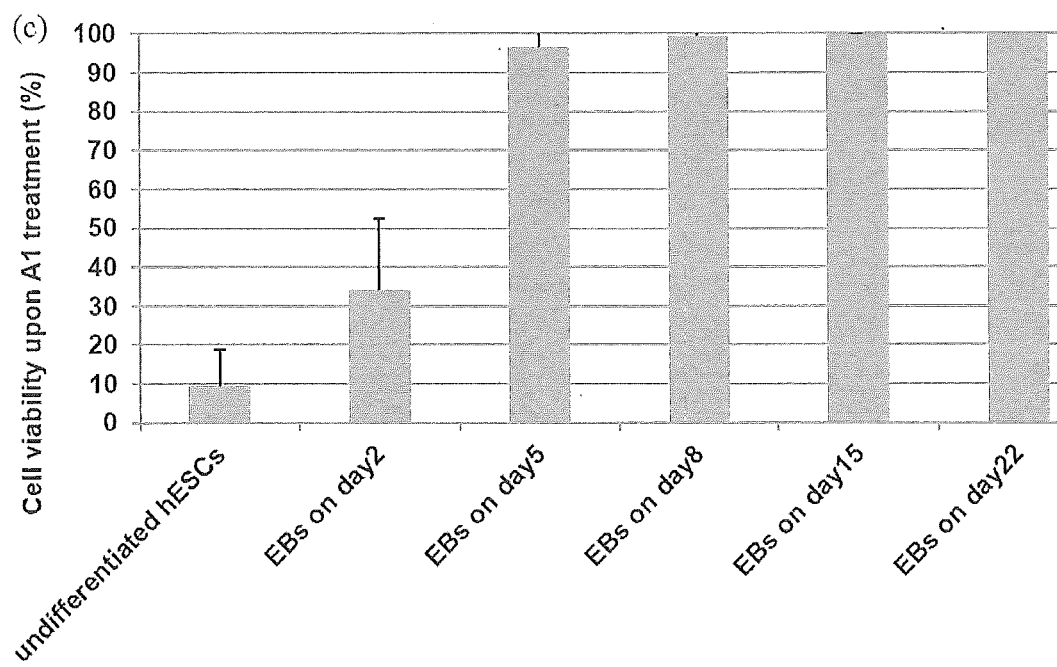
Figure 6D:
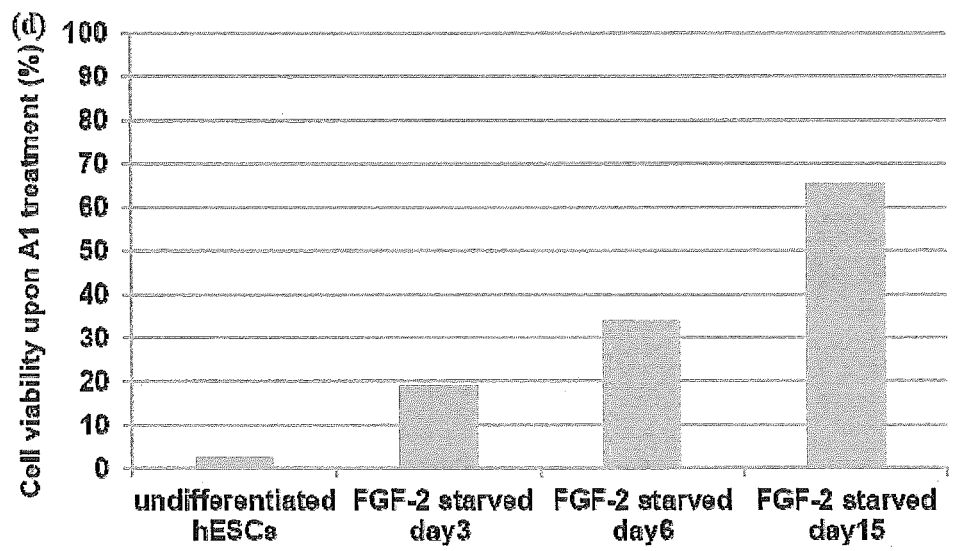

At the same time, viability of the cells was assessed via PI exclusion assay. FIG. 6 shows the binding and killing specificity of A1 to cells at various differentiation stages. It was observed that the binding of A1 to hESC was down-regulated as the cells started to lose pluripotency from days 5 to day 22 (FIG. 6a). The efficiency of cell killing also corresponded closely with the percentage of Tra-1-60 positive cells (FIG. 6c).

Alternatively, hESC were differentiated via FGF-2-starvation since FGF-2 is important for maintaining hESC pluripotency[84]. A similar trend was observed though down-regulation of A1 binding and cytotoxicity was slower (FIG. 6b, d). Taken together, we conclude that the binding and cytotoxicity of A1 is only specific to undifferentiated hESC.

Effect of Dosage on A1 Killing

Figure 7:
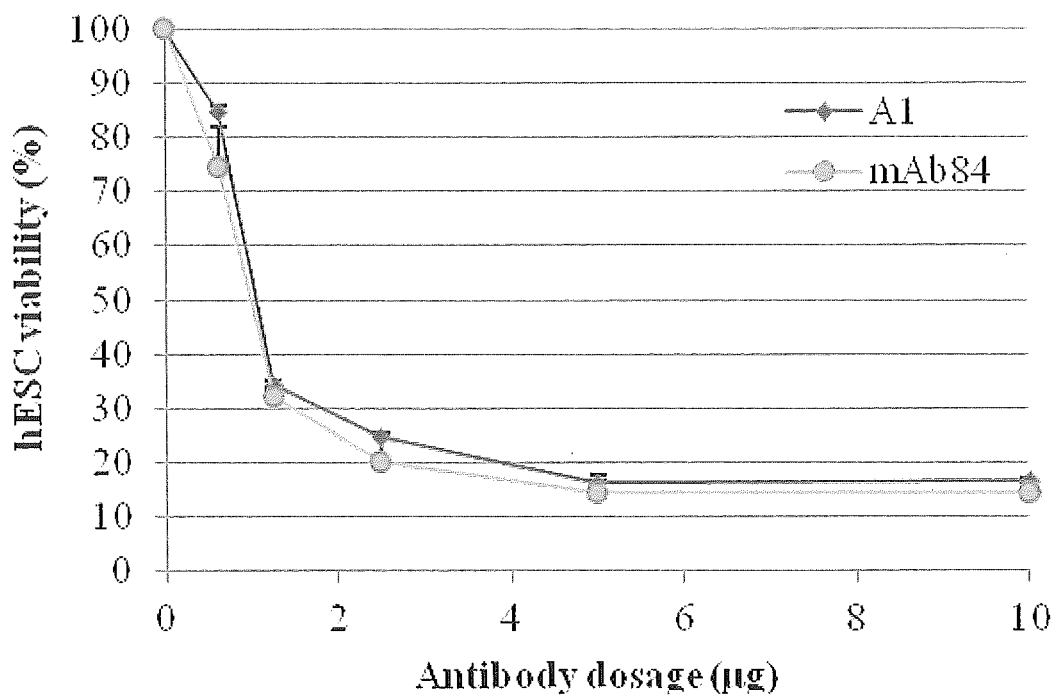
FIG. 7. Chart showing cytotoxicity of both A1 and mAb84 on hESC is dosage-dependent.

Since it has been previously shown that mAb84 binds to and kills undifferentiated hESC, it was used as a benchmark for the in vitro characterization of A1. Firstly, flow cytometry analysis was performed to investigate the effect of dosage on the cytotoxicity of A1 and mAb84. The concentration of A1 and mAb84 was titrated over the range of 0.78-10 µg for $1 \times 10^5$ hESC in a volume of 100 µl for 45 minutes incubation. Cell viability was assessed by PI exclusion assay. We found that A1 and mAb84 have similar dosage-dependence on their cytotoxicity towards hESC (FIG. 7).

Kinetics of A1 Killing

Figure 8:
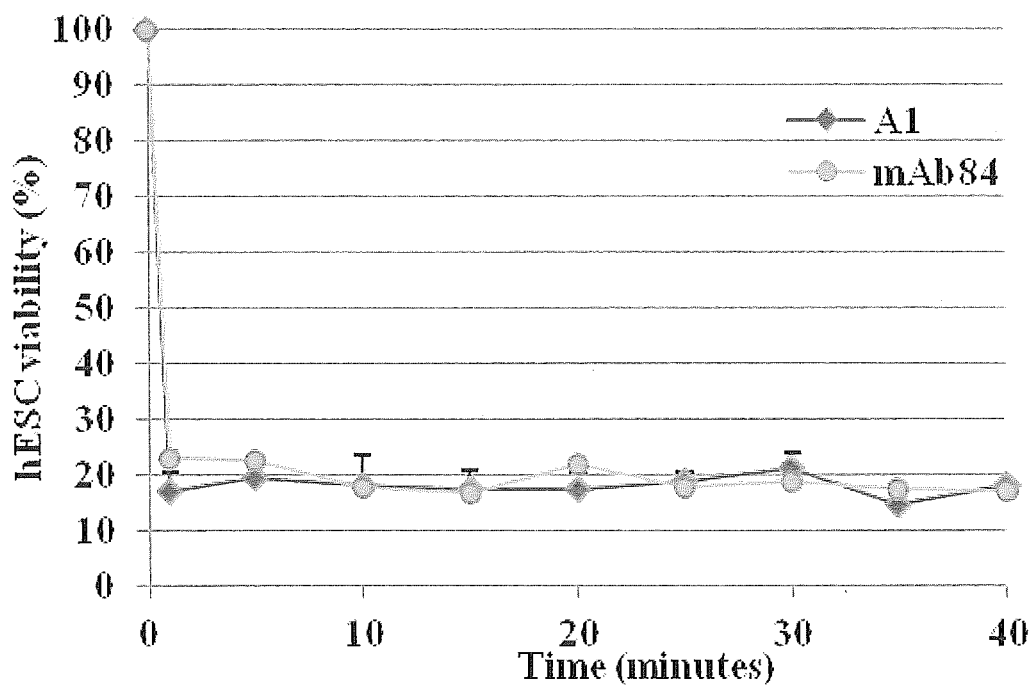
FIG. 8. Chart showing cytotoxicity of A1 and mAb84 on hESC is time-dependent.

Next, we investigated the kinetics of A1 killing. In this time course study, hESC ($1 \times 10^5$) were treated with 5 µg of A1 or mAb84. Cells were harvested after the first minute incubation and subsequently every 5 minutes for PI exclusion assay. We observed that mAb84 and A1 are cytotoxic to hESC in a similar time-dependent manner (FIG. 8). Cell viability dropped by 80% after one minute incubation with mAb84 or A1.

Effect of Dosage on Kinetics of A1 Killing

Figure 9A:
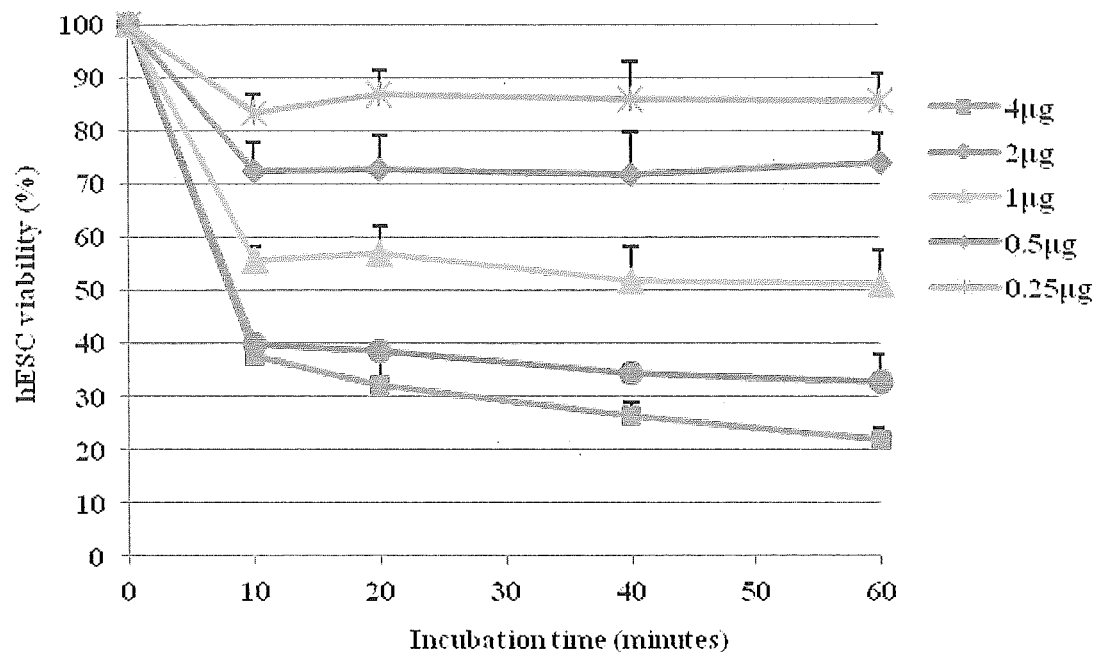
FIG. 9. Charts, comprising panels 9A and 9B, showing flow cytometry analysis of the kinetics of A1 cytotoxicity. (9a) Cells were treated with various dosages of A1 from 0.25 μg to 4 μg at every 10 minutes. (9b) Cells were treated with various dosages of A1 from 0.5 μg to 2 μg at every 2 minutes.
Figure 9B:
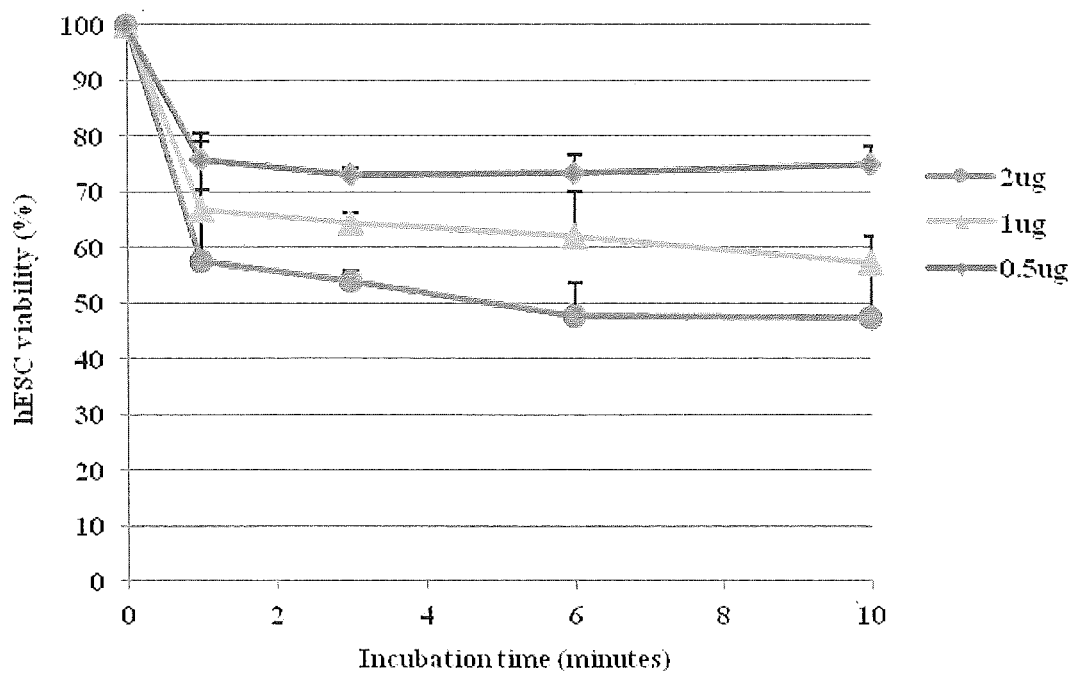

Based on the result of A1 kinetics study shown in FIG. 8, A1 killing proceeds at a very fast rate. In an attempt to slow down the rate of cell killing, we investigated the effect of dosage on the kinetics of A1 killing. Cells were treated with various dosages of A1 and harvested for PI exclusion assay at every 10 minutes. As a result, for each A1 dosage, most of the killings were achieved within the first 10 minutes (FIG. 9a). The assay was repeated however only focusing on the first 10 minutes with the middle three A1 dosages. Cell viability was assessed at every 2 minutes. We found most of the killings were still achieved within the first minute (FIG. 9b). Therefore, it is difficult to slow down the killing process by reducing antibody dosage, but only reduced the killing efficiency.

Competitive Inhibition Between mAb84 and A1

Figure 10:
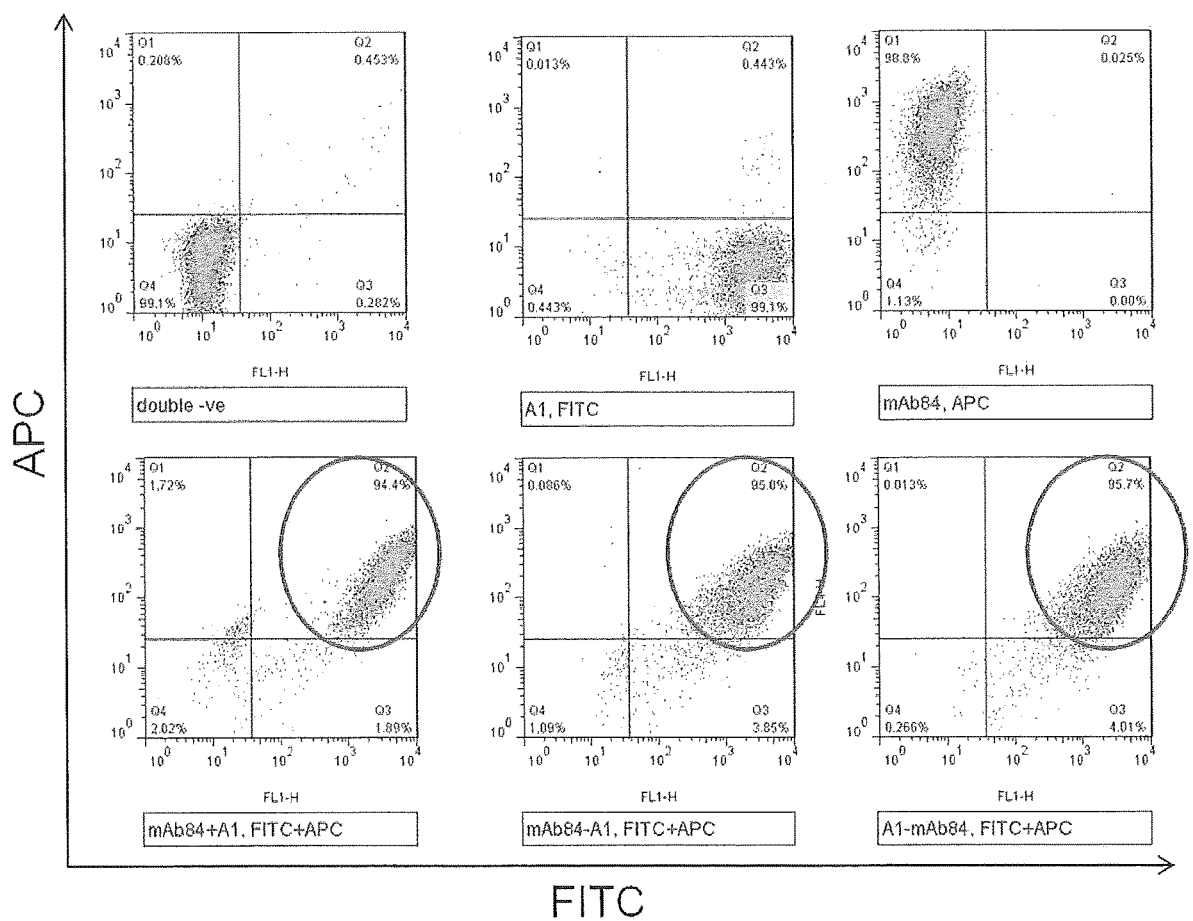
FIG. 10. FACS charts showing flow cytometry analysis of competitive inhibition between mAb84 and A1. (a) Double negative control without treatment; (b) positive control for A1: cells were treated by A1 and labeled with FITC; (c) positive control for mAb84: cells were treated by mAb84 and labeled with APC; (d) cells were treated with A1 and mAb84 simultaneously; (e) cells were firstly treated with mAb84 preceding A1; (f) cells were firstly treated with A1 preceding mAb84.

Since mAb84 and A1 are so similar in the dosage- and time-dependence, we also investigated whether there is competitive inhibition between the binding of mAb84 and A1 on hESC. Cells ($1 \times 10^5$) were either treated with the same amount of mAb84 and A1 simultaneous or sequentially. A1 was labeled with FITC and mAb84 was labeled with APC. FIG. 10 shows the readout of FITC and APC signal, which represents the binding of mAbs to hESC. We observed that regardless of the simultaneous or sequential treatment, the FITC and APC signals are as strong as their corresponding signals in the positive control. Therefore, we concluded that there is no competitive inhibition between the binding of mAb84 and A1 on hESC.

A1-Induced Plasma Membrane Damage

Figure 11A:
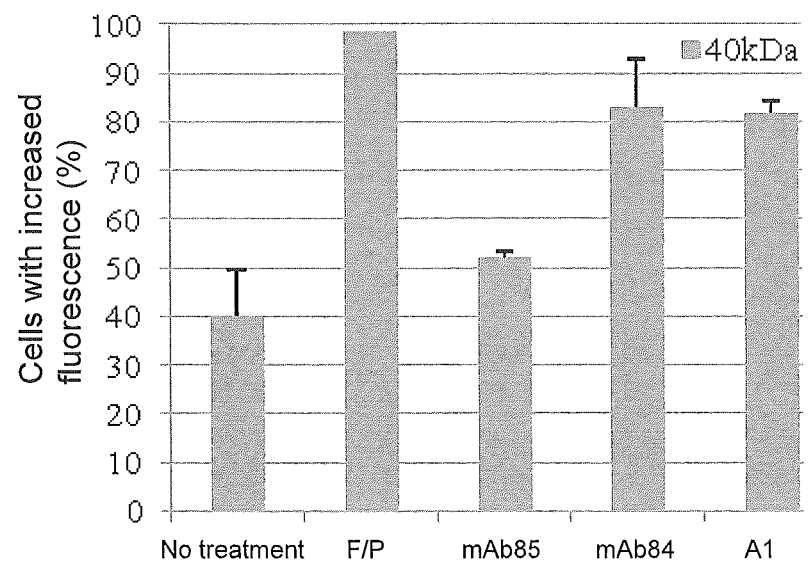
FIG. 11. Charts, comprising panels 11A through 11C, showing determination of pore size with (11A) 40 kDa, (11B) 70 kDa and (11C) 2000 kDa dextran beads respectively. Cells were incubated with mAb 84, mAb 85, or not treated with any mAbs followed by fluorescent dextran beads. As a positive control, cells were fixed and permeabilized. Increase in intracellular fluorescence is correlated with the entry of dextran beads into the cells. The population of cells with high fluorescence was gated and the percentages are represented in the graph.
Figure 11B:
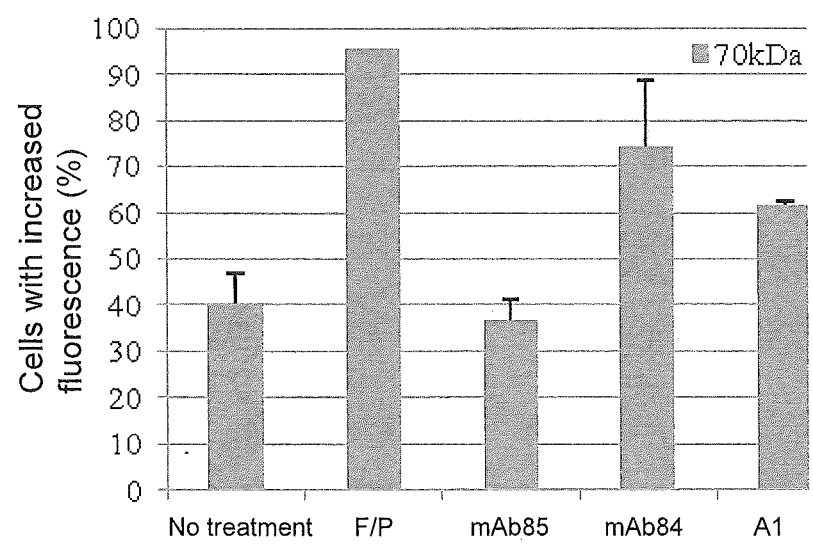
Figure 11C:
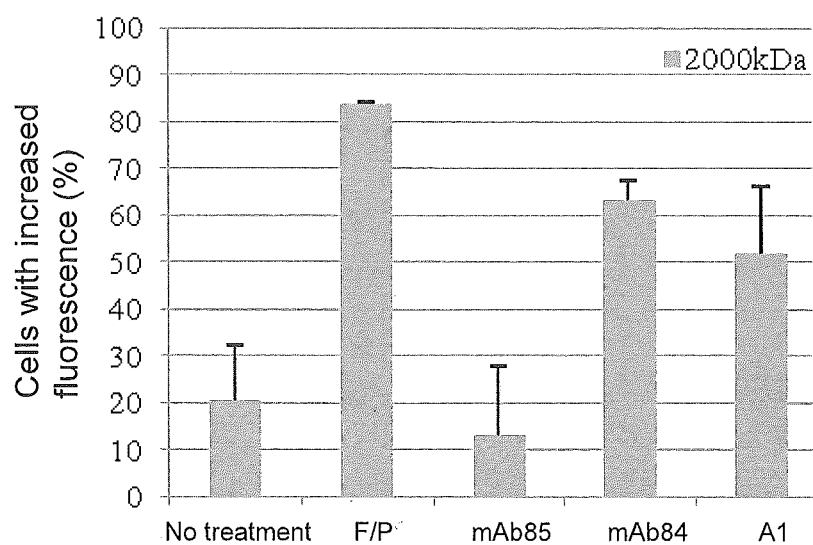

The rapid killing effect and the PI uptake of A1-treated hESC suggest to us that A1 kills hESC via oncosis, which typically results in membrane pore formation. Therefore, the sizes of these pores were estimated with dextran beads of varying molecular weight. In FIG. 11, dextran beads with all three different sizes (40 kDa, 70 kDa, 2000 kDa) were able to diffuse into A1-treated hESC and mAb84-treated hESC, leading to an increase in fluorescence level comparable to the fixed and permeabilized cells. In contrast, the fluorescence level of the negative control and mAb85 control is minimal, representing the background of dead cells. This data suggests that the pores formed on the plasma membrane were greater than 2,000 kDa in size, which is about 20 nm.

A1 Target Antigens on hESC

Figure 12C:
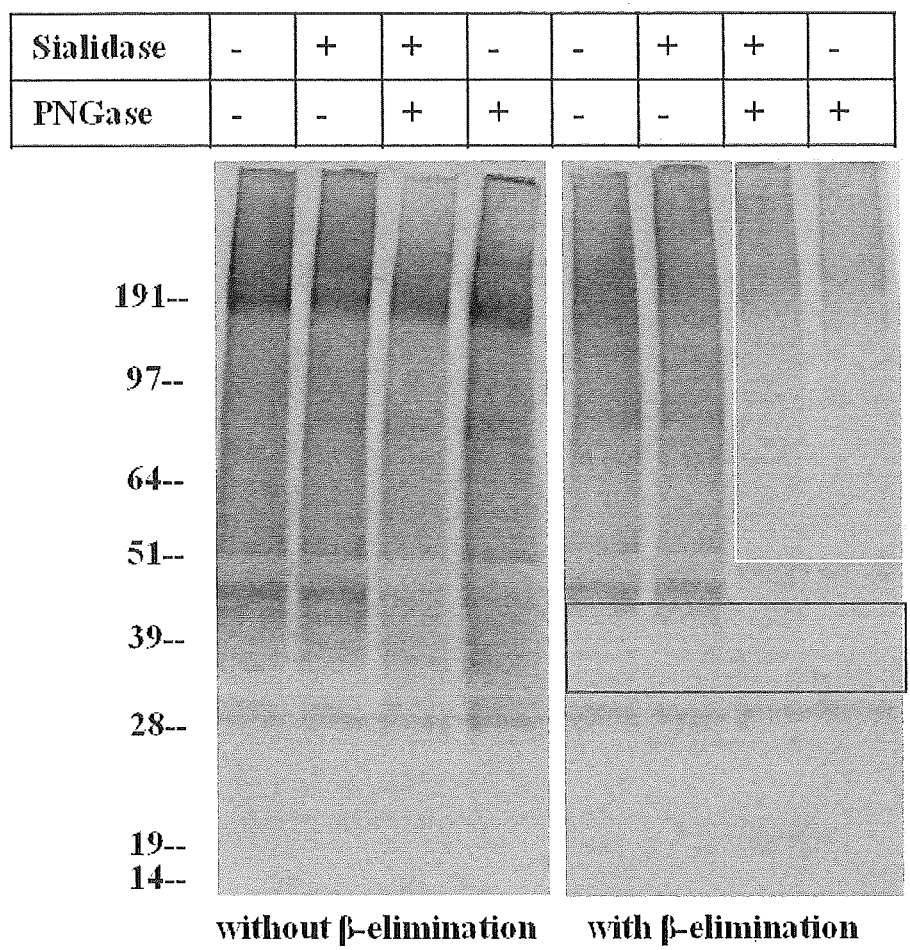
FIG. 12. Comprising panels 12A through 12E shows analysis of A1 target antigens on hESC. Western Blot analysis of immuno-precipitated A1 antigens (12a) with/without periodates treatment; (12c) with/without sialidase, PNGase and β elimination treatment; 12 (f) with/without sugar-blocked A1 or mAb84. Flow cytometry analysis of the binding (12d) and killing (g) of sugar-blocked A1 or mAb84 on hESC. (12b) Four categories of A1 target antigens on hESC. (12e) Schematic structure of the three glycans that block the binding and killing of A1 on hESC. The common glycan motif is highlighted in the circle.

To identify the target antigen of A1, immuno-precipitation (IP) was carried out using the PhyNexus automated system. An antigen smear was detected (FIG. 12a), whereas the antigen of mAb84 is a single protein band identified as: PODXL[37]. The corresponding bands on a silver-stained gel were excised and analyzed by mass spectrometry (MS). By mapping the peptides with Uniprot Protein Database, antigens from the smear can be divided into four protein groups (FIG. 12b): cell adhesion proteins, cytoskeleton-associated proteins, ATPase proteins and transporter proteins. In addition, over 70% of the antigens are glycoproteins.

Next, we proceeded to investigate whether the binding of A1 to these antigens is dependent on glycans. Immunoprecipitated antigens were separated by SDS-PAGE, transferred to PVDF membranes, treated with sodium periodate to open any existing sugar rings and immunoblotted with A1. From the Western Blot analysis (FIG. 12a), most binding of A1 was abolished upon periodate treatment; suggesting binding of A1 is associated with glycans on the antigens.

We then investigated if the binding of A1 is associated with N-linked or O-linked glycans. After immuno-precipitation of antigens by A1, eluted antigens were digested with sialidase, PNGase F and β-elimination. Samples were taken from each enzymatic digestion and immunoblotted with A1. Sialidase was used to remove the terminal sialic acid so that the N-linked or O-linked glycans can be exposed. From the Western Blot analysis (FIG. 12c), the binding of A1 was not lost after sialic acid removal with sialidase and N-glycan removal with PNGase F. Binding of A1 was only lost after both PNGase F digestion and β-elimination (to remove O-linked glycans). From this data, we concluded that A1 binds to O-linked glycans on hESC antigens.

Figure 12D:
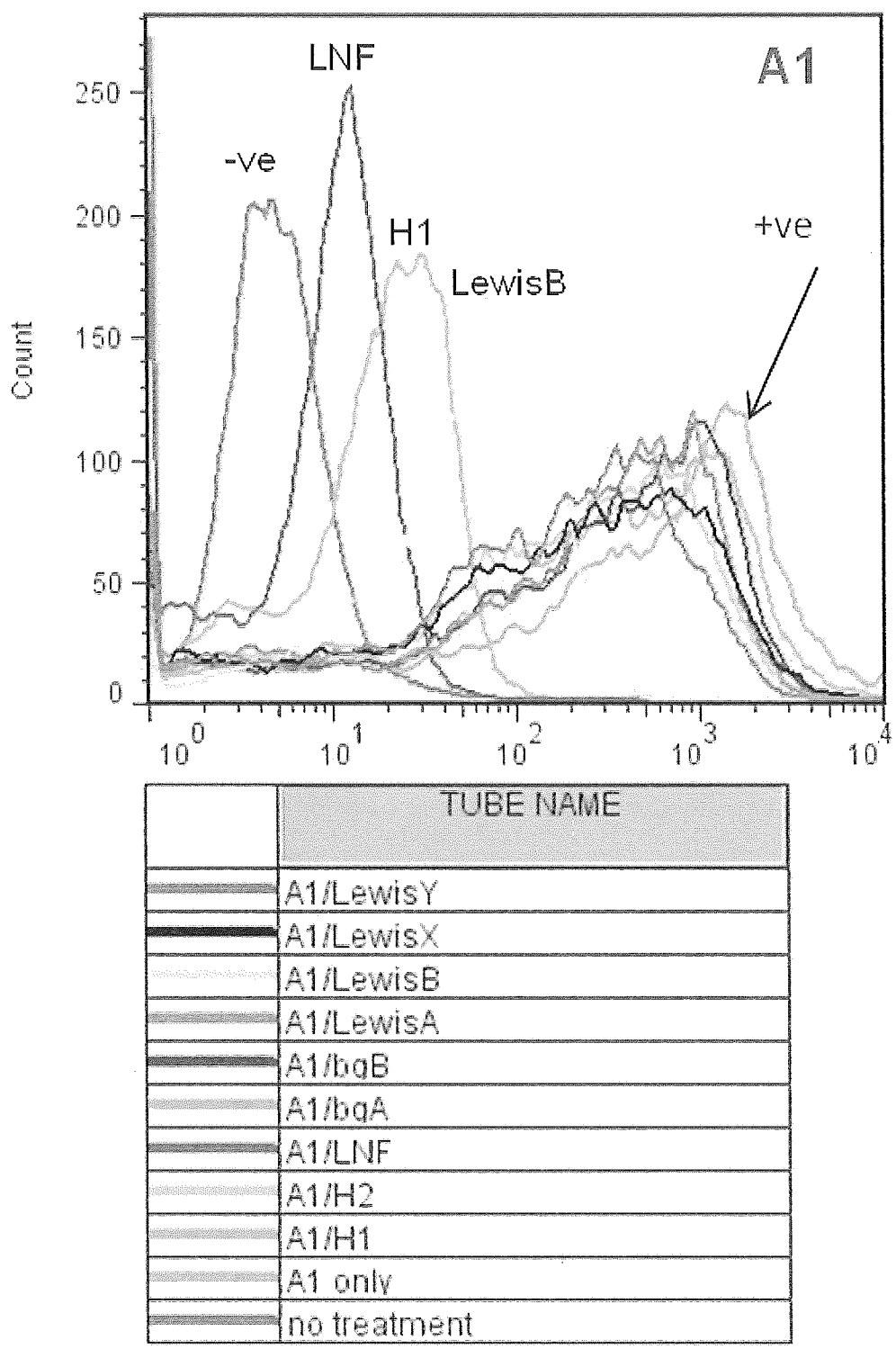
Figure 12E:
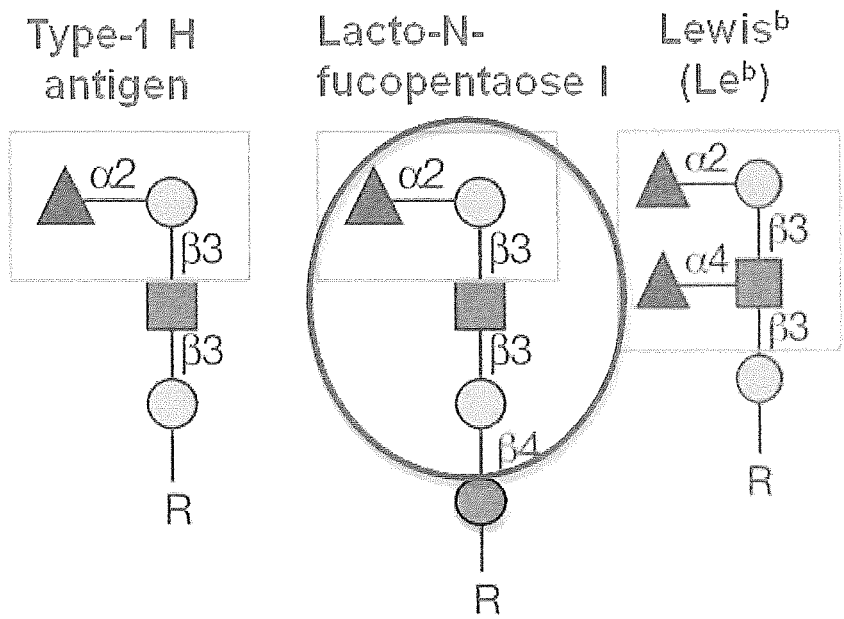

Knowing that A1 binds to O-linked glycans on hESC antigens, we further investigated the sugar composition of the glycans that A1 recognized. A1 was pre-incubated with 9 different sugars, namely, type-1 H (H1), type-2 H (H2), Lacto-N-fucopentaose I (LNFP1), type-1 A (bgA), type-1 B (bgB), LNFP1, Lewis$^a$, Lewis$^b$, Lewis$^x$ and Lewis$^y$ separately for 30 minutes before incubation with a single cell suspension of hESC for 45 minutes. The binding of A1 in different pre-incubation conditions as well as hESC viability was assessed by flow cytometry. From the FACs binding data (FIG. 12d), A1 pre-incubated with type-1 H, LNFP1 and Lewis$^b$ have decreased binding to hESC compared to A1 without any pre-incubation. Since among the nine sugars, only type-1 H, LNFP1 and Lewis-B share a common in four monosaccharide and their linkages, as highlighted in FIG. 12e, we conclude that A1 recognizes a common sugar motif (Fucα1-2Galβ1-3GlcNAcβ1-3Galβ1-) on hESC antigens.

Figure 12F:
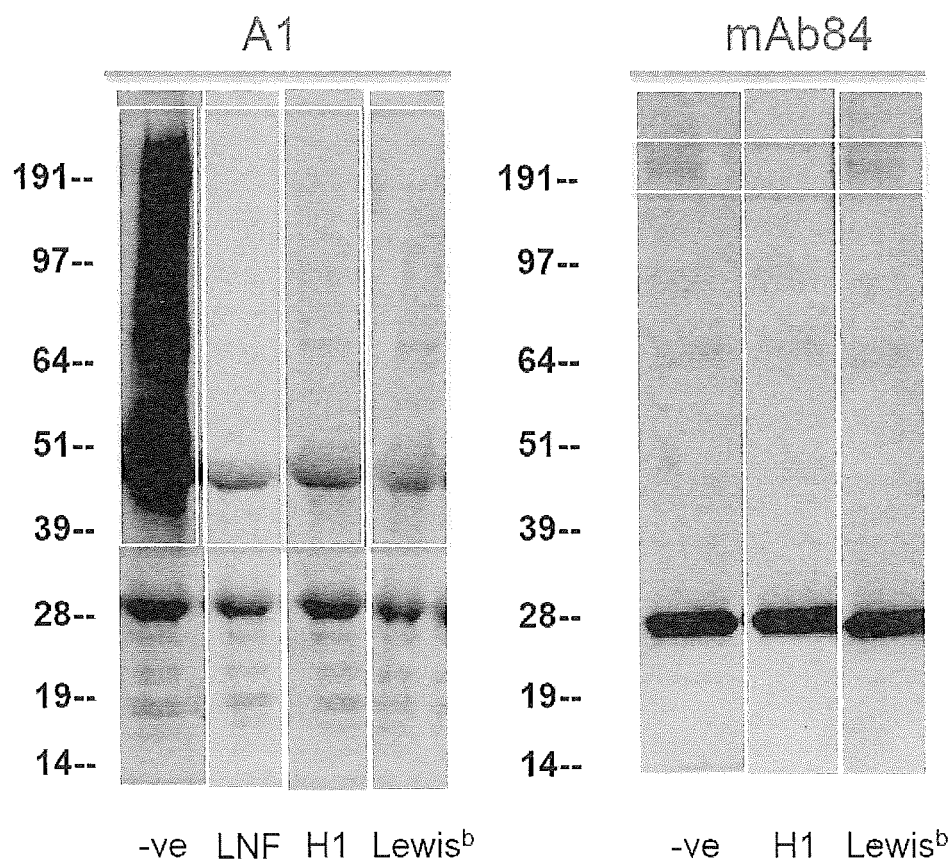

We did a Western Blot analysis to look for the specific antigen or antigens bands that are blocked by the three sugars. Target antigens were immunoprecipitated and used for Western Blot. Sugar-blocked A1 were used as primary antibodies. Four Western Blot membranes in FIG. 12f were blotted with normal A1, H1-blocked A1, LNFP1-blocked A1 and Lewis$^b$-blocked A1 correspondingly. As a result, most of the antigens in the normal A1-blotted membrane are not identified in the other three blots. This is consistent with previous binding profile from flow cytometry analysis.

Figure 12G:
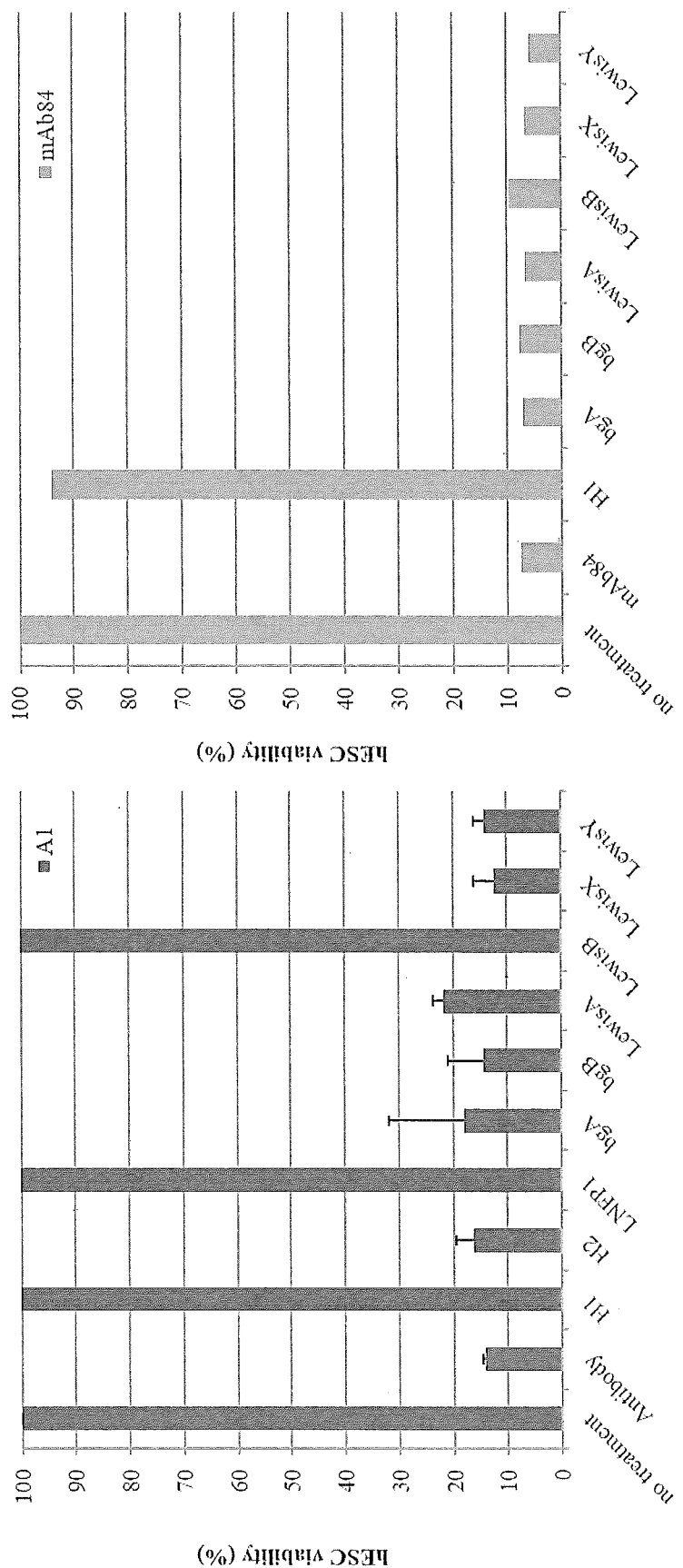
Figure 13:
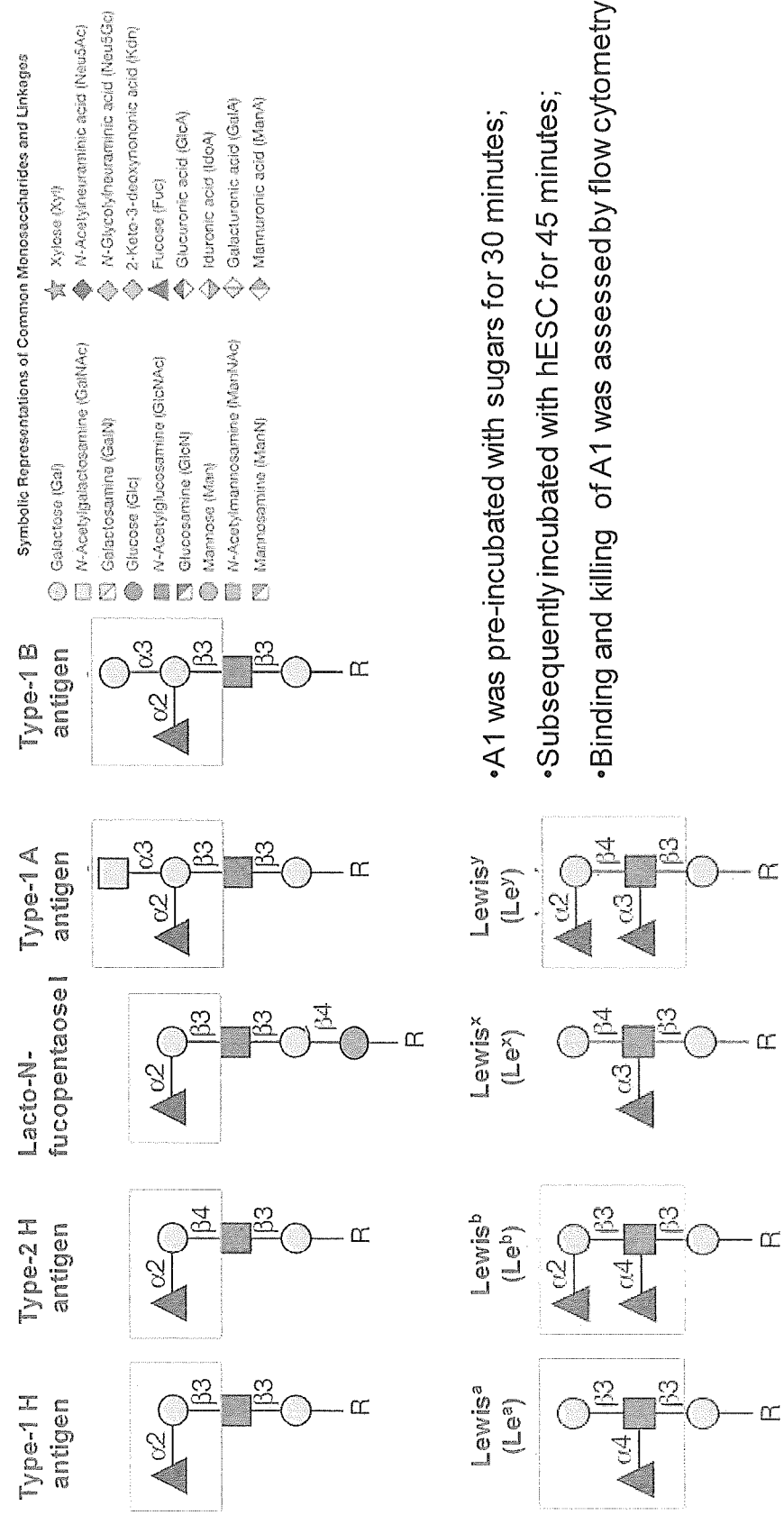
FIG. 13. Graphical representation of sugar types used in sugar inhibition assay.
Figure 14:
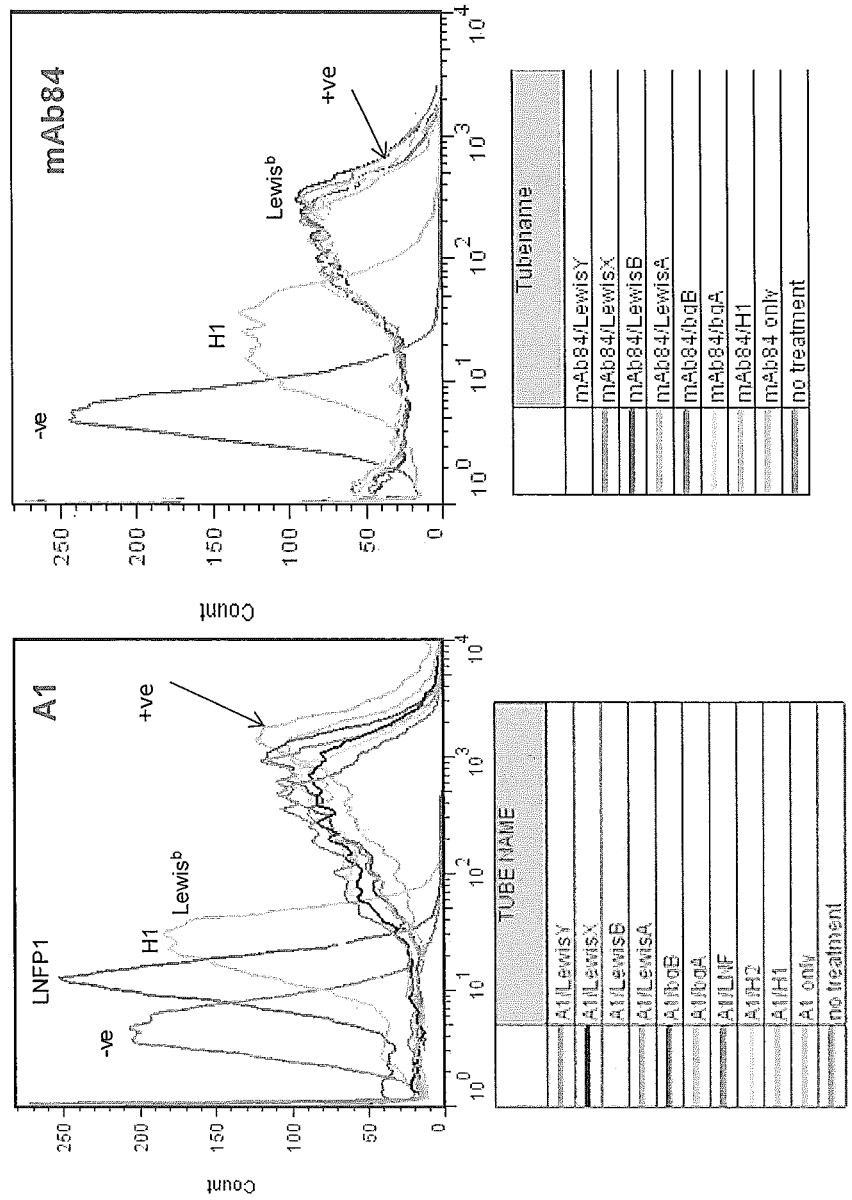
FIG. 14. Charts showing flow cytometry analysis of the binding (d) of sugar-blocked A1 or mAb84 on hESC.

From the same sugar inhibition assay, we further observed that after A1 was pre-incubated with type-1 H, LNFP1 and Lewis$^b$, hESC viability was comparable to that without A1 treatment FIG. 12g, indicating that type-1 H, LNFP1 and Lewis$^b$ prevents A1 from killing hESC. Taken together, we conclude that the binding and cytotoxicity of A1 on hESC depend on the glycan motif: -Fucα1-2Galβ1-3GlcNAcβ1-3Galβ1-.

Sequences in A1 Variable Regions

To confirm that mAb84 and A1 are different antibodies, gene sequence of the mAb heavy and light variable regions was determined. As expected, the variable regions of A1 and mAb84 are different (FIG. 15). In the heavy chain variable regions, there are 5 different amino acids in all three CDRs; and in the light chain variable regions, there are 4 different amino acids in all three CDRs. As CDRs determine the specificity of an antibody for its antigen, these differences in CDRs sequences explains the differences in their antigens.

Example 2—Elucidation of A1-Induced Death Mechanism: Morphological and Structural Changes OF A1-Treated hESC and Mechanistic Studies Dynamics of A1-Induced hESC Death Under Confocal Microscope Knowing that A1 is able to induce hESC death with several minutes of treatment, we observe the intercellular and extracellular morphological changes of A1-treated hESC under time-lapsed Spinning Disk Confocal Microscope. As a result, immediately after the in-situ A1 treatment, hESC start to retract from each other and round up from the culture plate. Cell morphology changed dramatically even after the first minute, suggesting pore formation should be at a very early stage of cell death.

Visualization of hESC Under Transmission Electron Microscope (TEM)

Some previous studies on antibody-induced cell death have used TEM to investigate cell death mechanism. According to Matsuoka[62], mAb RE2 was reported to induce lymphocyte death. Under TEM, they observed the destruction of plasma membrane, dilation of ER, deformation and condensation of mitochondria. With these observations, they concluded that this antibody induces lymphocyte death via oncosis. A recent study on antibody-induced oncosis by Ivanov[66] also revealed early stage intercellular adhesion and involvement of microvillus in homotypic adhesion under TEM.

Figure 16:
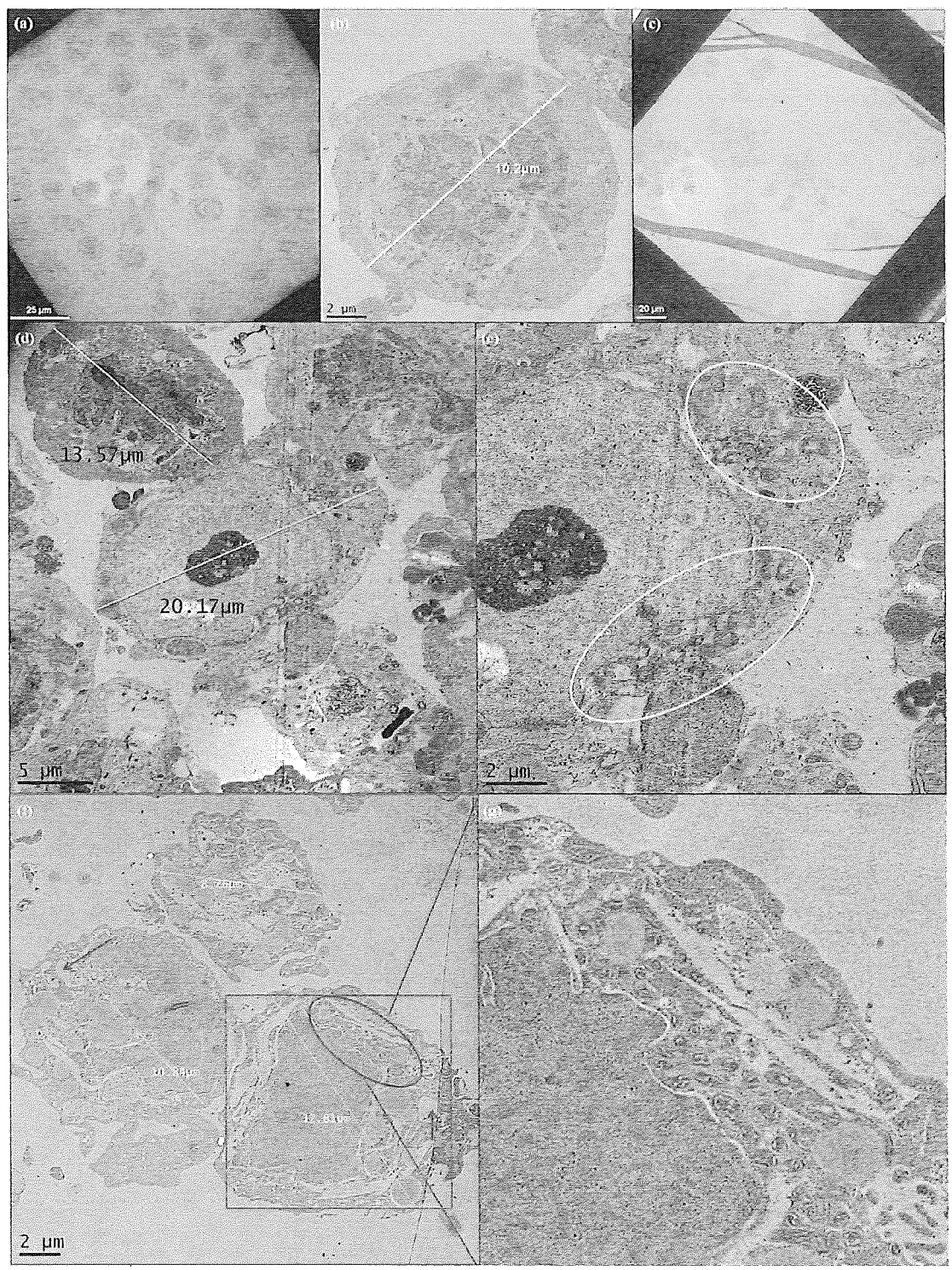
FIG. 16. Transmission Electron Micrographs of Non-treated and A1-treated hESC. Non-treated hESC were uniformly distributed (a) and had a regular size about 10 μm in diameter and uniformly stained proteins; (c) A1-treated hESC form homotypic adhesions; (d) A unit of homotypic adhesions formed by 4 cells; cells were not uniformly stained and lost different degrees of membrane and cell integrity; diameters were labeled for two swelling cells; (e) swelling of mitochondria and peripheral relocalization of mitochondria towards cell-cell adhesion sites (yellow circle). (f) Another unit of homotypic adhesion formed by 3 cells; the cell boxed in red is swelling with significantly enriched mitochondria (circle) and vacuolization of cytoplasm (arrow); (g) Enlarged view of mitochondria showing well-develop cristae, suggesting the cell is at energy producing phage.

We also used TEM to study the intracellular and intercellular morphological changes of A1-treated hESC. Cells were treated with A1, collected and processed for TEM. As a control, cell samples without A1 treatment were also prepared. With preliminary investigation, some morphological alterations of A1-treated hESC have been observed. Cells without A1 treatment were uniformly distributed (FIG. 16a) with a regular size about 10 μm in diameter (FIG. 16b). Characteristically, upon 30 minutes A1 treatment, cells formed intercellular homotypic adhesion or cell aggregations (FIG. 16c).

FIG. 16d shows a unit of intercellular adhesion formed by four cells. Different staining intensities were observed from these cells. One possible reason could be that they are at different stages of cell death and thus the amount of proteins being stained is different. The cell at the bottom right corner was least stained and it has lost membrane integrity and cell morphology, suggesting this cell was undergoing post-mortal oncotic necrosis. The cell in the middle has lower staining intensity than the two cells at top. However, this cell has the most apparent cell swelling and mitochondria swelling. It might suggest that swelling occurred at later stage of cell death. Moreover, peripheral re-localization of mitochondria in this cell towards cell adhesion sites was also observed (FIG. 16e).

FIG. 16f shows another unit of intercellular adhesion formed by three cells. The amount of mitochondria was significantly enriched and there was gross vacuolization of cytoplasm. In an enlarged view (FIG. 16g), well-developed cristae in the mitochondria were also observed suggesting that they were in an energy-producing phase. These observations further proved our hypothesis that A1 kills hESC via oncosis, and it might also imply that A1-induced cell death is associated with mitochondria, ATP and adhesion proteins.

Visualization of hESC Under Scanning Electron Microscope (SEM)

Figure 17:
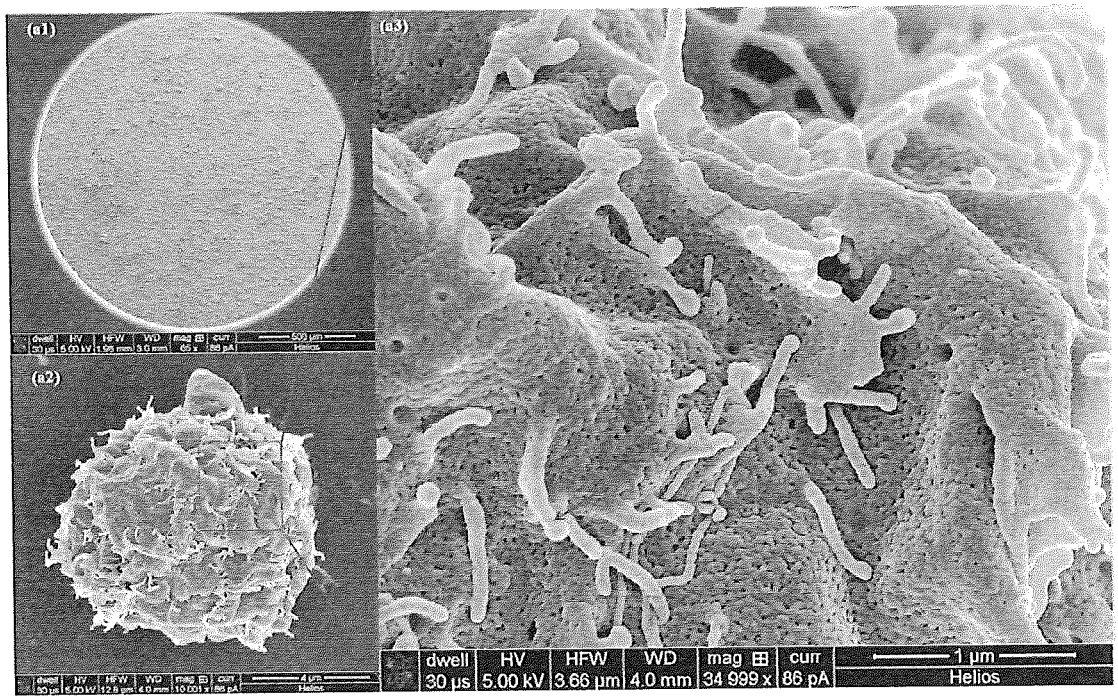
FIG. 17. Scanning Electron Micrographs of non-treated hESC. (a1, top left) Non-treated hESC are normally distributed and have uniform cell size; (a2, bottom left) smooth membrane contours and rich microvilli on the surface of non-treated hESC; (a3, right) enlarged view of the intact cell membrane and display of microvilli.
Figure 18:
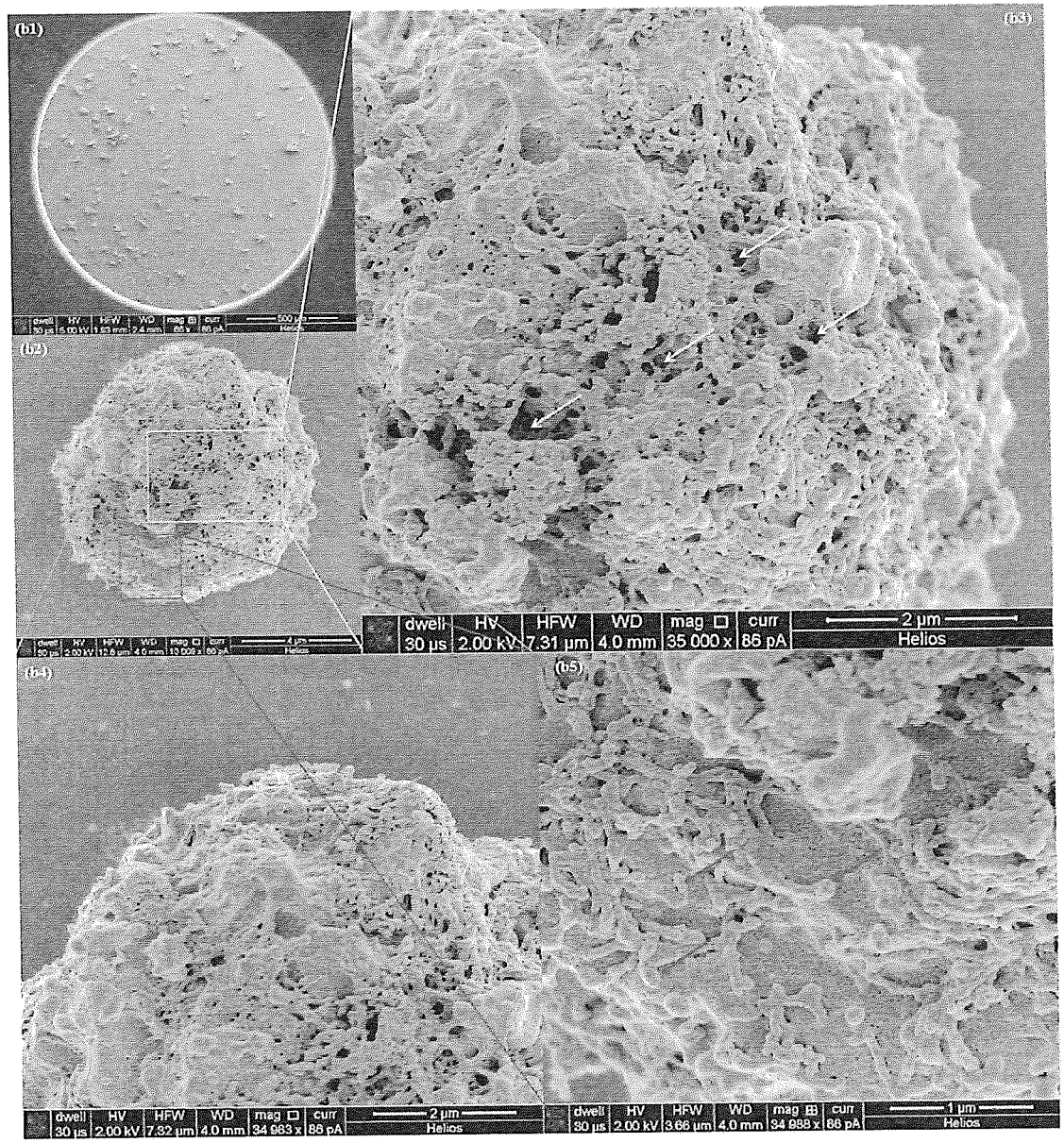
FIG. 18. Scanning Electron Micrographs of A1-treated hESC. (b1, top left) A1-treated hESC form homotypic adhesions; (b2, middle left) A1-treated hESCs formed membrane pores and lost microvilli; (b3, top right) membrane area formed numerous pores and completely lost microvilli; (b4, bottom left) membrane area partially lost membrane integrity and microvilli; (b5, bottom right) membrane area is still intact and covered by microvilli.

To further investigate the lethal effect of A1 on hESC, normal hESC and A1-treated hESC were examined for morphological and structural changes via SEM (FIGS. 17 and 18). Consistent with previous observations in TEM, non-treated hESC have regular sizes and are uniformly distributed (FIG. 17 top left and lower left); whereas A1-treated hESC rapidly formed homotypic adhesions and altered cell size (FIG. 18 top left). The induction of homotypic adhesion occurred within minutes and lasted until the cells are decomposed. Normal hESC have smooth membrane contours and microvilli (FIG. 17 right). However, in the presence of A1, hESC displayed a loss of surface microvilli and membrane integrity (FIG. 18 middle left). Membrane pores (FIG. 18 top right) were formed on the plasma membrane of cells with convoluted surface. These membrane pores are usually covered by debris networks which look like degraded microvilli or cell membrane.

From FIG. 18 middle left, we observed three areas with distinct surface morphology. In FIG. 18 top right, numerous membrane pores were formed and this area is totally free of microvilli. In FIG. 18 bottom left, part of the area has membrane pores formed while the remaining part is covered by partially degraded microvilli. In FIG. 18 bottom right, cell membrane of this area is still intact and the morphology of the microvilli displayed is very similar to those on non-treated hESC. Therefore, we suspect that degradation of microvilli precedes the formation of membrane pores or it is even responsible for the formation of membrane pores.

Figure 19:
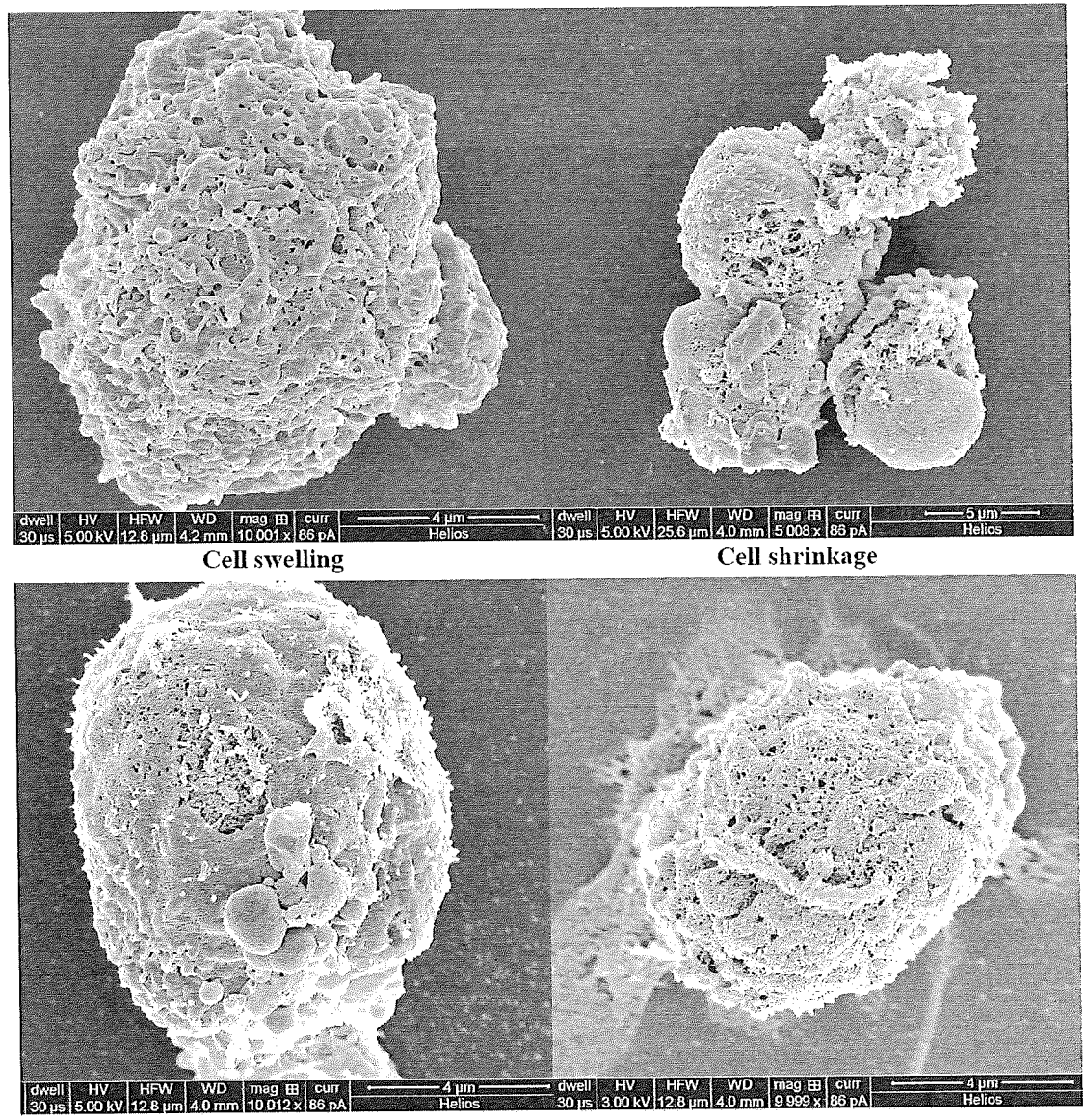
FIG. 19. Scanning Electron Micrographs showing swelling and shrinkage of A1-treated hESC. (Left) The size of A1-treated hESC is larger than 10 μm; (Right) The size of A1-treated hESC is smaller than 10 μm.

More interestingly, A1-treated hESC were found to have both cellular swelling and cellular shrinkage under SEM (FIG. 19). Characteristically, shrinking cells usually have higher degree of morphological change as well as membrane damage, and more surface wrinkling or dents, comparing to swelling cells. These observations suggest to us that cellular swelling should precede cellular shrinkage, whereas destruction of membrane integrity is a continuous process right after A1 treatment and before cell death.

Role of Actin Cytoskeleton in A1-Induced hESC Death

Actin cytoskeleton undergoes constant formation and remodeling, which contributes to its roles in cell motility, cell signaling and the establishment and maintenance of cell junctions and cell shape[85]. A previous study on mAb RE2-mediated T cells death identified that treatment with Cytochalasin B/D completely blocks the cytotoxicity of mAb RE2 towards T cells[62]. Another study on a type II CD20-specific mAb and an HLA-DR-specific mAb in both human lymphoma cell lines and primary chronic lymphocytic leukemia cells also showed that peripheral relocalization of actin cytoskeleton is critical for homotypic adhesion and cell death[66] ENREF 86.

Figure 20A:
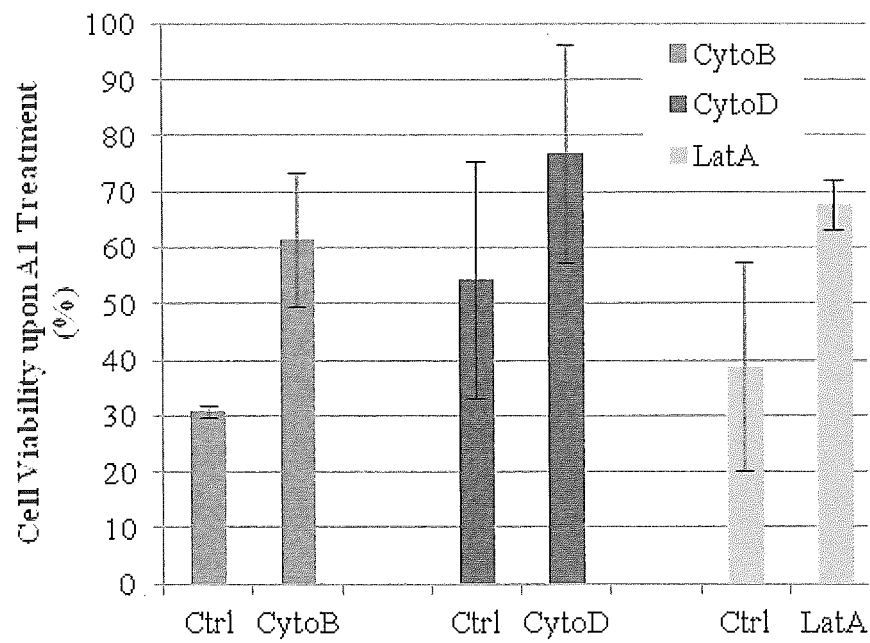
FIG. 20. Comprising panels 20A and 20B shows association between actin cytoskeleton reorganization and A1 cytotoxicity on hESC. (20a) Chart showing treatment with actin inhibitors (Cytochalasin B, Cytochalasin D and Latrunculin A) can prevent A1 cytotoxicity on hESC. Ctrl=hESC without actin inhibitor treatment. (20b) Western Blot analysis of actin-cytoskeleton associated proteins upon A1 treatment.

We first investigated the effect of Cytochalasin B, Cytochalasin D and Latrunculin A on A1-induced hESC death. In general, Cytochalasin B/D inhibits actin polymerization by blocking the fast growing end of actin polymer[86], whereas Latrunculin A binds to G actin and prevents polymerization of actin monomers[87]. Single hESC suspension was incubated with 5 μg A1 and different amount of Cytochalasin B/D or Latrunculin A for 45 minutes and the viability of hESC were assessed by PI exclusion assay. As a result (FIG. 20a), actin inhibitors-treated hESC had a significantly increased viability upon A1 treatment comparing to the untreated cells, suggesting inhibited actin polymerization prevents A1 killing on hESC.

Figure 20B:
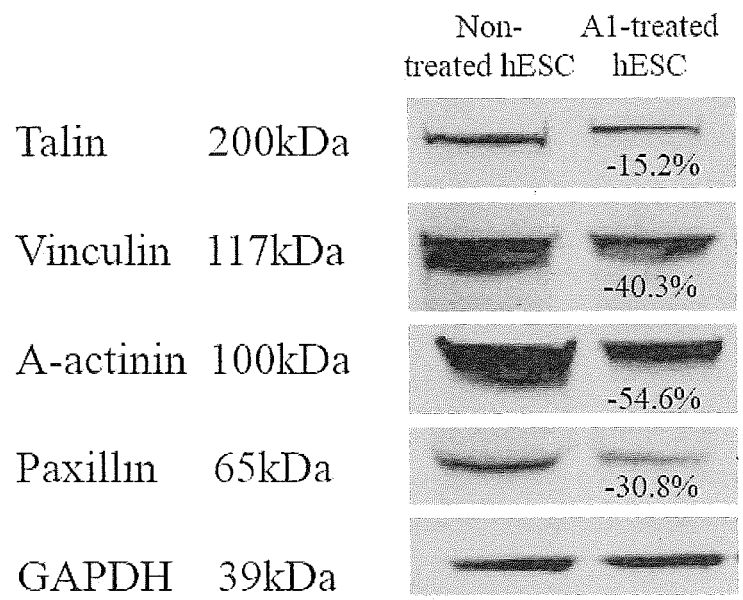
Figure 21A:
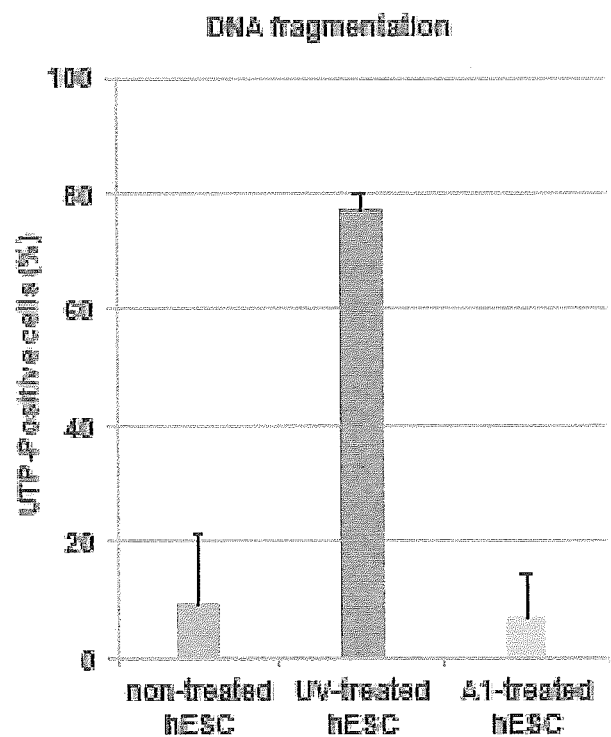
FIG. 21. Comprising panels 21A through 21C, shows A1-induced hESC cell death is not via apoptosis. Charts showing flow cytometry analysis of two apoptotic assays on A1-treated hESC. DNA fragmentation and increased apoptosis activity are hallmarks of cell undergoing apoptosis. Exposure to UV leads to apoptosis of hESC. (21A) TUNEL assay measures DNA fragmentation: UTP-positive cells were correlated to the increased DNA fragmentation; (21B &21C) Caspase assay measures the activity of caspase 9 and caspase 3&7. At the same time, cell death is measured by 7-AAD uptake.
Figure 21B:
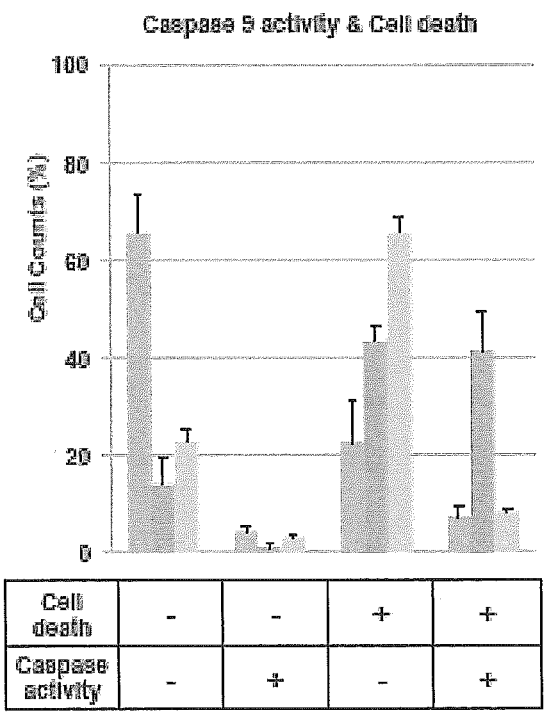
Figure 21C:
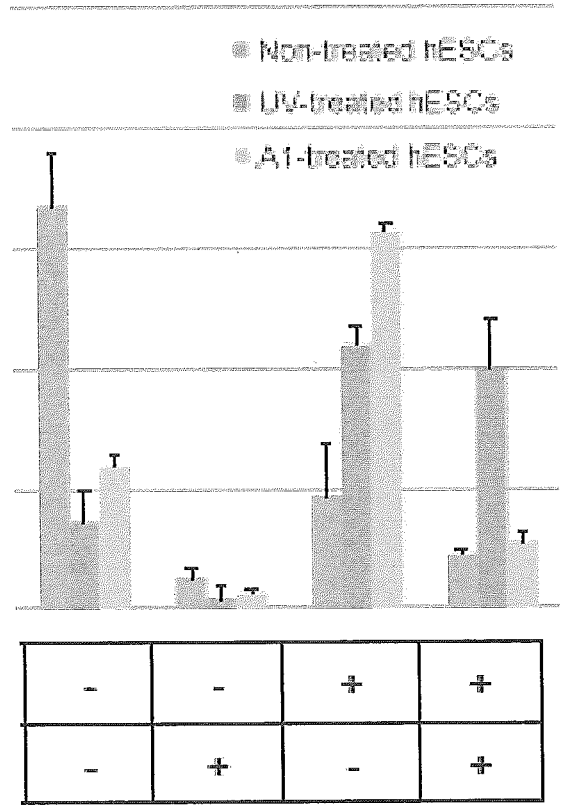
Figure 22A:
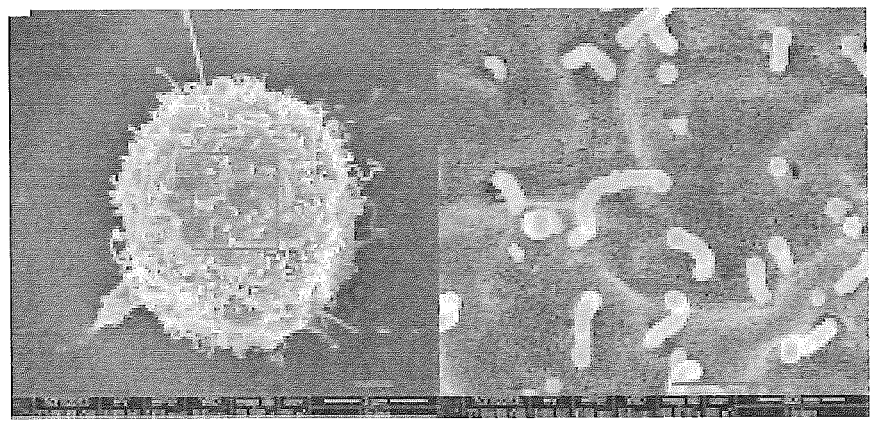
FIG. 22. Comprising panels 22A through 22F shows staged morphological changes of hESC under SEM. Scanning electron micrographs showing 5-stage hESC morphological changes triggered by A1 under Scanning Electron Microscope (SEM). (22A) Non-treated hESC has uniform shape, rich microvilli and intact membrane; (22B, left) A1-treated hESC at stage 1: relatively intact membrane, but degraded/shortened microvilli and cell swelling; (22B, right) Fused microvilli is likely to be the transition from stage 1 to stage 2; (22C, left) A1-treated hESC at stage 2: formation of membrane pore in varied sizes and appearance of partially damaged membrane area in circular shape as highlighted; (22C, right) This circular shaped area is usually surrounded by fused microvilli whereas there is no microvilli but presence of cytoskeleton-like structure within this area; (22D, left) A1-treated hESC at stage 3: microvilli further shortened or even completely disappeared; (22D, right) Disappearance of fused microvilli around the circular area as well as the cytoskeleton-like structures; (22E, left) A1-treated hESC at stage 4: massive membrane damage; (22E, right) Membrane damage was worsen from the damaged circular area of stage 3 and visible nucleus covered by massive cytoskeleton structures; (22E, left) A1-treated hESC at stage 5: damaged membrane peeling off from the nucleus; (22F, right) Uncovered nucleus of A1-treated hESC. Cell swelling and formation of membrane pores are hallmarks of oncotic cell death. Scale bar=1 μm.
Figure 22B:
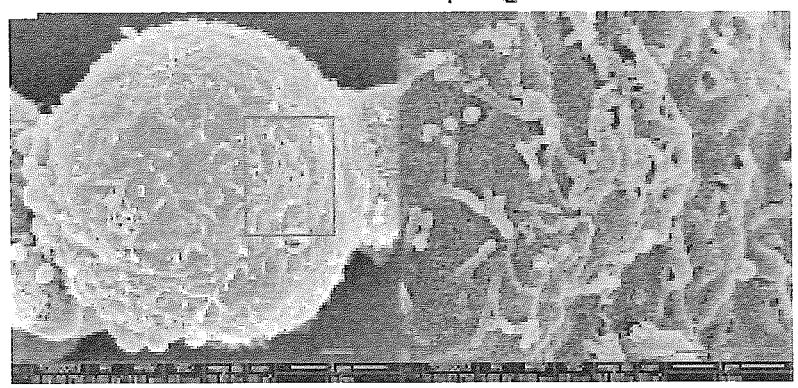
Figure 22C:
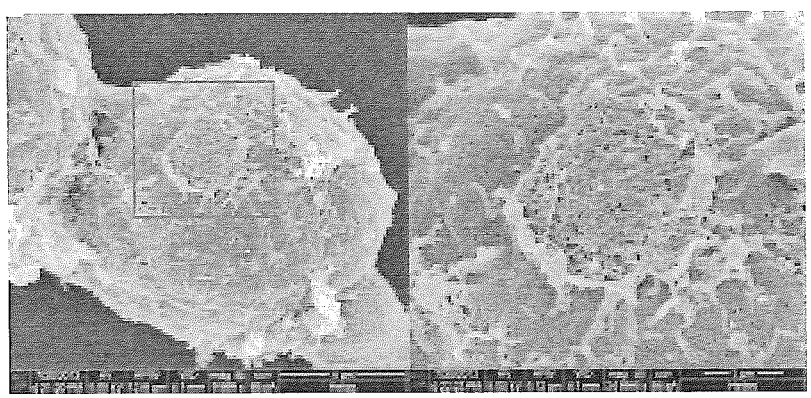
Figure 22D:
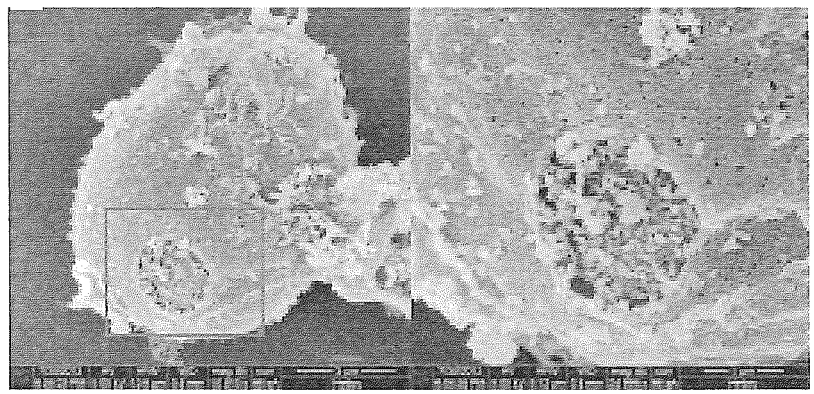
Figure 22E:
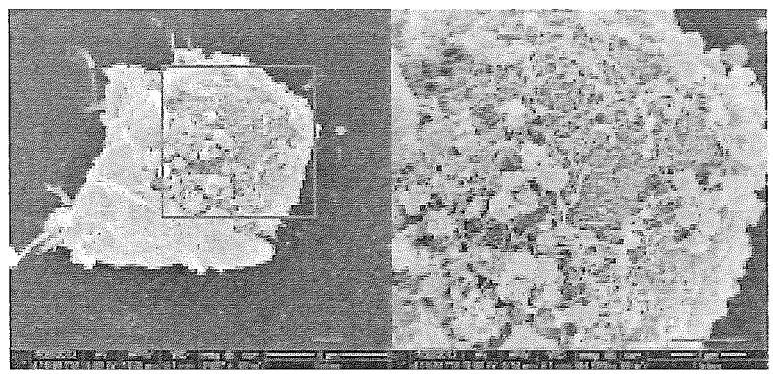
Figure 22F:
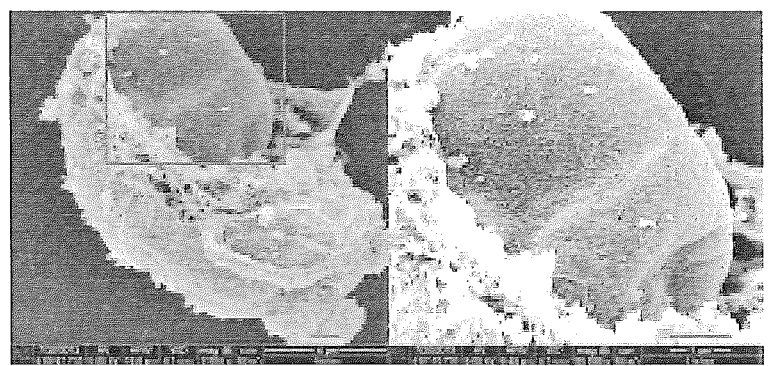

Moreover, in A1-induced hESC death, there was significant reduction in four actin-associated proteins, α-actinin, paxillin, talin and vinculin, compared to those in non-treated hESC (FIG. 20b). Taken together, these results demonstrate a close association of actin reorganization with A1-induced hESC death.

Example 3—Relationship between Amount of Unbound A1 and Bound A1 in a Stoichiometry Assay and Corresponding A1 Killing on hESC at Different Initial Aamounts of A1

Figure 24A:
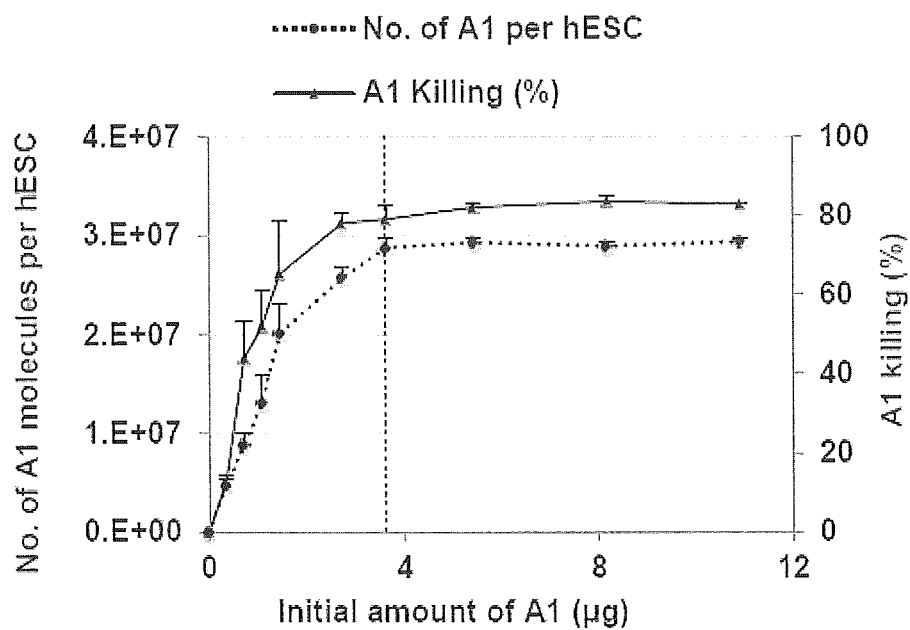
FIG. 24. Comprising panels 24A and 24B provides graphs showing the relationship between the amount of unbound A1 and bound A1 in the stoichiometry assay and the corresponding A1 killing on hESC at different initial amount of A1. (24A) Number of A1 molecules per hESC was measured from stoichiometry assay. A1 killing was measured by propidium iodide (PI) uptake via flow cytometry. Points of binding saturation and killing saturation are highlighted with vertical dotted line. Binding saturation and killing saturation was achieved at the same point, where there are about $3.0 \times 10^7$ A1 molecules per hESC. (24B) The amount of bound A1 is the different between the initial amount of A1 and the amount of unbound A1 measured from stoichiometry assay. Point with saturated A1 killing is highlighted with vertical dotted line. Killing saturation is only achieved when the amount of unbound A1 is significantly higher than the amount of bound A1.

The number of A1 molecules per hESC was measured from stoichiometry assay. A1 killing was measured by propidium iodide (PI) uptake via flow cytometry. Results are shown in FIG. 24A. The points of binding saturation and killing saturation are highlighted with a vertical dotted line. Binding saturation and killing saturation was achieved at the same point, where there are about $3.0 \times 10^7$ A1 molecules per hESC.

Figure 24B:
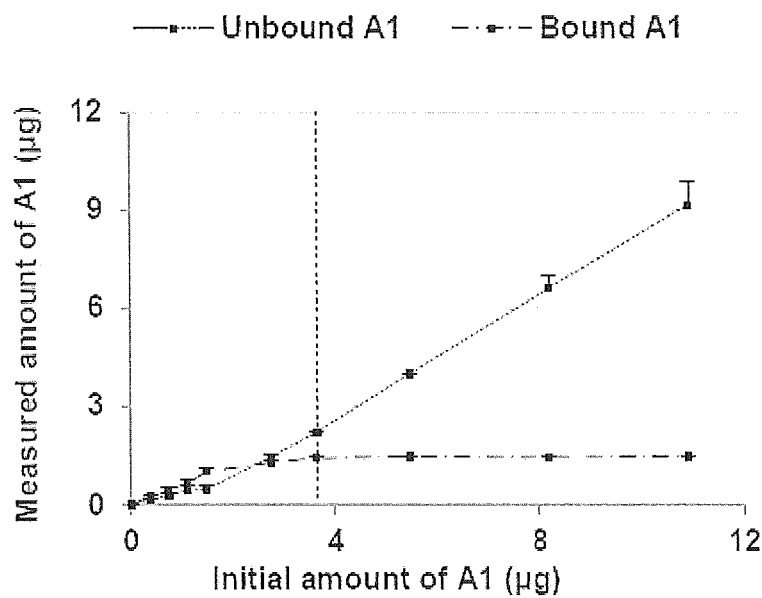

The amount of bound A1 was different between the initial amount of A1 and the amount of unbound A1 measured from stoichiometry assay. Results are shown in FIG. 24B. Point with saturated A1 killing is highlighted with vertical dotted line. Killing saturation was only achieved when the amount of unbound A1 was significantly higher than the amount of bound A1.

Example 4—A1 Recognizes O-Linked Glycan on hESC and Binding to O-Linked Glycan is Essential for A1 Cytotoxicity on hESC Tunicamycin and Benzyl-a-GalNac were used to inhibit N-glycosylation and O-glycosylation respectively. HES-3 cells (ES03 human embryonic stem cell line from WiCell Research Institute, Inc., Madison, Wis., USA) in different treatment conditions were stained with biotin-conjugated Concanavalin A or mAb to Tra-1-60. Con A binds specifically to N-linked glycans and mAb to Tra-1-60 recognizes O-linked glycan epitope on hESC. Lectin or antibodies bound to cells were detected with FITC-conjugated streptavidin or anti-mouse antibody. Results are shown in FIG. 25 in which the shaded histogram represents staining with the negative control and open histograms represent staining with primary antibodies.

Figure 25A:
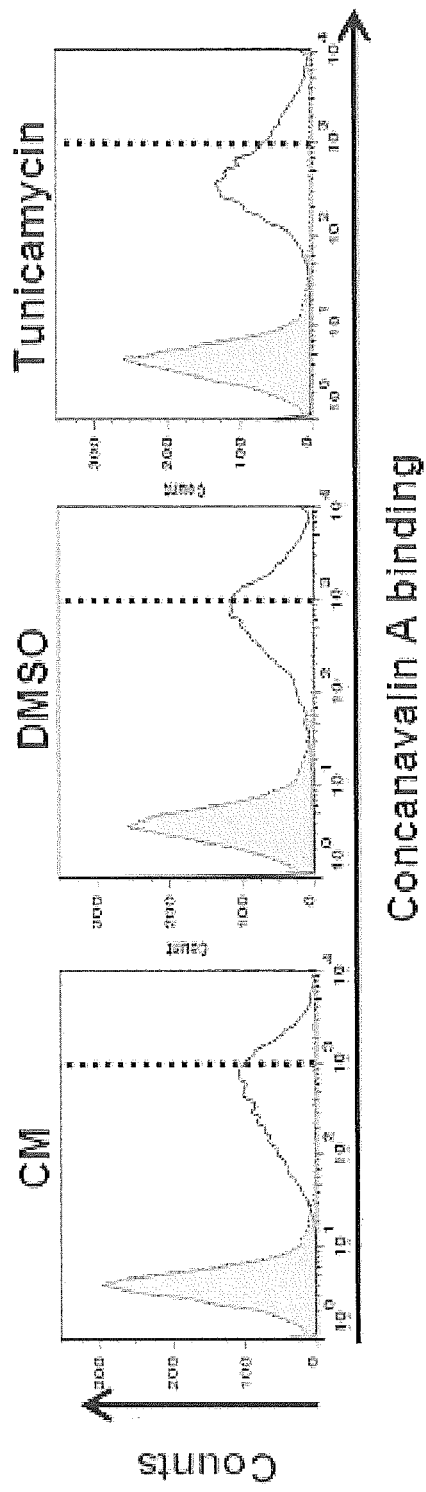
FIG. 25. Comprising panels 25A through 25C, shows N-glycosylation and O-glycosylation were partially inhibited upon inhibitor treatment. Tunicamycin and Benzyl-a-GalNac were used to inhibit N-glycosylation and O-glycosylation respectively. HES-3 in different treatment conditions were stained with biotin-conjugated Concanavalin A (25A) or mAb to Tra-1-60 (25B). Con A binds specifically to N-linked glycans and mAb to Tra-1-60 recognizes O-linked glycan epitope on hESC. Lectin or antibodies bound to cells were detected with FITC-conjugated streptavidin or anti-mouse antibody. The shaded histogram represents staining with the negative control and open histograms represent staining with primary antibodies. (25A) Binding histogram showing effect of Tunicamycin treatment, the binding histogram of biotin-conjugated Con A was shifted towards the left representing reduced N-glycosylation. (25B) Binding histogram showing effect of B-GalNac treatment, the binding histogram of mAb to Tra-1-60 was shifted towards the left representing reduced O-glycosylation. (25C) There is no change in hESC pluripotency upon inhibitors treatment. HES-3 in different treatment conditions were stained with mAb to Oct3/4. Antibodies bound to cells were detected with a fluorescein isothiocyanate (FITC)-conjugated anti-mouse antibody. The shaded histogram represents staining with the negative control and open histograms represent staining with primary antibodies. Upon either Tunicamycin treatment or B-GalNac treatment, the binding histograms of Oct3/4 antibody are comparable to these of negative controls, representing no change in hESC pluripotency upon inhibitors treatment.
Figure 25B:
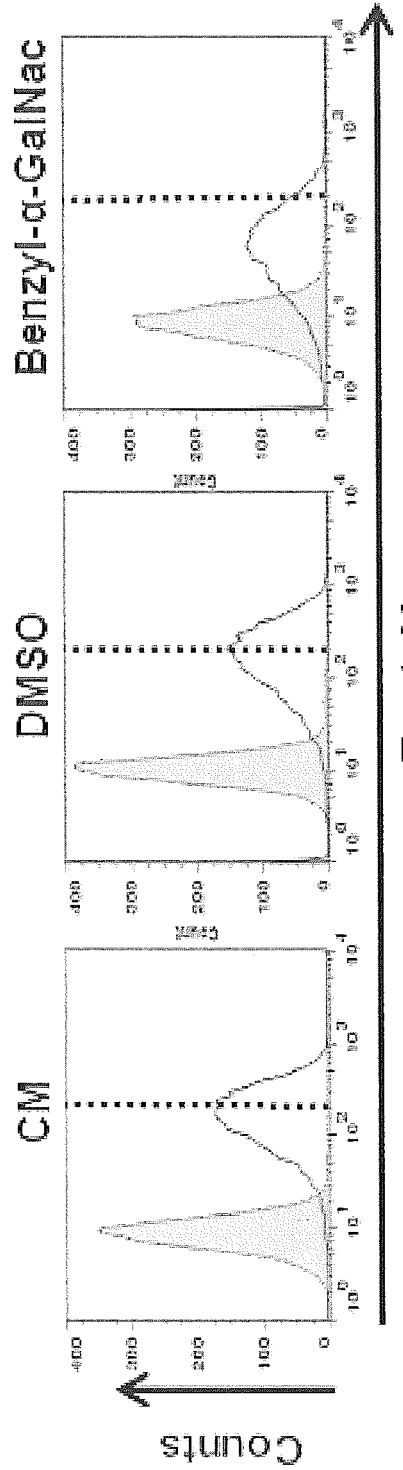

In FIG. 25A the binding histogram of biotin-conjugated Con A was shifted towards the left representing reduced N-glycosylation. In FIG. 25B the binding histogram of mAb to Tra-1-60 was shifted towards the left representing reduced O-glycosylation.

Figure 25C:
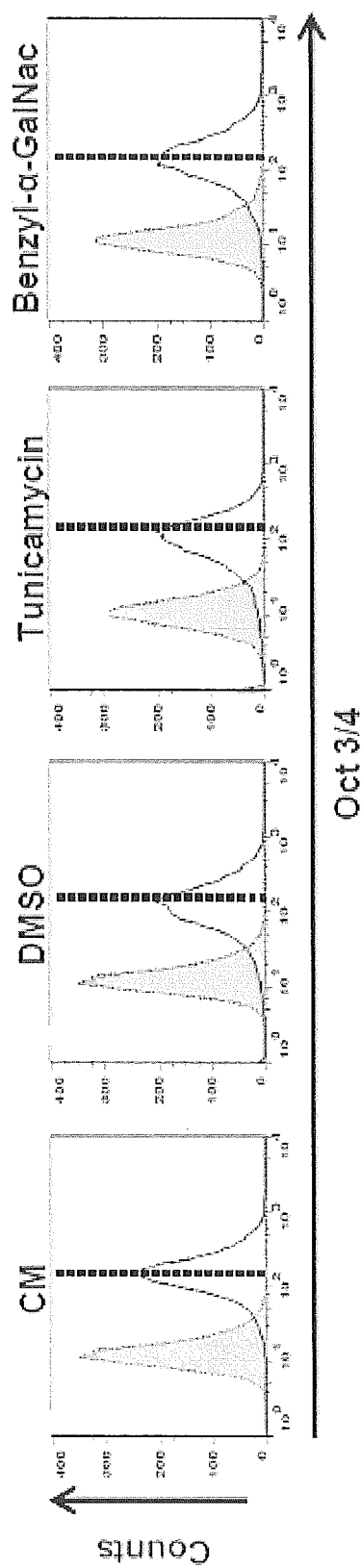

HES-3 in different treatment conditions were stained with mAb to Oct3/4. Antibodies bound to cells were detected with a fluorescein isothiocyanate (FITC)-conjugated anti-mouse antibody. Results are shown in FIG. 25C. The shaded histogram represents staining with the negative control and open histograms represent staining with primary antibodies. Upon either Tunicamycin treatment or B-GalNac treatment, the binding histograms of Oct3/4 antibody are comparable to these of negative controls, representing no change in hESC pluripotency upon inhibitors treatment.

Figure 26A:
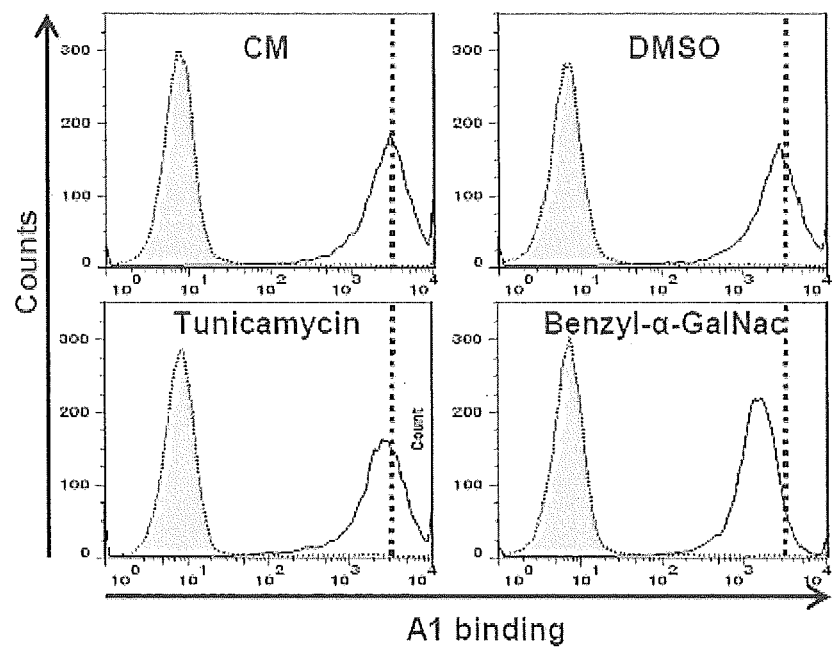
FIG. 26. Comprising panels 26A and 26B shows A1 recognizes O-linked glycan on hESC and binding to O-linked glycan is essential for A1 cytotoxicity on hESC. HES-3 in different treatment conditions was treated with chimeric A1. (26A) Antibodies bound to cells were detected with FITC-conjugated anti-human antibody. The shaded histogram represents staining with the negative control and open histograms represent staining with primary antibodies. Upon B-GalNac treatment, the binding histograms of A1 shifted to the left compared to those of negative controls and Tunicamycin treatment, representing A1 binding is only down-regulated when O-glycosylation is inhibited. A1 only recognizes O-linked glycans, but not N-linked glycans. (26B) Viability of cells was estimated by PI uptake. Cell viability in different treatment conditions was normalized to its corresponding negative controls (no A1 treatment). Upon B-GalNac treatment, cell viability upon A1 treatment was significantly higher than those of negative controls (CM control and DMSO control) as well as Tunicamycin treatment. This suggests that O-glycosylation on hESC is also essential for A1 to elicit cytotoxicity. Bars represent mean±SEM from at least 3 separate experiments.

Example 5—A1-Induced hESC Death and Reactive Oxygen Species (ROS) Production are Directly Correlated HES-3 in different treatment conditions was treated with chimeric A1. Antibodies bound to cells were detected with FITC-conjugated anti-human antibody. Results are shown in FIG. 26. In FIG. 26A the shaded histogram represents staining with the negative control and open histograms represent staining with primary antibodies. Upon B-GalNac treatment, the binding histograms of A1 shifted to the left compared to those of negative controls and Tunicamycin treatment, representing A1 binding is only down-regulated when O-glycosylation is inhibited and indicating A1 to recognizes O-linked glycans, but not N-linked glycans.

Figure 26B:
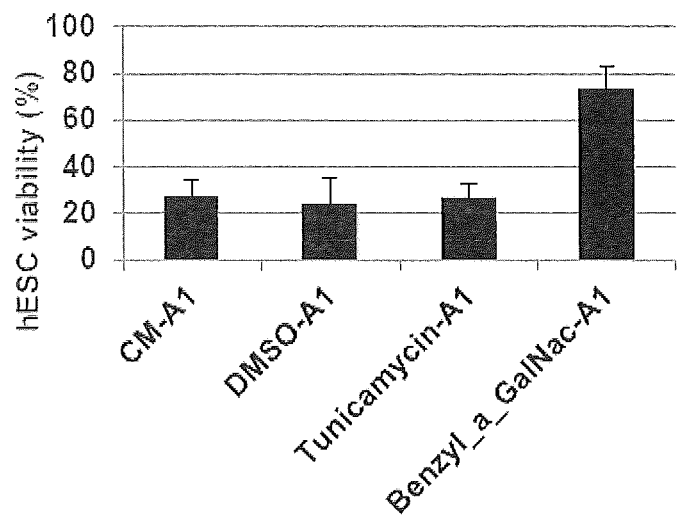

FIG. 26B shows viability of cells estimated by propidium iodide (PI) uptake. Cell viability in different treatment conditions was normalized to its corresponding negative controls (no A1 treatment). Upon B-GalNac treatment, cell viability upon A1 treatment was significantly higher than those of negative controls (CM control and DMSO control) as well as Tunicamycin treatment. This suggests that O-glycosylation on hESC is also essential for A1 to elicit cytotoxicity.

Example 6—A1-Induced hESC Death and ROS Production are Directly Correlated

After A1 treatment of hESC, there is a significant increase in the population of dead cells and high level of ROS production indicating ROS production and cell death to be directly correlated.

Figure 27A:
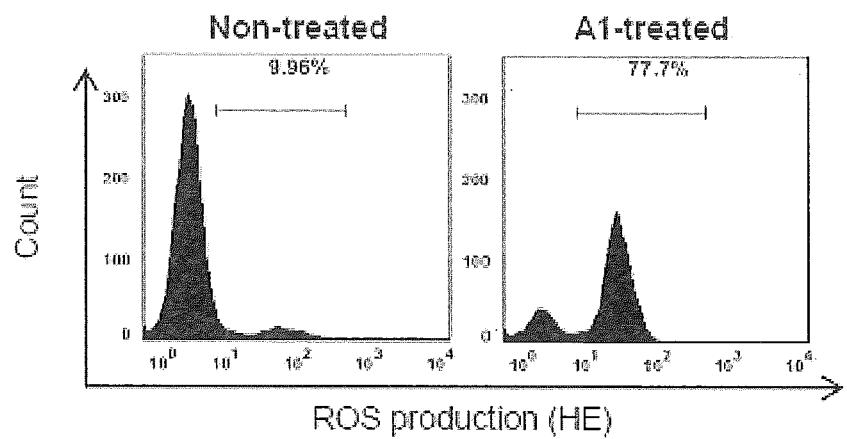
FIG. 27. Comprising panels 27A through 27D shows A1-induced hESC death and reactive oxygen species (ROS) production are directly correlated. (27A) Chart showing results of flow cytometry. Production of ROS was estimated with dihydroethidium (HE) staining via flow cytometry. Gated population represents level of ROS production. (27B) Micrographs: Alternatively, ROS production was measured with carboxy-H2DCFDA. In the presence of ROS, carboxy-H2DCFDA is oxidized to carboxy-DCF that emits green fluorescence. (27C) Chart: Bars represent mean ROS production±SEM from at least 3 independent experiments. There is massive ROS production in hESC upon A1 treatment. (27D) Chart: Cells were dual stained with Sytox green and HE to detect cell death and ROS production respectively. After A1 treatment, there is a significant increase of cell population in the upper right quadrant representing dead cells with high level of ROS production. ROS production and cell death are directly correlated.
Figure 27B:
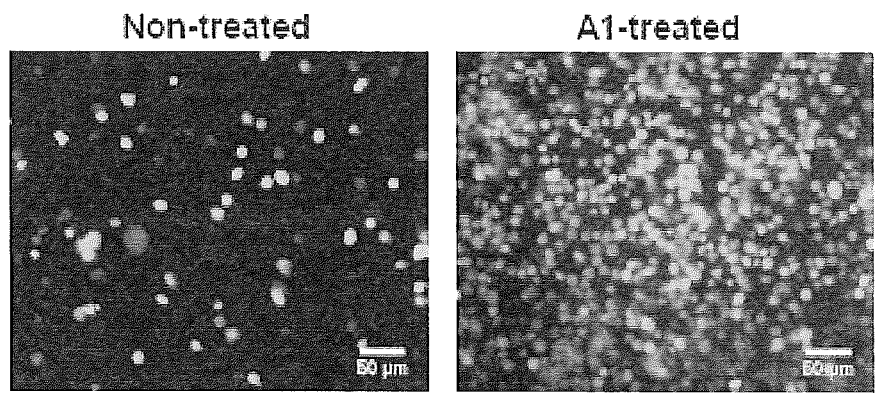
Figure 27C:
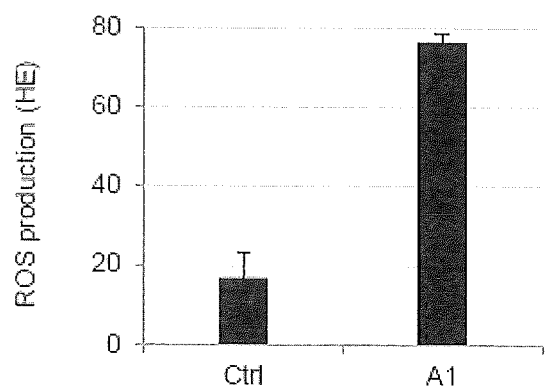

Production of ROS was estimated with dihydroethidium (HE) staining via flow cytometry (FIG. 27A). Gated population represents level of ROS production. There is massive ROS production in hESC upon A1 treatment (FIG. 27C).

ROS production was also measured with carboxy-H2DCFDA. In the presence of ROS, carboxy-H2DCFDA is oxidized to carboxy-DCF that emits green fluorescence (FIG. 27B).

Figure 27D:
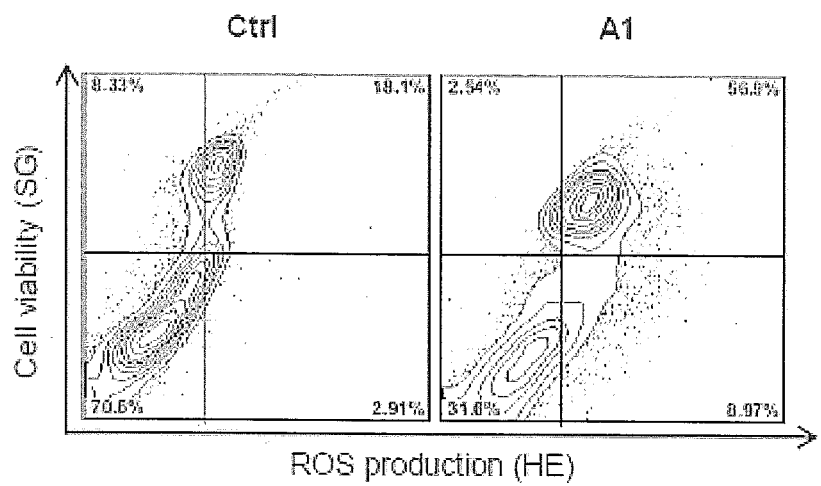

Cells were dual stained with Sytox green and HE to detect cell death and ROS production, respectively (FIG. 27D).

Example 7—ROS Production (O2-) is Required for A1-Induced hESC Death

Figure 28A:
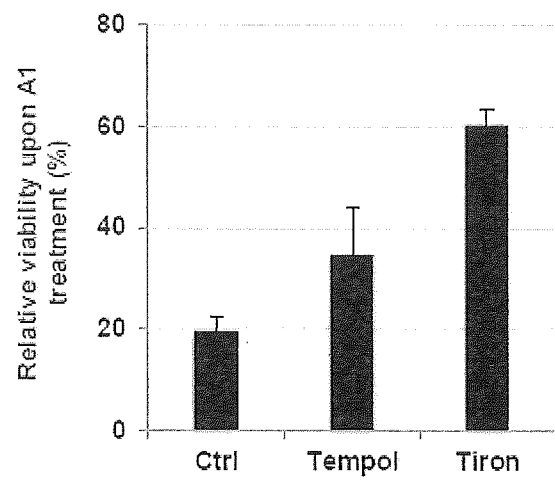
FIG. 28. Comprising panels 28A and 28B shows ROS production ($O^{2-}$) is required for A1-induced hESC death. (28A) Chart: Before the addition of A1, hESC were treated with PBS or ROS scavenger, Tiron (50 mM) or Tempol (120 mM), for 1 hour. The ROS target of both Tiron and Tempol is superoxide ($O^{2-}$). Cell viability was then measured by PI uptake. Bars represent mean cell viability±SEM from at least 3 independent experiments; ROS scavengers are able to partially block A1 killing on hESC. (28B) Chart: Cells were dual stained with Sytox green and HE to detect cell death and ROS production respectively. In the presence of Tiron, hESC after A1 treatment has a significant reduction of cell death as well ROS production. The depletion of ROS by ROS scavengers is directly correlated with reduced hESC death.

Before the addition of A1, hESC were treated with PBS or ROS scavenger, Tiron (50 mM) or Tempol (120 mM), for 1 hour. The ROS target of both Tiron and Tempol is superoxide ($O^{2-}$). Cell viability was then measured by PI uptake (FIG. 28A).

Figure 28B:
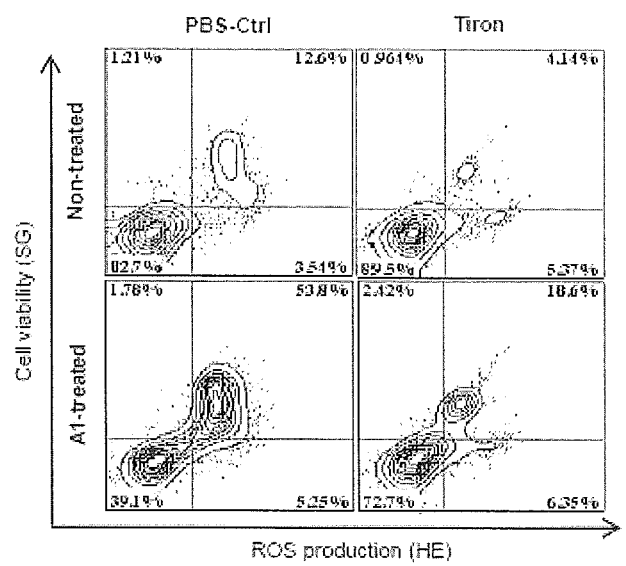

Cells were also dual stained with Sytox green and HE to detect cell death and ROS production respectively (FIG. 28B).

In the presence of Tiron, hESC after A1 treatment has a significant reduction of cell death as well ROS production. The depletion of ROS by ROS scavengers is directly correlated with reduced hESC death.

Example 8—A1-Induced hESC Death is Mediated by NADPH Oxidase

HES-3 cells were pre-incubated with NADPH oxidase inhibitors, DPI (240 µM), Apo (40 mM), or MPA (3.12 mM) for 1 hour before A1 treatment (45 minutes). Cell viability in different treatment conditions was estimated by PI uptake and normalized to their respective non-A1-treatment controls. Cells were also dual stained with Sytox green and HE to detect cell death and ROS production respectively. Results are shown in FIG. 29.

Figure 29A:
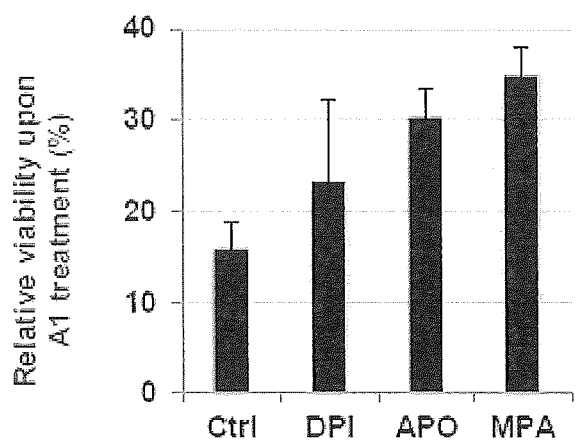
FIG. 29. Comprising panels 29A through 29F shows A1-induced hESC death is mediated by NADPH oxidase, most likely via Nox2. (29A) Chart: HES-3 was pre-incubated with NADPH oxidase inhibitors, DPI (240 µM), Apo (40 mM), or MPA (3.12 mM) for 1 hour before A1 treatment (45 minutes). Cell viability in different treatment conditions was estimated by PI uptake and normalized to their respective non-A1-treatment controls. NADPH oxidase inhibitors are able to partially block A1 killing. (29B) Chart: Cells were dual stained with Sytox green and HE to detect cell death and ROS production respectively. After A1 treatment, hESC with inhibitors treatment have a significant decrease in cell death and ROS production. Inhibition of ROS production by NADPH oxidase inhibitors is directly correlated with reduced hESC death. (29C) Summary table for targets of NADPH oxidase inhibitors. (29D) HES-3 were transfected with two different siRNA (siNox2_3787 and siNox2_3788) against Nox2. Knockdown of Nox2 was confirmed by q-RT-PCR (29D) and Western blotting (29E). Upon knock down, cells were then treated with A1 (0.5 µg/ml) and assessed for cell death after 45 minutes by PI uptake (29F). Bars represent mean±SEM from at least 3 separate experiments. Nox2 is the major source of ROS production in A1-treated hESC.
Figure 29B:
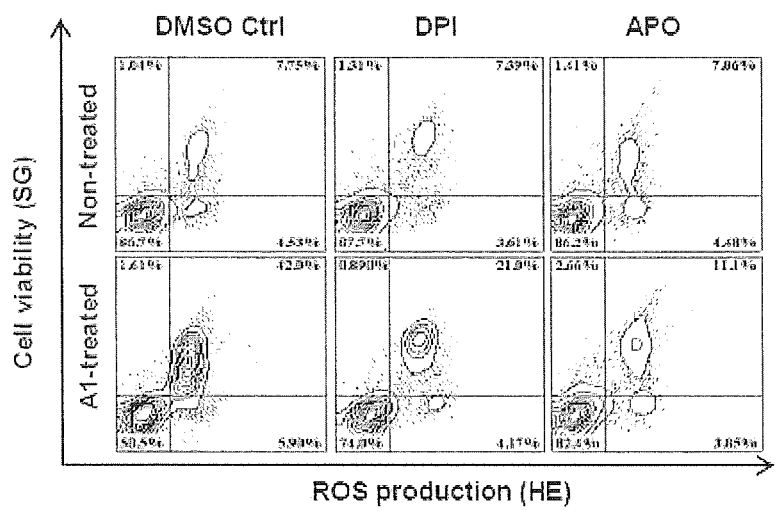
Figures 29C, 29D:
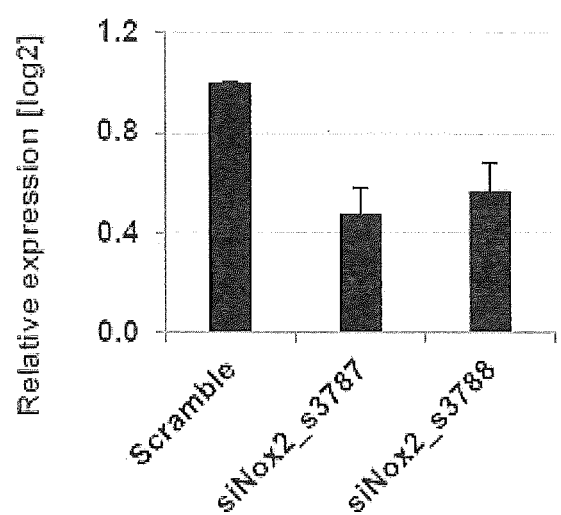
Figure 29E:
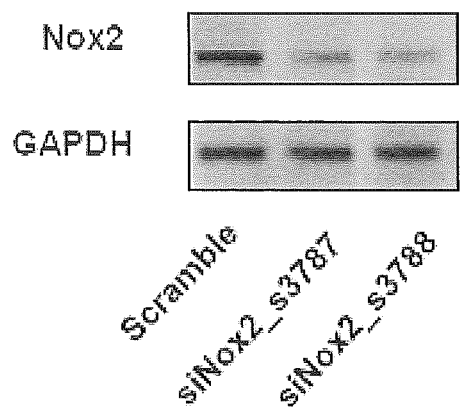
Figure 29F:
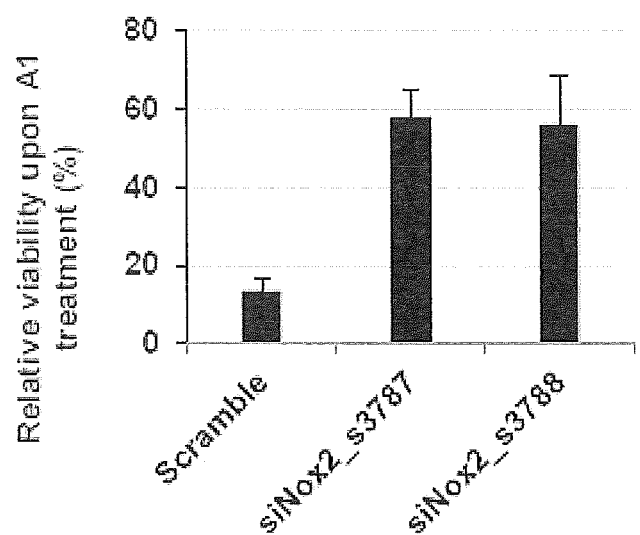

HES-3 were also transfected with two different siRNA (siNox2_3787 and siNox2_3788) against Nox2. Knockdown of Nox2 was confirmed by q-RT-PCR (FIG. 29D) and Western blotting (FIG. 29E). Upon knock down, cells were then treated with A1 (0.5 µg/ml) and assessed for cell death after 45 minutes by PI uptake (FIG. 29F).

After A1 treatment, hESC with inhibitors treatment have a significant decrease in cell death and ROS production. Inhibition of ROS production by NADPH oxidase inhibitors is directly correlated with reduced hESC death. NADPH oxidase inhibitors are able to partially block A1 killing. Nox2 is the major source of ROS production in A1-treated hESC. A1-induced hESC death is mediated by NADPH oxidase, most likely via Nox2.

Figure 30A:
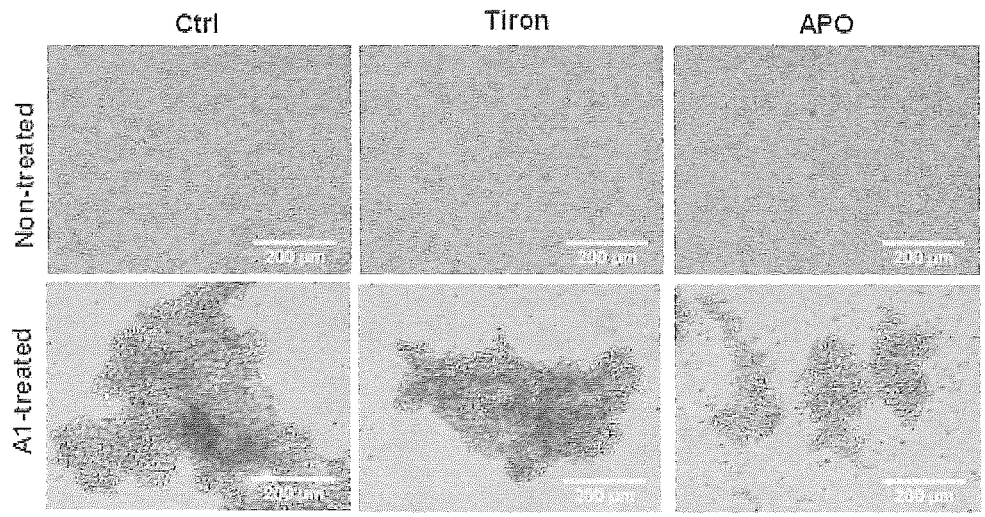
FIG. 30. Comprising panels 30A through 30D shows ROS production in A1-induced cell death lies downstream of Homotypic adhesion, and upstream of actin re-organization. (30A) Micrographs: HES-3 was pre-incubated with PBS, or Tiron (50 mM), or Apo (40 mM) for 1 hour before A1 treatment (45 minutes). Cells were assessed for Homotypic adhesion by light microscopy. Homo typic adhesion is formed in the presence of Tiron or APO. (30B) Micrographs: HES-3 was pre-incubated with PBS or Tiron (50 mM) for 1 hour before A1 treatment (45 minutes). Cell morphology were assessed by Scanning Electron Microscopy. In the presence of Tiron, A1 treatment only leads to shorten microvilli, but not massive membrane damage. (30C, 30D) Charts: HES-3 were pre-incubated with or without Tiron (50 mM) for 1 hour followed by treatment with PBS, or Latrunculin A (0.4 µg/ml), or Cytochalasin B (0.4 µg/ml), or Cytochalasin D (0.4 µg/ml) for 5 minutes before A1 treatment (45 minutes). Cell viability was estimated by PI uptake (30C) and ROS production was assessed with HE staining (30D). Bars represent mean±SEM from at least 3 separate experiments. In the presence of Tiron, actin inhibitors do not have additional inhibition effect on hESC. There is no significant difference in ROS production with or without actin inhibitor treatment.
Figure 30B:
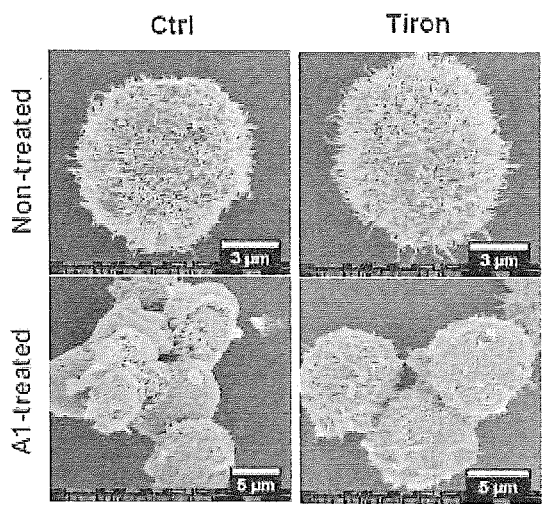

Example 9—ROS Production in A1-Induced Cell Death Lies Downstream of Homotypic Adhesion, and Upstream of Actin Re-Organization HES-3 was pre-incubated with PBS, or Tiron (50 mM), or Apo (40 mM) for 1 hour before A1 treatment (45 minutes). Cells were assessed for Homotypic adhesion by light microscopy (FIG. 30A). Homotypic adhesion is formed in the presence of Tiron or APO. HES-3 was pre-incubated with PBS or Tiron (50 mM) for 1 hour before A1 treatment (45 minutes). Cell morphology were assessed by Scanning Electron Microscopy. In the presence of Tiron, A1 treatment only leads to shorten microvilli, but not massive membrane damage (FIG. 30B).

Figure 30C:
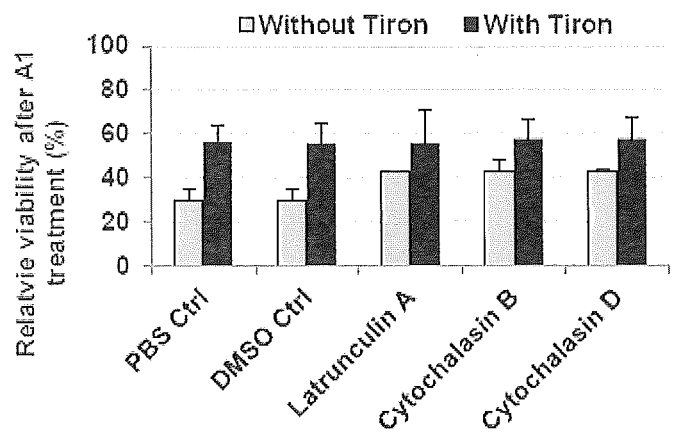
Figure 30D:
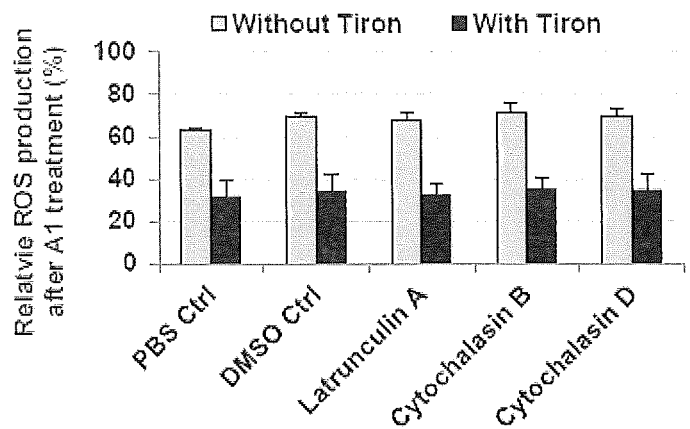

HES-3 were pre-incubated with or without Tiron (50 mM) for 1 hour followed by treatment with PBS, or Latrunculin A (0.4 µg/ml), or Cytochalasin B (0.4 µg/ml), or Cytochalasin D (0.4 µg/ml) for 5 minutes before A1 treatment (45 minutes). Cell viability was estimated by PI uptake (FIG. 30C) and ROS production was assessed with HE staining (FIG. 30D). In the presence of Tiron, actin inhibitors do not have additional inhibition effect on hESC. There is no significant difference in ROS production with or without actin inhibitor treatment. ROS production in A1-induced cell death lies downstream of Homotypic adhesion, and upstream of actin re-organization.

Example 10—Bivalency of A1

Figure 31A:
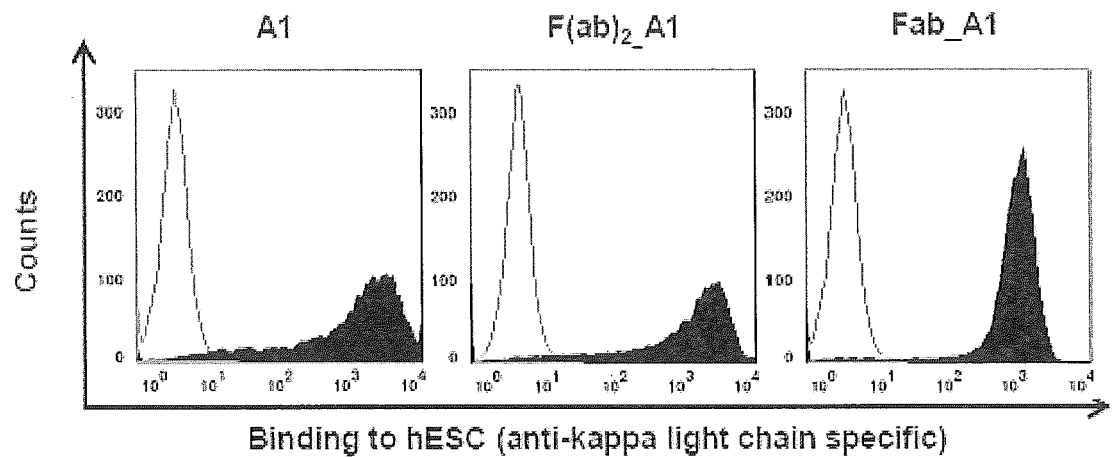
FIG. 31. Comprising panels 31A through 31C shows bivalency of A1 is required for its cytotoxicity on hESC, but not binding. Cells were incubated with the A1 (0.5 µg/ml), or F(ab)2_A1 (0.5 µg/ml), or Fab_A1 (0.5 µg/ml) for 45 minutes. (31A) Charts: The binding to hESC was detected with FITC-conjugated anti-Kappa light chain specific antibody; Both the binding of F(ab)2_A1 and Fab_A1 to hESC are comparable to A1 binding to hESC. (31B) Chart: Cell viability was estimated by PI uptake; Only the bivalent F(ab)2_A1 recapitulates the cytotoxicity of A1 on hESC. Bars represent mean±SEM from at least 3 separate experiments. (31C) Micrographs: Homotypic adhesion was assessed by light microscopy. Bivalency is required for the formation of homotypic adhesion.

Cells were incubated with the A1 (0.5 µg/ml), or F(ab)2_A1 (0.5 µg/ml), or Fab_A1 (0.5 µg/ml) for 45 minutes. The binding to hESC was detected with FITC-conjugated anti-Kappa light chain specific antibody; Both the binding of F(ab)2_A1 and Fab_A1 to hESC are comparable to A1 binding to hESC (FIG. 31 A).

Figure 31B:
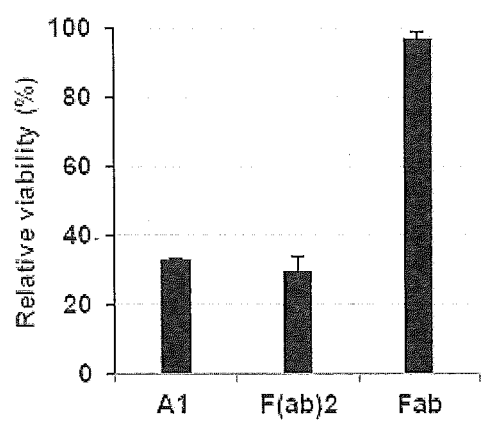

Cell viability was estimated by PI uptake; Only the bivalent F(ab)2_A1 recapitulates the cytotoxicity of A1 on hESC (FIG. 31B).

Figure 31C:
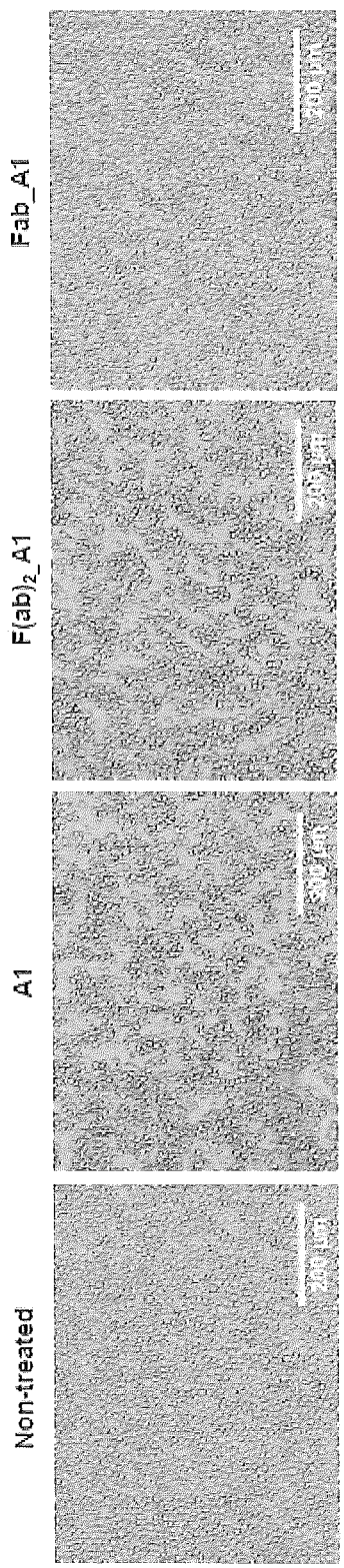

Homotypic adhesion was assessed by light microscopy. Bivalency was necessary for the formation of homotypic adhesion (FIG. 31C).

Bivalency of A1 was required for its cytotoxicity on hESC, but not binding.

REFERENCES

1 Benjamin, E. R., Martin, F. P., Fong, C. Y., Trounson, A. & Bongso, A. Embryonic stem cell lines from human blastocysts: somatic differentiation in vitro. *Nature Biotechnology* 18, 399-404 (2000).
2 Evans, M. J. & Kaufman, M. H. Establishment in culture of pluripotential cells from mouse embryos. *Nature* 292, 154-156 (1981).
3 Martin, G. R. Isolation of pluripotent cell line from early mouse embryos cultured in medium conditioned by teratocarcinoma stem cells. *Proc. Natl Acad. Sci. USA* 78, 7634-7638 (1981).
4 Thomson, J. A. et al. Embryonic Stem Cell Lines Derived from Human Blastocysts. *Science* 282, 1145-1147, doi: 10.1126/science.282.5391.1145 (1998).
5 Chang, H. et al. Trim71 cooperates with microRNAs to repress Cdkn1a expression and promote embryonic stem cell proliferation. *Nat Commun* 3, 923 (2012).
6 Levenstein, M. et al. Basic fibroblast growth factor support of human embryonic stem cell self-renewal. *Stem Cells* 24, 568-574 (2006).
7 Linlin Wang et al. Self-renewal of human embryonic stem cells requires insulin-like growth factor-1 receptor and ERBB2 receptor signaling. *Blood* 110, 4111-4119 (2007).
8 Ying, Q.-L., Nichols, J., Chambers, I. & Smith, A. BMP Induction of Id Proteins Suppresses Differentiation and Sustains Embryonic Stem Cell Self-Renewal in Collaboration with STAT3. *Cell* 115, 281-292 (2003).
9 Beattie, G. et al. Activin A maintains pluripotency of human embryonic stem cells in the absence of feeder layers. *Stem Cells* 23, 489-495 (2005).
10 Humphrey, R. et al. Maintenance of pluripotency in human embryonic stem cells is STAT3 independent. *Stem Cells* 22, 522-530 (2004).
11 Joseph, I. E. et al. Differentiation of human embryonic stem cells into embryoid bodies compromising the three embryonic germ layers. *Mol Med.* 6, 88-95 (2000).
12 Vidarsson, H., Hyllner, J. & Sartipy, P. Differentiation of human embryonic stem cells to cardiomyocytes for in vitro and in vivo applications. *Stem cell reviews* 6, 108-120, doi:10.1007/s12015-010-9113-x (2010).
13 Beqqali, A., van Eldik, W., Mummery, C. & Passier, R. Human stem cells as a model for cardiac differentiation and disease. *Cellular and molecular life sciences: CMLS* 66, 800-813, doi:10.1007/s00018-009-8476-0 (2009).
14 Dai, W. et al. Survival and maturation of human embryonic stem cell-derived cardiomyocytes in rat hearts. *Journal of molecular and cellular cardiology* 43, 504-516, doi:10.1016/j.yjmcc.2007.07.001 (2007).
15 Hazeltine, L. B. et al. Effects of substrate mechanics on contractility of cardiomyocytes generated from human pluripotent stem cells. *International journal of cell biology* 2012, 508294, doi:10.1155/2012/508294 (2012).
16 Kehat, I. et al. Human embryonic stem cells can differentiate into myocytes with structural and functional properties of cardiomyocytes. *Journal of Clinical Investigation* 108, 407-414, doi:10.1172/jci200112131 (2001).
17 Duan, Y. et al. Differentiation and enrichment of hepatocyte-like cells from human embryonic stem cells in vitro and in vivo. *Stem Cells* 25, 3058-3068 (2007).
18 Amhold, S., Klein, H., Semkova, I., Addicks, K. & Schraermeyer, U. Neurally selected embryonic stem cells induce tumor formation after long-term survival following engraftment into the subretinal space. *Invest Ophthalmol Vis Sci* 45, 4251-4255, doi:10.1167/iovs.03-1108 (2004).
19 Carpenter, M. K. et al. Enrichment of neurons and neural precursors from human embryonic stem cells. *Exp Neurol* 172, 383-397 (2001).
20 Hu, B. Y. & S. C., Z. Directed differentiation of neural-stem cells and subtype-specific neurons from hESCs. *Methods Mol. Biol.* 636, 123-137 (2010).
21 Parsons, X. H. et al. Efficient derivation of human neuronal progenitors and neurons from pluripotent human embryonic stem cells with small molecule induction. *Journal of visualized experiments: JoVE*, e3273, doi: 10.3791/3273 (2011).
22 Zhou, J. M., Chu, J. X. & Chen, X. J. An improved protocol that induces human embryonic stem cells to differentiate into neural cells in vitro. *Cell Biol Int* 32, 80-85, doi:10.1016/j.cellbi.2007.08.015 (2008).
23 Bai, H. & Wang, Z. Z. Directing human embryonic stem cells to generate vascular progenitor cells. *Gene therapy* 15, 89-95, doi:10.1038/sj.gt.3303005 (2008).
24 Ferreira, L. S. et al. Vascular progenitor cells isolated from human embryonic stem cells give rise to endothelial and smooth muscle like cells and form vascular networks in vivo. *Circulation research* 101, 286-294, doi:10.1161/CIRCRESAHA.107.150201 (2007).
25 Jezierski, A., Swedani, A. & Wang, L. Development of hematopoietic and endothelial cells from human embryonic stem cells: lessons from the studies using mouse as a model. *The Scientific World Journal* 7, 1950-1964, doi:10.1100/tsw.2007.310 (2007).
26 Levenberg, S., Zoldan, J., Basevitch, Y. & Langer, R. Endothelial potential of human embryonic stem cells. *Blood* 110, 806-814, doi:10.1182/blood-2006-08-019190 (2007).
27 Li, Z., Han, Z. & Wu, J. C. Transplantation of human embryonic stem cell-derived endothelial cells for vascular diseases. *Journal of cellular biochemistry* 106, 194-199, doi:10.1002/jcb.22003 (2009).
28 Xiong, Q. et al. A fibrin patch-based enhanced delivery of human embryonic stem cell-derived vascular cell trans- 28. plantation in a porcine model of postinfarction left ventricular remodeling. *Stem Cells* 29, 367-375, doi:10.1002/stem.580 (2011).
29. Sottile, V., Thomson, A. & McWhir, J. In vitro osteogenic differentiation of human ES cells. *CLONING AND STEM CELLS* 5, 2 (2003).
30. Bielby, R. C., Boccaccini, A. R., Polak, J. M. & Buttery, L. D. In vitro differentiation and in vivo mineralization of osteogenic cells derived from human embryonic stem cells. *Tissue Eng* 10, 9-10 (2004).
31. Green, H., Easley, K. & Iuchi, S. Marker succession during the development of keratinocytes from cultured human embryonic stem cells. *Proceedings of the National Academy of Sciences of the United States of America* 100, 15625-15630, doi:10.1073/pnas.0307226100 (2003).
32. Idelson, M. et al. Directed differentiation of human embryonic stem cells into functional retinal pigment epithelium cells. *Cell Stem Cell* 5, 396-408, doi:10.1016/j.stem.2009.07.002 (2009).
33. Lu, B. et al. Long-term safety and function of RPE from human embryonic stem cells in preclinical models of macular degeneration. *Stem Cells* 27, 2126-2135, doi:10.1002/stem.149 (2009).
34. Ben-David, U. & Benvenisty, N. The tumorigenicity of human embryonic and induced pluripotent stem cells. *Nat Rev Cancer* 11, 268-277, doi:10.1038/nrc3034 (2011).
35. Blum, B. & Benvenisty, N. The Tumorigenicity of Human Embryonic Stem Cells. *Adv Cancer Res* 100, 133-158, doi:10.1016/50065-230x(08)00005-5 (2008).
36. Hentze, H., Graichen, R. & Colman, A. Cell therapy and the safety of embryonic stem cell-derived grafts. *Trends Biotechnol* 25, 24-32, doi:10.1016/j.tibtech.2006.10.010 (2007).
37. Choo, A. B. et al. Selection against undifferentiated human embryonic stem cells by a cytotoxic antibody recognizing podocalyxin-like protein-1. *Stem Cells* 26, 1454-1463, doi:10.1634/stemcells.2007-0576 (2008).
38. Lim, D. Y. et al. Cytotoxic antibody fragments for eliminating undifferentiated human embryonic stem cells. *Journal of biotechnology* 153, 77-85, doi:10.1016/j.jbiotec.2011.03.017 (2011).
39. Rao, M. Tumorigenesis and embryonic stem cell-derived therapy. *Stem cells and development* 16, 903-904, doi:10.1089/scd.2007.9986 (2007).
40. Fujikawa, T. et al. Teratoma Formation Leads to Failure of Treatment for Type I Diabetes Using Embryonic Stem Cell-Derived Insulin-Producing Cells. *The American Journal of Pathology* 166, 1781-1791, doi:10.1016/s0002-9440(10)62488-1 (2005).
41. Hentze, H. et al. Teratoma formation by human embryonic stem cells: evaluation of essential parameters for future safety studies. *Stem Cell Res* 2, 198-210, doi:10.1016/j.scr.2009.02.002 (2009).
42. Shih, C. C., Forman, S. J., Chu, P. & Slovak, M. Human embryonic stem cells are prone to generate primitive, undifferentiated tumors in engrafted human fetal tissues in severe combined immunodeficient mice. *Stem cells and development* 16, 893-902, doi:10.1089/scd.2007.0070 (2007).
43. Werbowetski-Ogilvie, T. E. et al. Characterization of human embryonic stem cells with features of neoplastic progression. *Nat Biotechnol* 27, 91-97, doi:10.1038/nbt.1516 (2009).
44. Yang, S. et al. Tumor progression of culture-adapted human embryonic stem cells during long-term culture. *Genes Chromosomes Cancer* 47, 665-679, doi:10.1002/gcc.20574 (2008).
45. Lawrenz, B. et al. Highly sensitive biosafety model for stem-cell-derived grafts. *Cytotherapy* 6, 212-222 (2004).
46. Drukker, M. & Benvenisty, N. The immunogenicity of human embryonic stem-derived cells. *Trends Biotechnol* 22, 136-141, doi:10.1016/j.tibtech.2004.01.003 (2004).
47. Fong, C. Y., Peh, G. S., Gauthaman, K. & Bongso, A. Separation of SSEA-4 and TRA-1-60 labelled undifferentiated human embryonic stem cells from a heterogeneous cell population using magnetic-activated cell sorting (MACS) and fluorescence-activated cell sorting (FACS). *Stem cell reviews* 5, 72-80, doi:10.1007/s12015-009-9054-4 (2009).
48. Tang, C. et al. An antibody against SSEA-5 glycan on human pluripotent stem cells enables removal of teratoma-forming cells. *Nat Biotechnol* 29, 829-834, doi:10.1038/nbt.1947 (2011).
49. Handgretinger, R. et al. Isolation and transplantation of highly purified autologous peripheral CD34($^+$) progenitor cells: purging efficacy, hematopoietic reconstitution and long-term outcome in children with high-risk neuroblastoma. *Bone Marrow Transplant* 29, 731-736, doi:10.1038/sj/bmt/1703536 (2002).
50. Imai, Y. et al. Isolation and transplantation of highly purified autologous peripheral CD34+ progenitor cells: purging efficacy, hematopoietic reconstitution in non-Hodgkin's lymphoma (NHL): results of Japanese phase II study. *Bone Marrow Transplant* 35, 479-487, doi:10.1038/sj.bmt.1704819 (2005).
51. Ben-David, U. et al. Selective elimination of human pluripotent stem cells by an oleate synthesis inhibitor discovered in a high-throughput screen. *Cell Stem Cell* 12, 167-179, doi:10.1016/j.stem.2012.11.015 (2013).
52. Chung, S. et al. Genetic selection of sox1GFP-expressing neural precursors removes residual tumorigenic pluripotent stem cells and attenuates tumor formation after transplantation. *J Neurochem* 97, 1467-1480, doi:10.1111/j.1471-4159.2006.03841.x (2006).
53. Gerrard, L., Zhao, D., Clark, A. J. & Cui, W. Stably transfected human embryonic stem cell clones express OCT4-specific green fluorescent protein and maintain self-renewal and pluripotency. *Stem Cells* 23, 124-133, doi:10.1634/stemcells.2004-0102 (2005).
54. Xu, C., S, P., N, R. & M K., C. Characterization and Enrichment of Cardiomyocytes Derived From Human Embryonic Stem Cells. *Circulation research* 91, 501-508, doi:10.1161/01.res.0000035254.80718.91 (2002).
55. Kumashiro, Y. et al. Enrichment of Hepatocytes Differentiated from Mouse Embryonic Stem Cells as a Transplantable Source. *Transplantation* 79, 550-557, doi:10.1097/01.tp.0000153637.44069.c6 (2005).
56. Bieberich, E., Silva, J., Wang, G., Krishnamurthy, K. & Condie, B. G. Selective apoptosis of pluripotent mouse and human stem cells by novel ceramide analogues prevents teratoma formation and enriches for neural precursors in ES cell-derived neural transplants. *J Cell Biol* 167, 723-734, doi:10.1083/jcb.200405144 (2004).
57. Cao, F. et al. In vivo visualization of embryonic stem cell survival, proliferation, and migration after cardiac delivery. *Circulation* 113, 1005-1014, doi:10.1161/CIRCULATIONAHA.105.588954 (2006).
58. Jung, J. et al. Ablation of tumor-derived stem cells transplanted to the central nervous system by genetic modification of embryonic stem cells with a suicide gene. *Hum Gene Ther* 18, 1182-1192, doi:10.1089/hum.2007.078 (2007).

59 Rong, Z., Fu, X., Wang, M. & Xu, Y. A scalable approach to prevent teratoma formation of human embryonic stem cells. *J Biol Chem* 287, 32338-32345, doi:10.1074/jbc.M112.383810 (2012).

60 Schuldiner, M., J., I.-E. & N., B. Selective ablation of human embryonic stem cells expressing a 'suicide' gene. *Stem Cells* 21, 257-265 (2003).

61 Bazil, V., Brandt, J., Tsukamoto, A. & Hoffman, R. Apoptosis of human hematopoietic progenitor cells induced by crosslinking of surface CD43. *Blood.* 1995 Jul. 15; 86(2):502-11. 86, 502-511 (1995).

62 Matsuoka, S. et al. a novel type of cell death of lymphocytes induced by a monoclonal antibody without participation of complement. *The Journal of experimental medicine* 181, 2007-2015 (1995).

63 Zhang, C. H., Xu, Y. H., Gu, J. J. & Schlossman, S. F. A cell surface receptor defined by a mAb mediates a unique type of cell death similar to oncosis. *Proc Natl Acad Sci* 95, 6290-6295 (1998).

64 Zhang, N., Khawli, L. A., Hu, P. & Epstein, A. L. Generation of rituximab polymer may cause hyper-cross-linking-induced apoptosis in non-Hodgkin's lymphomas. *Clin Cancer Res* 11, 5971-5980, doi:10.1158/1078-0432.CCR-05-0554 (2005).

65 Honeychurch, J. et al. Antibody-induced nonapoptotic cell death in human lymphoma and leukemia cells is mediated through a novel reactive oxygen species-dependent pathway. *Blood* 119, 3523-3533, doi:10.1182/blood-2011-12-395541 (2012).

66 Ivanov, A. et al. Monoclonal antibodies directed to CD20 and HLA-DR can elicit homotypic adhesion followed by lysosome-mediated cell death in human lymphoma and leukemia cells. *J Clin Invest.* 119, 2143-2159 (2009).

67 Alduaij, W. et al. Novel type II anti-CD20 monoclonal antibody (GA101) evokes homotypic adhesion and actin-dependent, lysosome-mediated cell death in B-cell malignancies. *Blood* 117, 4519-4529, doi:10.1182/blood-2010-07-296913 (2011).

68 Loo, D. et al. The glycotope-specific RAV12 monoclonal antibody induces oncosis in vitro and has antitumor activity against gastrointestinal adenocarcinoma tumor xenografts in vivo. *Molecular cancer therapeutics* 6, 856-865, doi:10.1158/1535-7163.MCT-06-0581 (2007).

69 Hernandez, A. M. et al. Anti-NeuGcGM3 antibodies, actively elicited by idiotypic vaccination in nonsmall cell lung cancer patients, induce tumor cell death by an oncosis-like mechanism. *J Immunol* 186, 3735-3744, doi:10.4049/jimmunol.1000609 (2011).

70 Roque-Navarro, L. et al. Anti-ganglioside antibody-induced tumor cell death by loss of membrane integrity. *Molecular cancer therapeutics* 7, 2033-2041, doi:10.1158/1535-7163.MCT-08-0222 (2008).

71 Duprez, L., Wirawan, E., Vanden Berghe, T. & Vandenabeele, P. Major cell death pathways at a glance. *Microbes Infect* 11, 1050-1062, doi:10.1016/j.micinf.2009.08.013 (2009).

72 Trump, B. E., Berezesky, I. K., Chang, S. H. & Phelps, P. C. The Pathways of Cell Death: Oncosis, Apoptosis, and Necrosis. *Toxicologic Pathology* 25, 82-88, doi:10.1177/019262339702500116 (1997).

73 Weerasinghe, P. & Buja, L. M. Oncosis: an important non-apoptotic mode of cell death. *Experimental and molecular pathology* 93, 302-308, doi:10.1016/j.yexmp.2012.09.018 (2012).

74 Kerr, J. F., Wyllie, A. H. & Currie, A. R. Apoptosis—A Basic Biological Phenomenon with Wide-ranging Implications in Tissue Kinetics. *Br J Cancer* 26, 239-257 (1972).

75 Favaloro, B., Allocati, N., Graziano, V., Di, L. C. & De Laurenzi, V. Role of apoptosis in disease. *Aging* (Albany N.Y.) 4, 330-349 (2012).

76 Takuma, K., Yan, S. S., Stern, D. M. & Yamada, K. Mitochondrial dysfunction, endoplasmic reticulum stress, and apoptosis in Alzheimer's disease. *J Pharmacol Sci* 97, 312-316 (2005).

77 Hockenbery, D. Defining Apoptosis. *Am J Pathol* 146, 16-19 (1995).

78 Susan, E. Apoptosis—a review of programmed cell death. *Toxicol Pathol* 35, 495-516 (2007).

79 Van, C. S. & Van, D. B. Morphological and biochemical aspects of apoptosis, oncosis and necrosis. *Anat Histol Embryol* 31, 214-223 (2002).

80 Majno, G. & Joris, I. Apoptosis, oncosis, and necrosis. An overview of cell death. *Am J Pathol* 146, 3-15 (1995).

81 Burris, H. A., 3rd et al. Phase 1 experience with an anti-glycotope monoclonal antibody, RAV12, in recurrent adenocarcinoma. *Clin Cancer Res* 16, 1673-1681, doi:10.1158/1078-0432.CCR-09-2263 (2010).

82 Tan, H. L., Fong, W. J., Lee, E. H., Yap, M. & Choo, A. mAb 84, a cytotoxic antibody that kills undifferentiated human embryonic stem cells via oncosis. *Stem Cells* 27, 1792-1801, doi:10.1002/stem.109 (2009).

83 Heins, N. et al. Clonal derivation and characterization of human embryonic stem cell lines. *Journal of biotechnology* 122, 511-520, doi:10.1016/j.jbiotec.2005.10.010 (2006).

84 Liu, Y. et al. A novel chemical-defined medium with bFGF and N2B27 supplements supports undifferentiated growth in human embryonic stem cells. *Biochemical and biophysical research communications* 346, 131-139, doi:10.1016/j.bbrc.2006.05.086 (2006).

85 Doherty, G. J. & McMahon, H. T. Mediation, modulation, and consequences of membrane-cytoskeleton interactions. *Annual review of biophysics* 37, 65-95, doi:10.1146/annurev.biophys.37.032807.125912 (2008).

86 Dean, W. & Frieden, C. Actin Polymerization The Mechanism of Action of Cytochalasin D. *The Journal of Biological Chemistry* 261, 15974-15980 (1986).

87 Yarmola, E. G., Somasundaram, T., Boring, T. A., Spector, I. & Bubb, M. R. Actin-latrunculin A structure and function. Differential modulation of actin-binding protein function by latrunculin A. *J Biol Chem* 275, 28120-28127, doi:10.1074/jbc.M004253200 (2000).

The invention claimed is:

1. A method of destroying an undifferentiated pluripotent cell or cells in a sample containing such cells, the method comprising contacting a sample of cells containing an undifferentiated pluripotent cell or cells with an antibody that binds a glycosylated protein, wherein the glycosylation comprises the glycan motif Fucα1-2Galβ1-3GlcNAcβ1-3Galβ1 or Fucα1-2Galβ1-3GlcNAc, wherein the antibody is cytotoxic against undifferentiated pluripotent cells, and wherein the antibody comprises:

at least one light chain variable region incorporating the following CDRs:

```
                                          (SEQ ID NO: 1)
CDR1: SASSSVSYMF (SEQ ID NO: 2)
CDR2: LTSNLAS (SEQ ID NO: 3)
CDR3: QQWSSNPYT;
``` and
at least one heavy chain variable region incorporating the following CDRs:

```
                                          (SEQ ID NO: 4)
CDR1: GFTFSNYYMN (SEQ ID NO: 5)
CDR2: EIRLKSNNYATHYAESVKG (SEQ ID NO: 6)
CDR3: FGY.
```

2. A method of removing an undifferentiated pluripotent cell or cells from a sample containing such cells, the method comprising contacting a sample of cells containing an undifferentiated pluripotent cell or cells with an antibody that binds a glycosylated protein, wherein the glycosylation comprises the glycan motif Fucα1-2Galβ1-3GlcNAcβ1-3Galβ1 or Fucα1-2Galβ1-3GlcNAc, wherein the antibody is cytotoxic against undifferentiated pluripotent cells, and wherein the antibody comprises:

at least one light chain variable region incorporating the following CDRs:

```
                                          (SEQ ID NO: 1)
CDR1: SASSSVSYMF (SEQ ID NO: 2)
CDR2: LTSNLAS (SEQ ID NO: 3)
CDR3: QQWSSNPYT;
``` and
at least one heavy chain variable region incorporating the following CDRs:

```
                                          (SEQ ID NO: 4)
CDR1: GFTFSNYYMN (SEQ ID NO: 5)
CDR2: EIRLKSNNYATHYAESVKG (SEQ ID NO: 6)
CDR3: FGY.
```

3. A method of preparing a composition containing cells differentiated from undifferentiated pluripotent cells which composition contains substantially no undifferentiated pluripotent cells, the method comprising:

(i) providing a population of cells comprising undifferentiated pluripotent cells and cells differentiated from undifferentiated pluripotent stem cells;
(ii) contacting the population with an antibody under conditions permitting the antibody to kill undifferentiated pluripotent cells; and
(iii) separating live cells remaining after step (ii) from dead cells;
wherein the antibody binds a glycosylated protein, wherein the glycosylation comprises the glycan motif Fucα1-2Galβ1-3GlcNAcβ1-3Galβ1 or Fucα1-2Galβ1-3GlcNAc, wherein the antibody is cytotoxic against undifferentiated pluripotent cells, and wherein the antibody comprises:

at least one light chain variable region incorporating the following CDRs:

```
                                          (SEQ ID NO: 1)
CDR1: SASSSVSYMF (SEQ ID NO: 2)
CDR2: LTSNLAS (SEQ ID NO: 3)
CDR3: QQWSSNPYT;
``` and
at least one heavy chain variable region incorporating the following CDRs:

```
                                          (SEQ ID NO: 4)
CDR1: GFTFSNYYMN (SEQ ID NO: 5)
CDR2: EIRLKSNNYATHYAESVKG (SEQ ID NO: 6)
CDR3: FGY.
```

4. The method of claim 3 further comprising mixing the separated cells with a pharmaceutically acceptable carrier, adjuvant or diluent.

5. The method of claim 1, wherein the antibody is a monoclonal antibody produced from hybridoma cell line TAG-A1, deposited with American Type Culture Collection under Accession Number PTA-121134.

6. The method of claim 2, wherein the antibody is a monoclonal antibody produced from hybridoma cell line TAG-A1, deposited with American Type Culture Collection under Accession Number PTA-121134.

7. The method of claim 3, wherein the antibody is a monoclonal antibody produced from hybridoma cell line TAG-A1, deposited with American Type Culture Collection under Accession Number PTA-121134.

8. The method of claim 1, wherein the glycan motif is Fucα1-2Galβ1-3GlcNAcβ1-3Galβ1.

9. The method of claim 2, wherein the glycan motif is Fucα1-2Galβ1-3GlcNAcβ1-3Galβ1.

10. The method of claim 3, wherein the glycan motif is Fucα1-2Galβ1-3GlcNAcβ1-3Galβ1.

11. The method of claim 1, wherein the antibody is bivalent.

12. The method of claim 2, wherein the antibody is bivalent.

13. The method of claim 3, wherein the antibody is bivalent.

* * * * *